US008133492B1

(12) United States Patent (10) Patent No.: US 8,133,492 B1
Wang (45) Date of Patent: Mar. 13, 2012

(54) PNEUMOCOCCUS POLYSACCHARIDE-RELATED VACCINES

(75) Inventor: Denong Wang, Middletown City, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 898 days.

(21) Appl. No.: 11/472,731

(22) Filed: Jun. 21, 2006

Related U.S. Application Data

(63) Continuation of application No. 10/367,204, filed on Feb. 14, 2003, now abandoned.

(51) Int. Cl.
*A61K 39/385* (2006.01)
*A61K 39/116* (2006.01)
(52) U.S. Cl. .............................. 424/197.11; 424/203.1
(58) Field of Classification Search ........................ None
See application file for complete search history.

(56) References Cited

U.S. PATENT DOCUMENTS

| | | | |
|---|---|---|---|
| 3,826,678 A | 7/1974 | Hoffman et al. |
| 5,098,846 A | 3/1992 | Fleming |
| 5,563,056 A | 10/1996 | Swan et al. |
| 6,051,380 A | 4/2000 | Sosnowski et al. |
| 6,056,964 A | 5/2000 | Rook et al. |
| 6,080,589 A | 6/2000 | Kandil et al. |
| 6,174,683 B1 | 1/2001 | Hahn et al. |
| 6,287,568 B1 | 9/2001 | Wang et al. |
| 6,329,206 B1 | 12/2001 | Wagner et al. |
| 6,355,491 B1 | 3/2002 | Zhou et al. |
| 2003/0228637 A1 | 12/2003 | Wang |
| 2004/0033546 A1 | 2/2004 | Wang |
| 2004/0253634 A1 | 12/2004 | Wang |

FOREIGN PATENT DOCUMENTS

WO WO 02/83918 10/2001

OTHER PUBLICATIONS

Barington et al. (Infect. Immun., 61:432-438, 1993).*
Ellis, R.W. (Chapter 29 of "Vaccines" [Plotkin, S.A. et al. (eds) W. B. Saunders company (Philadelphia) 1988, pp. 568-575.*
VanCott et al. (Vaccine, 14:392-398, 1996).*
Alonso de Velasco (Infect. Immun., 62:799-808, 1994).*
U.S. Appl. No. 60/282,926, filed Apr. 10, 2001 on behalf of Denong Wang.
International Search Report issued on Nov. 5, 2002 in connection with PCT International Application No. PCT/US02/11612, filed Apr. 10, 2002 International Publication No. WO 02/083,918 A3, published Oct. 24, 2002, on behalf of the Trustees of Columbia University in the City of New York.
Written Opinion issued on Mar. 17, 2004 in connection with PCT International Application No. PCT/US02/11612, filed Apr. 10, 2002, International Publication No. WO 02/083,918 A3, published Oct. 24, 2002, on behalf of the Trustees of Columbia University in the City of New York.

International Preliminary Examination Report issued on Aug. 27, 2004 in connection with PCT International Application No. PCT/US02/11612, filed Apr. 10, 2002, international Publication No. WO 02/083,918 A3, Published Oct. 24, 2002, on behalf of the Trustees of Columbia University in the City of New York.
Allen, P.Z. and E.A. Kabat (1958) "Immunochemical studies on blood groups," *J. Immunol.* 82: 358-372.
Allen, P.Z. & B. Prescott (1978) "Immunochemical studies on a *Mycoplasma pneumoniae* polysaccharide fraction: cross-reactions with type 23 and 32 antipneumococcal rabbit sera," *Infect. Immun.* 20: 421-429.
Alon, U. et al. (1999) "Broad patterns of gene expression revealed by clustering analysis of tumor and normal colon tissues probed by oligonucleotide arrays," *Proc. Natl. Acad. Sci. USA* 96: 6745-6750.
Basten, A. & J.G. Howard in Contemporary Topics in Immunobiology, vol. 2. (ed. A.J.S. Davies) (Plenum, New York; 1973), 265-291.
Beagley, K.W. et al. in Cytokine Regulation of Humoral Immunity (ed. C.M. Snapper) (John Wiley & Sons Ltd.: Chichester, New York, Brisbane, Toronto, Singapore; 1996), 391-408.
Ben-Dor, A. et al. (1999) "Clustering gene expression patterns," *J. Comput. Biol.* 6: 281-297.
Blaustein, R.O. et al. (1989) "Anthrax toxin: channel—forming activity of protective antigen in planar phospholipid bilayers," *Proc. Natl. Acad. Sci.* USA 86: 2209-2213.
Boxall, E.H. et al. (1997) "A novel assay for hepatitis B e markers," *J. Med. Virol.* 52: 280-285.
Brown, M.P.S. et al. (2000) "Knowledge-based analysis of microarray gene expression data by using support vector machines," *PNAS* 97:262-267.
Brown, P.O. and D. Botstein (1999) "Exploring the new world of the genome with DNA microarrays," *Nat. Genet. Supp.* 21: 33-37.
Burges, C.J.C. (1998) "A tutorial on support vector machines for pattern recognition," *Data Mining and Knowledge Discovery* 2: 121-167.
Burrel, C.J. (1980) "Serological markers of hepatitis B infection," *Clin. Gastroenterol.* 9: 47-63.
Butte, A.J. & T.S. Kohane (2000) "Mutual information relevance networks: functional genomic clustering using pairwise entropy measurements," *Pac. Symp. Biocomput.*: 418-429.
Chalfie, M. (1995) "Green fluorescent protein," *Photochem. Photobiol.* 62: 651-656.
Charlton, S. et al. (1999) "Characterization of the exosporium of *Bacillus cereus*," *J. Appl. Microbiol.* 87: 241-245.
Chen, H. T. et al. (1987) "Immunochemical studies on monoclonal. antibodies to stearyl-isomaltotetraose from C58/J and a C57BL/10 nude mouse," *Mol. Immunol.* 24: 333-338.
Cisar, J. et al. (1975) "Binding properties of immunoglobulin combining sites specific for terminal or nonterminal antigenic determinants in dextran," *J. Exp. Med.* 142: 435-459.

(Continued)

*Primary Examiner* — Nita M Minnifield
*Assistant Examiner* — Brian J Gangle
(74) *Attorney, Agent, or Firm* — John P. White; Cooper & Dunham LLP

(57) ABSTRACT

This invention provides novel nitrocellulose-based or Hydrogel-based microarrays and methods of making and using them (1) to detect the presence of one or more agents in a sample, (2) to determine the amount of one or more agents in a sample, (3) to determine whether a subject is afflicted with a disorder, and (4) to determine whether an agent known to specifically bind to a first compound also specifically binds to a second compound. This invention also provides kits which comprise the instant microarrays. This invention further provides antibodies capable of specifically binding to a glycomer present both on the surface of a mammalian macrophage or intestinal epithelial cell, and on a bacterial cell. Finally, this invention provides diagnostic methods using the instant antibodies.

5 Claims, 31 Drawing Sheets

OTHER PUBLICATIONS

Cohen, S. et al. (2000) "Attenuated nontoxinogenic and nonencapsulated recombinant *Bacillus anthracis* spore vaccines protect against anthrax," *Infect. Immun.* 68: 4549-4558.

Cole, H.B. et al. (1984) "Differentiation of *Bacillus anthracis* and other *Bacillus* species by lectins," *J. Clin. Microbial.* 19: 48-53.

Deng, C. et al. (2001) DIMACS Workshop on Analysis of Gene Expression Data (DIMACS Center, Rutgers University; Piscataway, N.J.): abstract 3.

Deng, C. et al. (2002) Proceedings of IEEE International Joint Conference on Neural, Networks (Hawaii).

DeRisi, P. et al. (1996) "Use of a cDNA microarray to analyse gene expression patterns in human cancer," *Nat. Genet.* 14: 457-460.

DeRisi, J.L. et al. (1997) "Exploring the metabolic and genetic control of gene expression on a genomic scale," *Science* 278: 680-686.

Ehrhardt, R.O. et al. (1996) "Differential activation requirements of isotype-switched B cells," *Eur. J. Immunol*, 26: 1926-1934.

Eisen, M.B. et al. (1998) "Cluster analysis and display of genome-wide expression patterns," *Proc. Natl. Acad. Sci. USA* 95: 1.'14863-14868.

Ekins, R.P. (1989) "Multi-analyte immunoassay," *J. Pharm. & Biomed. Anal.* 7: 155-168.

Escuyer, V. & R.J. Collier (1991) "Anthrax protective antigen interacts with a specific receptor on the surface of CHO-K1 cells," *Infect, & Immun.* 59: 3381-3386.

Ezzell, J.W. et al. (1990) "Identification of *Bacillus anthracis* by using monoclonal antibody to cell wall galactose-N-acetylglucosamine polysaccharide," *J. Clin. Microbiol.* 28: 223-231.

Feizi, T. and R.W. Loveless (1996) "Carbohydrate recogniion by Mycoplasma pneumoniae and pathologic consequences," Am. J. Respir. Crit. Care Med. 154: S133-S136.

Feizi, T. (1998) "Carbohydrate recognition systems in innate immunity," in GLYCOIMMUNOLOGY 2 (ed. Axford) (Plenum Press: New York), 51-54.

Finne, J. et al. (1983) "Antigenic similarities between brain components and bacteria causing meningitis. *Implications for vaccine development and pathogenesis,*" Lancet. 2: 355-357.

Finne, J. et al. (1985) "Cleavage of the polysialosyl units of brain glycoproteins by a bacteriophage endosialidase. Involvement of a long oligosaccharide segment in molecular interactions of polysialic acid," *Jour. Biol. Chem.* 260: 1265-1270.

Fried. R. et al. (2001) "Online pattern recognition in intensive care medicine," *Proc. AMIA Sym.*, 184-188.

Friedlander, A.M. et al. (1999) "Anthrax vaccine: evidence for safety and efficacy against inhalational anthrax," *Jama* 282: 2104-2106.

Furey, T.S. et al. (2000) "Support vector machine classification and validation of cancer tissue samples using microarray expression data," *Bioinformatics* 16: 906-914.

Garcia-Patrone, M. et al. (1995) "A glycoprotein multimer from *Bacillus thuringiensis sporangia*: dissociation into subunits and sugar composition," *Mol Cell Biochem* 145: 29-37.

Ge, H., (2000) "UPA, a universal protein array system for quantitative detection of protein-protein, protein-DNA, protein-RNA and protein-ligand interactions," *Nucl. Aci. Res.*, 28(2): p. e3.

Gladstone, G.P. et al. (1970) "Effect of iron on the bactericidal proteins from rabbit polymorphonuclear leukocytes," *Nature* 227: 849-851.

Goodman, J.W. et al. (1967) "Studies on the relation of a prior immune response to immunogenicity," *Immunology* 13: 577-583.

Grifantini, R. et al. (2002) "Previously unrecognized vaccine candidates against group B *meningococcus* identified by DNA microarrays," *Nat. Biotechnol.* 20: 914-921.

Helgason, E. et al. (2000) "*Bacillus anthracis, Bacillus cereus*, and *Bacillus thuringiensis*—one species on the basis of genetic evidence," *Appl. Environ. Microbiol.* 66: 2627-2630.

Heidelberger, M. et al. (1967) "Cross-reactions of the group-specific polysaccharides of streptococcal groups B and G in anti-pneumococcal sera with especial reference to type 23 and its determinants," *J. Immunol.* 99: 794-796.

Heyer, L.J. et al. (1999) "Exploring expression data.: identification and analysis of coexpressed genes," *Genome Res.* 9:1106-1115.

Howe, C. et al. (1958) "Immunnochemical studies on blood groups," *J. Am. Chem. Soc.* 80: 6656.

Humphrey, J.H. et al. (1964) "Studies on globulin and antibody production in mice thymectomised at birth," *Immunology* 7: 419-439.

Ivars, F. et al. (1983) "Immune Response to Bacterial Dextrans: T Cell Control of Antibody Isotypes," *J. Exp. Med.* 158: 1498-1510.

Ivins, B. et al. (1995) "Experimental anthrax vaccines: efficacy of adjuvants combined with protective antigen against an aerosol *Bacillus anthracis* spore challenge in guinea pigs," *Vaccine* 13:1779-1784.

Jain, A.K. et al. (2000) "Statistical Pattern Recognition: A Review, *IEEE Transactions on Rattern Analysis and Machine Intelligence,*" 22; 4-37.

Jeanes, A. (1986) "Immunochemical and related interactions with dextrans reviewed in terms of improved structural information," *Mol. Immunol.* 23: 999-1028.

Kabat, E.A. et al. (1948) "Immunochemical studies on blood groups. VII. Chemical changes associated with destruction of blood group activity and enhancement of the type XIV cross-reactivity by partial hydrolysis of hog and human blood group A, B, and O, substances," *J. Exp. Med.* 88: 43-57.

Kabat, E.A. et al. (1980) "Human monoclonal macroglobulins with specificity for Klebsiella K polysaccharides that contain 3,4-pyruvylated-D- galactose and 4,6- pyruvylated-D-galaptose," *J. Exp. Med.* 152: 979-995.

Kabat, E.A. et al. (1982) "A monoclonal IgM lambda macroglobulin with specificity for facto-N- tetraose in a patient with bronchogenic carcinoma" *J. Immunol.* 128: 540-544.

Kabat, E.A. et al. (1984) "Immunochemical characterization of the specificities of two human monoclonal IgM's reacting with chondroitin sulfates," *Carbohydr. Res.* 130: 289-297.

Kabat, E.A. et al. (1986) "A human monoclonal macroglobulin with specificity for a(2—8)—linked poly-N-acetyl neuraminic acid, the capsular polysaccharide of group B meningococci and *Escherichia coli* K1, which crossreacts with polynucleotides and with denatured DNA," *J. Exp. Med.* 164: 642-654.

Kabat, E.A. et al. (1988) "The epitope associated with the binding of the capsular polysaccharide of the group B meningococcus and of *Escherichia coli* K1 to a human monclonal macroglobulin, IgM NOV," *J. Exp. Med.* 168: 699-711.

Kagnoff, M.F. et al. (1987) "T dependent induction of an IgA and IgM anti-polysaccharide response," *Adv. Exp. Med. & Biol.* 155-167.

Karlsson, K.A. et al. (1992) "Microbial interaction with animal cell surface carbohydrates," *APMIS. Suppl.* 27: 71-83.

Kim et al., (2000) "General nonlinear framework for the analysis of gene interaction via multivariate expression arrays," *J. Bio. Opt.* 5(4):411 424.

Krogh, A, et al. (2001) "Predicting transmembrane protein topology with a hidden Markov model: application to complete genomes," *J. Mol. Biol.* 305: 567-580.

Lai, E. et al. (1985) "Immunochemical studies of conjugates of isomaltosyl oligosaccharides to lipid: productiona nd characterization of mouse hybridoma antibodies specific for stearyl-isomaitosyl oligosaccharides," *Mol. Immunol.* 22: 1021-1037.

Lim, S. et al. (1985) "Isolation and characterization of a succinylated polysaccharide from the cell wall of *Micrococcus agilis*," *Microbios.* 44: 95-105.

Lincoln, R.E. et al. (1965) "Role of the lymphatics in the pathogenesis of anthrax," *J. Infect. Dis.* 115: 481-494.

Lueking, A., et al. (1999) "Protein microarrays for gene expression and antibody screening," *Anal. Bio.* 270(1): 103-11.

MacBeath, G. et al. (2000) "Printing proteins as microarrays for high-throughput function determination," *Science* 299: 1760-1763.

Makino, S. et al. (1989) "M. Molecular characterization and protein analysis of the cap region, which is essential for encapsulation in *Bacillus anthracis,*" *J. Bacteriol.* 171: 722-730.

Mandrell, R.E. et al. (1992) "Lopooligosaccharides (LOS) of some Haemophilus species mimic human glycosphingolipids, and some LOS are sialylated," *Infection & Immunity* 60: 1322-1328.

Mandrell, R.E. (1992) "Further antigenic similarities of Neisseria gonorrhoeae lipooligosaccharides and human glycosphingolipids," *Infection & Immunity* 60: 3017-3020.

Matsuda, T. et al. (1989) "Variable region cDNA sequences and antigen binding specificity of mouse monoclonal antibodies to isomaitosyl oligosaccharides coupled to proteins T-dependent analogues of α(1, 6)dextran," *J. Immunol.*, 142: 863-870.

McGhee, J.R. et al. (1989) "Regulation of IgA synthesis and immune response by T cells and interleukins," [Review] Jour. Clin. Immunol. 9: 175-199.

Mesnage, S. et al. (2000) "Bacterial SLH domain proteins are non-covalently anchored to the cell surface via a conserved mechanism involving wall polysaccharide pyruvylation," Embo. J. 19: 4473-4484.

Mestecky, J. (1987) "The common mucosal immune system and current strategies for induction of immune responses in external secretions," [Review] Jour. Clin. Immunol. 7: 265-276.

Michaels, G.S. et al. (1998) "Cluster analysis and data visualization of large-scale gene expression data," Pac Symp. Biocomput. 42-53.

Mock, M. et al. (2001) "Anthrax," Annu. Rev. Microbiol. 55: 647-671.

Mongini, P.K.A. et al. (1981) "T-cell regulation of IgG subclass antibody production in response to T- independent antigens," J. Exp. Med. 153: 1-12.

Mourez, M. et al. (2001) "Designing a polyvalent inhibitor of anthrax toxin," Nat. Biotechnol. 19: 958-961.

Nickerson, K-G. et al. (1993) "A monoclonal IgM kappa from a blood group B individual with specificity for alpha-galaotosyl epitopes on partially hydrolyzed blood group B substance," Carbohydr. Res. 243: 345-357.

Okinaka, R.T. et al. (1999) "Sequence and organization of pXO1, thea large Bacillus anthracis plasmid harboring the anthrax toxin genes," J. Bacteriol. 181: 6509-6515.

O'Shannessy, D. J. et al. (1984) "A novel procedure for labeling immunoglobulins by conjugation to oligosaccharide moieties," Immunol. Lett. 8: 273-277.

Peterson, L. (2002) "Factor analysis of cluster-specific gene expression levels from cDNA microarrays," Comput. Methods Programs Biomed. 69: 179.

Petosa, C. et al. (1997) "Crystal structure of the anthrax toxin protective antigen," Nature 385: 833-838.

Puziss, M. et al. (1963) "Large-scale production of protective antigen of Bacillus anthracis anaerobic cultures," Appl. Microbiol. 11: 330-334.

Ramaswamy, S. et al. (2001) "Multiclass cancer diagnosis using tumor gene expression signatures," Proc. Nat. Acad. Sci. U S A 98: 15149-15154.

Ramdas, L. et al. (2001) "Sources of nonlinearity in cDNA microarray expression measurements," Genome Biol. 2.

Ramsay, G., (1998) "DNA chips: state-of-the art," Nature Biotech. 16(1) : 40-44.

Ray, A. K. et al. (.1990) "Synthesis of di- and tri-saccharides related to the polysaccharide from Streptococcus pneumoniae type 23 and a study of their inhibition in the precipitin reaction," Carbohydr. Res. 197: 93-100.

Record, B.R. (1956) "Physicochemical examination of polyglutamic acid from Bacillus anthracis grown in vivo," Biochem. J. 63: 443-447.

Reuveny, S. et al. (2001) "Search for correlates of protective immunity conferred by anthrax vaccine," Infect. Immun. 69: 2888-2893.

Richards, J.C. et al. (1988) "Structure of the specific capsular polysaccharide of Streptococcus pneumoniae type 23F (American type 23)," Biochem. Cell Biol. 66: 758-771.

Robbins, J.B. et al. (1990) "Polysaccharide-protein conjugates: a generation of vaccines," J. Infct. Dis. 161: 821-832.

Roy, A. et al. (1984) "Structure of the capsular polysaccharide from Streptococcus pneumoniae type 23," Carbohydr. Res. 126: 271- 277.

Schena, M. (1995) "Quantitative monitoring of gene expression patterns with a complementary DNA microarray," Science 270:457-470.

Schena, M. et al. (1996) "Parallel human genome analysis: microarray-based expression monitoring of 1000 genes," Proc. Natl. Acad. Sci. U S A 93; 10614-10619.

Schneerson, R. et al. (1980) "Preparation, characterization, and immunogenicity of Haemophilus influenzae type b polysaccharide-protein conjugates" J. Exp. Med. 152: 351-376.

Schuch, R. et al. (2002) "A bacteriolytic agent that detects and kills Bacillus ahthracis," Nature 418: 884-889.

Sharon, J. et al. (1982) "Association constants of hybridoma antibodies specific for $\alpha(1-6)$ linked dextran determined by affinity electrophoresis," Mol. Immunol. 19: 389-397.

Shchelkunov, S.N. et al. (1996) "Analysis of the nucleotide sequence of 23.8 kbp from the left terminus of the genome of variola major virus strain India-1967," Virus Res. 40: 169-183.

Shlyakhov, E.N. et al. (1994) "Human live anthrax vaccines in the former USSR," Vaccine 12: 727-730.

Smith, H. et al. (1956) "The polysaccharide from Bacillus anthracis grown in vivo," Biochem. J. 63: 447-432.

Stepanov, A.V. et al. (.1996) "Development of novel vaccines against anthrax in man," J. Biotechnol, 44: 155-160.

Stoll, D. et al. (2002) "Protein microarray technology," Front Biosci. 7: C13-32.

Strange, R.E. et al, (1953) "Studies on a protective antigen produce in vitro from bacillus anthracis: Purification and chemisty of the antigen," Bri. J. Exp. Pathol. 35: 153-165.

Su, A. et al. (2001) "Molecular classification of human carcinomas by use of gene expression signatures," Cancer Res. 61: 7388-7393.

Tatusov, R.L. et al. (1997) "A genomic perspective on protein families," Science 278: 631-637.

Tonkinson, J.L. et al. (2002) "Nitrocellulose: a tried and true polymer finds utility as a post-genomic substrate," Front. Biosci. 7: C1-C12.

Tseng, G.C. et al. (2001) "Issues in cDNA microarray analysis: quality filtering, channel normalization, models of variations and assessment of gene effects" Nucleic Acids Res. 29: 2549-2557.

Turnbull, P.C. (1991) "Anthrax vaccines: past, present and future" Vaccine 9: 533-539.

Turnbull, P.C.B. (2000) "Current status of immunization against anthrax: old vaccines may be here to stay for a while," Corr. Opin. Infect. Dis. 13: 113-120.

van Steijn, A.M. et al. (1991) "Synthesis of a spacer-containing repeating unit of the capsular polysaccharide of Streptococcus pneumoniae type 23F," Carbohydr. Res. 211: 261-277.

Vapnik, V.N. (1999) "An overview of statistical learning theory," IEEE Tansactions on Neural Networks 10: 988-999.

Varki, A., (1993) "Biological roles of oligosaccharides: all of the theories are correct," Glycobiology, 3(2): 97-130.

Wang, D., et al., (1990) "Two families of monoclonal antibodies to $\alpha(1,6)$dextran, $V_H19.1.2$ and $V_H9.14.7$, show distinct patterns of $J_k$ and $J_H$ minigene usage and amino acid substitutions in CDR3," J. Immunol. 145: 3002-3010.

Wang, D., et al., (1991) "The repertoire of antibodies to a single antigenic determinant," Molecular Immunology 28: 1387-1397.

Wang, D. et al. (1994) "Reaction of germinal centers in the T-cell-independent response to the bacterial polysaccharide $\alpha(1-6)$dextran," Proc. Natl. Acad. Sci. USA 91: 2502-2506.

Wang, D. et al. (1996) "Carbohydrate Antigens (Polysaccharides), in Structure of Antigens," M.H.V.V. Regenmortal, Editor. (CRC Press: Inc.: New York)247-276.

Wang, D. et al. (2002) "Carbohydrate microarrays for the recognition of cross-reactive molecular markers of microbes and host cells," Nat Biotechhol 20: 275-281.

Weissman, I.L. et al. (1976) "Lymphoid tissue architecture. III. Germinal centers, T cells, and thymus-dependent vs thymus-independent antigens," Adv. Exp. Med. Biol. 66: 229-237.

White-Scharf, M.E. et al. (1978) "Evidence that L-rhamnose is the antigenic determinant of hyporesponsiveness of BALB/c mice to Klebsiella pneumoniae type 47," Infect. Immun. 22: 18-21.

Wyatt, R. et al. (1998) "The antigenic structure of the HIVgp120 envelope glycoprotein," Nature 393: 705-711.

Zareba, T.W. et al. (1997) "Binding of enterococci to extracellular matrix proteins," Adv. Exp. Med. Biol. 418: 721-723.

Zwartcuw, H.T. et al. (1956) "Polyglutamic acid from Bacillus anthracis grown in vivo: structure and aggressin activity" Biochem. J. 63: 437-442.

Office Action issued Sep. 9, 2005 in connection with U.S. Appl. No. 10/367,204 filed Feb. 14, 2003.

Office Action issued Dec. 23, 2005 in connection with U.S. Appl. No. 20/367,204 filed Feb. 14, 2003.

\* cited by examiner

FIGURE 8

Multiple antigenic stimulations     Complex Host Responses

*Life cycle of B. anthracis*

*Human immune system*

FIGURE 11

*HIV-1 infected* gp120 glycoprotein of HIV-1

*Normal* gp120 glycoprotein of HIV-1

Figure 17

A. A sugar-chip image

B. Antibody fingerprints

A tetra-saccharide unit of Pn 23-polysaccharide

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Primer

<400> SEQUENCE: 1 atggttctttt agctttctg                                            19

<210> SEQ ID NO 2
<211> LENGTH: 22
<212> TYPE: DNA
<213> ORGANISM: Artificial Sequence
<220> FEATURE:

```
<223> OTHER INFORMATION: Primer

<400> SEQUENCE: 2
ctatcctatt ccattaagat cc                                             22

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
gcgaagtaca agtgctgg                                                  18

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ctcctgttaa cgtgtaagtt                                                20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
tcaggcagaa gttaaacagg                                                20

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
gggaacaccg tcgaatag                                                  18

<210> SEQ ID NO 7
<211> LENGTH: 18
<212> TYPE: DNA
<213> ORGANISM: Artificial Sequence
<220> FEATURE:
<223> OTHER INFORMATION: Primer

<400> SEQUENCE: 7
tggcagctta tccgattg                                                  18

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
gcgtttaagt tctttgttga cg                                             22

<210> SEQ ID NO 9
```

<211> LENGTH: 21
<212> TYPE: DNA
<213> ORGANISM: Artificial Sequence
<220> FEATURE:
<223> OTHER INFORMATION: Primer

<400> SEQUENCE: 9
caagaaacaa ctgcacgtat c                    21

<210> SEQ ID NO 10
<211> LENGTH: 22
<212> TYPE: DNA
<213> ORGANISM: Artificial Sequence
<220> FEATURE:
<223> OTHER INFORMATION: Primer

<400> SEQUENCE: 10
caattcctcc gagtatctct tc                   22

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
tatcaagaat cagttagcg                       19

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ccgatactct atcctattcc a                    21

PNEUMOCOCCUS POLYSACCHARIDE-RELATED VACCINES

This application is a continuation and claims the benefit of U.S. Ser. No. 10/367,204, filed Feb. 14, 2003 now abandoned, the contents of which are hereby incorporated by reference into this application.

The invention described herein was made with Government support under grant number AI45326 from the National Institutes of Health. Accordingly, the United States Government has certain rights in this invention.

Throughout this application, various references are cited. Disclosure of these references in their entirety is hereby incorporated by reference into this application to more fully describe the state of the art to which this invention pertains.

BACKGROUND OF THE INVENTION

Genomics

The Human Genome Project is rapidly approaching its end: the complete mapping and sequencing of the human genome, and the identification of all genes therein. Emerging from this effort is a new generation of biotechnologies, collectively known as "functional genomics". These technologies, including DNA chips (1) and cDNA microarrays (2,3), make use of the sequence information and genetic materials provided by the human genome project, combine advanced laser and fluorescence sensor technology, and take advantage of computer-aided large-scale data management systems. Differing from classical molecular biology methods which focus on a specific gene or its product, these new approaches monitor the expression of genes on a genome-wide scale, and identify their characteristic overall patterns. The scope of biological investigation has therefore been expanded from the study of a single gene or protein to the study of numerous genes and/or proteins simultaneously.

Proteomics

Proteins are the final gene products, acting as fundamental elements of living organisms. However, the amount of mRNA expression does not always indicate the level of its encoded protein in a cell. The protein molecule has its own life span and kinetics of metabolism. There are specialized cellular machineries, such as the ubiquitin-dependent and -independent pathways of protein degradation, allowing rapid turnover of a protein when its function is no longer required. The fate of a newly synthesized protein is also significantly influenced by post-translational modifications, such as phosphorylation, glycosylation, acetylation or myristylation, at specific amino acid residues. Such molecular modifications are frequently regulated differentially and/or developmentally, establishing a specific function, or playing a structural role, for a given protein. Thus, it has been generally accepted that a better understanding of the genome's function will not be possible without protein analysis. Developing technologies for a genome-wide analysis of protein expression and post-translational modification represents a major challenge to the scientific community (4,5).

Glycomics

Carbohydrate-containing macromolecules are the secondary products of genes. Their synthesis requires multiple enzymatic reactions and many steps of intracellular trafficking, transportation and modification. Multiple genes contribute to the synthesis of cellular elements containing complex carbohydrates. "Glycomics", a new scientific discipline, has emerged to create a comprehensive understanding of the structure, function, synthesis and genetic regulation of cellular carbohydrate molecules.

Carbohydrates are abundant on cell surfaces, existing as either membrane-bound glycoconjugates or secreted substances. These molecules play fundamental structural and protective roles. They are also abundant intracellularly, and serve as an active and dynamic energy reservoir.

Recent studies further demonstrated that many important signaling and regulatory processes are mediated by the interaction of carbohydrate-ligands and their receptors (6,7). Abnormal expression of carbohydrate moieties may occur in cells that are undergoing malignant transformation. These moieties may therefore serve as molecular targets for tumor diagnosis or therapy.

The carbohydrate molecules of microorganisms are important in establishing the biological relationships of microbes and their hosts (7-9). These relationships especially include the host recognition of microorganisms and the induction of an immune response by a microbial antigen. The carbohydrate moieties of microbial antigens frequently serve as the key structures for immune recognition (10). Identifying such determinants is of fundamental importance for understanding the molecular mechanisms of host recognition and immune responses.

Existing Technologies

Technologies suitable for monitoring protein expression on a genome-wide scale and for characterizing a wide range of ligand-receptor interactions such as protein-protein reactions, carbohydrate-protein reactions and the interaction of synthetic small molecules and cellular components have yet to be developed. Current methods for specifically detecting and quantifying a protein or a microbial polysaccharide include antigen/antibody based-immunoassays. These assays include (a) classical direct immunoassays, such as immunodiffusion, immunoelectrophoresis, agglutination and immunoprecipitation assays, and (b) recently developed methods such as immunofluorescence, radioimmunoassay (RIA), enzyme-immunoassay (EIA) and western blot assays. These approaches exploit the specificity of antigen-antibody interactions. However, they are designed for analyzing only one agent at a time, and are therefore limited as to the number of molecules that can be analyzed in a single assay.

In sum, a single technology useful for the simultaneous study of numerous molecules, be they protein, carbohydrate or combinations thereof, is sorely needed to advance both proteomics and glycomics.

SUMMARY OF THE INVENTION

This invention provides six microarrays and two articles useful for making same. The first microarray comprises a nitrocellulose or Hydrogel support having affixed to its surface at discrete loci a plurality of compounds, wherein (a) at least one discrete locus is affixed a compound selected from the group consisting of a glycomer, an insoluble protein, a lectin and an antibody, and (b) the composition of compounds at each discrete locus differs from the composition of compounds at least one other discrete locus.

The second microarray comprises a plurality of nitrocellulose or Hydrogel supports, each support having one or a plurality of compounds affixed to its surface at a single discrete locus or a plurality of compounds affixed to its surface at discrete loci, wherein (a) at at least one discrete locus is affixed a compound selected from the group consisting of a glycomer, an insoluble protein, a lectin and an antibody, and (b) the composition of compounds at each discrete locus differs from the composition of compounds at least one other discrete locus.

The first article comprises a nitrocellulose or Hydrogel support having dextran affixed to its surface at discrete loci. In one embodiment the dextran is α(1,6) dextran.

The third microarray comprises the first article, wherein at least one compound is affixed to the dextran at each discrete locus, the composition of compounds at each discrete locus differing from the composition of compounds at least one other discrete locus.

The second article comprises a plurality of nitrocellulose or Hydrogel supports, each support having dextran affixed to its surface at one or more discrete loci. In one embodiment the dextran is α(1,6) dextran.

The fourth microarray comprises the second article, wherein at least one compound is affixed to the dextran at each discrete locus, the composition of compounds at each discrete locus differing from the composition of compounds at least one other discrete locus.

The fifth microarray comprises a nitrocellulose or Hydrogel support having affixed to its surface at discrete loci a plurality of compounds, wherein (a) at least one discrete locus is affixed a compound associated with *Bacillus anthracis* and selected from the group consisting of a glycomer and a protein, and (b) the composition of compounds at each discrete locus differs from the composition of compounds at least one other discrete locus.

The sixth microarray comprises a plurality of nitrocellulose or Hydrogel or Hydrogel supports, each support having one or a plurality of compounds affixed to its surface at a single discrete locus or a plurality of compounds affixed to its surface at discrete loci, wherein (a) at least one discrete locus is affixed a compound associated with *Bacillus anthracis* and selected from the group consisting of a glycomer and a protein, and (b) the composition of compounds at each discrete locus differs from the composition of compounds at least one other discrete locus.

This invention provides six methods for detecting the presence of agents in a sample. The first method is a method of detecting in a sample the presence of one or more agents which specifically bind to one or more known glycomers, which method comprises: (a) contacting the sample with the first or second microarray, wherein each known glycomer is affixed at least one discrete locus and wherein the contacting is performed under conditions which would permit an agent, if present in the sample, to specifically bind to its corresponding glycomer in the microarray; and (b) determining whether any known glycomer in the microarray has an agent specifically bound thereto, thereby detecting the presence of the one or more agents in the sample.

The second method is a method of detecting in a sample the presence of one or more agents which specifically bind to one or more known insoluble proteins, which method comprises: (a) contacting the sample with the first or second microarray, wherein each known insoluble protein is affixed at least one discrete locus and wherein the contacting is performed under conditions which would permit an agent, if present in the sample, to specifically bind to its corresponding insoluble protein in the microarray; and (b) determining whether any known insoluble protein in the microarray has an agent specifically bound thereto, thereby detecting the presence of the one or more agents in the sample.

The third method is a method of detecting in a sample the presence of one or more agents which specifically bind to one or more known antibodies or lectins, which method comprises: (a) contacting the sample with the first or second microarray, wherein each known antibody or lectin is affixed at least one discrete locus and wherein the contacting is performed under conditions which would permit an agent, if present in the sample, to specifically bind to its corresponding antibody or lectin in the microarray; and (b) determining whether any known antibody or lectin in the microarray has an agent specifically bound thereto, thereby detecting the presence of the one or more agents in the sample.

The fourth method is a method of detecting in a sample the presence of one or more agents associated with *Bacillus anthracis* which specifically bind to one or more glycomers, which method comprises: (a) contacting the sample with the fifth or sixth microarray, wherein each glycomer is affixed at least one discrete locus and wherein the contacting is performed under conditions which would permit an agent, if present in the sample, to specifically bind to its corresponding glycomer in the microarray; and (b) determining whether any glycomer in the microarray has an agent specifically bound thereto, thereby detecting the presence of the one or more agents in the sample.

The fifth method is a method of detecting in a sample the presence of one or more agents associated with *Bacillus anthracis* is which specifically bind to one or more proteins, which method comprises: (a) contacting the sample with the fifth or sixth microarray, wherein each protein is affixed at least one discrete locus and wherein the contacting is performed under conditions which would permit an agent, if present in the sample, to specifically bind to its corresponding protein in the microarray; and (b) determining whether any known protein in the microarray has an agent specifically bound thereto, thereby detecting the presence of the one or more agents in the sample.

The sixth method is a method of detecting in a sample the presence of one or more glycomers or proteins which specifically bind to one or more antibodies or lectins associated with *Bacillus anthracis*, which method comprises: (a) contacting the sample with the fifth or sixth microarray, wherein each antibody or lectin is affixed at least one discrete locus and wherein the contacting is performed under conditions which would permit an agent, if present in the sample, to specifically bind to its corresponding antibody or lectin in the microarray; and (b) determining whether any antibody or lectin in the microarray has an agent specifically bound thereto, thereby detecting the presence of the one or more agents in the sample.

This invention further provides three quantitative methods. The first method is a method of determining the amount of one or more agents in a sample, each of which specifically binds to one or more known glycomers, which method comprises: (a) contacting the sample with the first or second microarray, wherein each known glycomer is affixed at least one discrete locus, and wherein the contacting is performed under conditions which would permit an agent, if present in the sample, to specifically bind to its corresponding glycomer in the microarray; (b) for each known glycomer in the microarray, determining the amount of agent specifically bound thereto; and (c) comparing the amounts so determined to a known standard, thereby determining the amount of the one or more agents in the sample.

The second method is a method of determining the amount of one or more agents in a sample, each of which specifically binds to one or more known insoluble proteins, which method comprises: (a) contacting the sample with the first or second microarray, wherein each known insoluble protein is affixed at least one discrete locus, and wherein the contacting is performed under conditions which would permit an agent, if present in the sample, to specifically bind to its corresponding insoluble protein in the microarray; (b) for each known insoluble protein in the microarray, determining the amount of agent specifically bound thereto; and (c) comparing the amounts so determined to a known standard, thereby determining the amount of the one or more agents in the sample.

The third method is a method of determining the amount of one or more agents in a sample, each of which specifically binds to one or more known antibodies or lectins, which method comprises: (a) contacting the sample with the first or second microarray, wherein each known antibody or lectin is affixed at least one discrete locus, and wherein the contacting is performed under conditions which would permit an agent, if present in the sample, to specifically bind to its corresponding antibody or lectin in the microarray; (b) for each known antibody or lectin in the microarray, determining the amount of agent specifically bound thereto; and (c) comparing the amounts so determined to a known standard, thereby determining the amount of the one or more agents in the sample.

This invention further provides three diagnostic methods. The first method is a method of determining whether a subject is afflicted with a disorder characterized by the presence or absence in an afflicted subject of an agent which specifically binds to a known glycomer, which method comprises: (a) contacting a suitable sample from the subject with the first or second microarray, wherein the known glycomer is affixed at least one discrete locus and wherein the contacting is performed under conditions which would permit the agent, if present in the sample, to specifically bind to the known glycomer in the microarray; and (b) determining whether the known glycomer in the microarray has the agent specifically bound thereto, thereby determining whether the subject is afflicted with the disorder.

The second method is a method of determining whether a subject is afflicted with a disorder characterized by the presence or absence in an afflicted subject of an agent which specifically binds to a known insoluble protein, which method comprises: (a) contacting a suitable sample from the subject with the first or second microarray, wherein the known insoluble protein is affixed at least one discrete locus and wherein the contacting is performed under conditions which would permit the agent, if present in the sample, to specifically bind to the known insoluble protein in the microarray; and (b) determining whether the known insoluble protein in the microarray has the agent specifically bound thereto, thereby determining whether the subject is afflicted with the disorder.

The third method is a method of determining whether a subject is afflicted with a disorder characterized by the presence or absence in an afflicted subject of an agent which specifically binds to a known antibody or lectin, which method comprises: (a) contacting a suitable sample from the subject with the first or second microarray, wherein the known antibody or lectin is affixed at least one discrete locus and wherein the contacting is performed under conditions which would permit the agent, if present in the sample, to specifically bind to the known antibody or lectin in the microarray; and (b) determining whether the known antibody or lectin in the microarray has the agent specifically bound thereto, thereby determining whether the subject is afflicted with the disorder.

This invention further provides a method of determining whether an antibody known to specifically bind to a first glycomer also specifically binds to a second glycomer, which method comprises: (a) contacting the antibody with the first or second microarray, wherein a plurality of glycomers, other than the first glycomer, are affixed at discrete loci in the microarray, and wherein the contacting is performed under conditions which would permit the antibody to specifically bind to the first glycomer if it were present in the microarray; and (b) determining whether any of the glycomers in the microarray, other than the first glycomer, has the antibody specifically bound thereto, thereby determining whether the antibody also specifically binds to a second glycomer.

This invention further provides a method of determining whether an antibody known to specifically bind to a first insoluble protein also specifically binds to a second insoluble protein, which method comprises: (a) contacting the antibody with the first or second microarray, wherein a plurality of insoluble proteins, other than the first insoluble protein, are affixed at discrete loci in the microarray, and wherein the contacting is performed under conditions which would permit the antibody to specifically bind to the first insoluble protein if it were present in the microarray; and (b) determining whether any of the insoluble proteins in the microarray, other than the first insoluble protein, has the antibody specifically bound thereto, thereby determining whether the antibody also specifically binds to a second insoluble protein.

This invention further provides a method of making a microarray comprising a nitrocellulose or Hydrogel support having affixed to its surface at discrete loci a plurality of compounds, which method comprises contacting the nitrocellulose or Hydrogel support with the compounds under suitable conditions, whereby (a) at least one discrete locus is affixed a compound selected from the group consisting of a glycomer, an insoluble protein, a lectin and an antibody, and (b) the composition of compounds at each discrete locus differs from the composition of compounds at least one other discrete locus.

This invention further provides a method of making a microarray comprising a plurality of nitrocellulose or Hydrogel supports, each support having one or a plurality of compounds affixed to its surface at a single discrete locus or a plurality of compounds affixed to its surface at discrete loci, which method comprises contacting the nitrocellulose or Hydrogel supports with the compounds under suitable conditions, whereby (a) at least one discrete locus is affixed a compound selected from the group consisting of a glycomer, an insoluble protein, a lectin and an antibody, and (b) the composition of compounds at each discrete locus differs from the composition of compounds at least one other discrete locus.

This invention further provides a method of making the first article comprising contacting a nitrocellulose or Hydrogel support with dextran at discrete loci under suitable conditions.

This invention further provides a method of making the second article comprising contacting a plurality of nitrocellulose or Hydrogel supports with dextran, whereby each support has dextran affixed to its surface at one or more discrete loci.

This invention further provides six kits. The first kit comprises one of the instant microarrays and instructions for use. The second kit comprises one of the instant microarrays and a desiccant. The third kit comprises one of the instant microarrays immersed in an aqueous solution.

The fourth kit is a kit for practicing the first diagnostic method, which comprises: (a) a microarray comprising a nitrocellulose or Hydrogel support having affixed to its surface at discrete loci a plurality of compounds, wherein (i) at least one discrete locus is affixed the glycomer to which the agent present or absent in an afflicted subject specifically binds, and (ii) the composition of compounds at each discrete locus differs from the composition of compounds at least one other discrete locus; and (b) instructions for use.

The fifth kit is a kit for practicing the second diagnostic method, which comprises: (a) a microarray comprising a nitrocellulose or Hydrogel support having affixed to its surface at discrete loci a plurality of compounds, wherein (i) at least one discrete locus is affixed the insoluble protein to which the agent present or absent in an afflicted subject specifically binds, and (ii) the composition of compounds at each discrete locus differs from the composition of compounds at least one other discrete locus; and (b) instructions for use.

The sixth kit is a kit for practicing the third diagnostic method, which comprises: (a) a microarray comprising a nitrocellulose or Hydrogel support having affixed to its surface at discrete loci a plurality of compounds, wherein (i) at least one discrete locus is affixed the antibody or lectin to which the agent present or absent in an afflicted subject specifically binds, and (ii) the composition of compounds at each discrete locus differs from the composition of compounds at least one other discrete locus; and (b) instructions for use.

This invention further provides a first antibody capable of specifically binding to a glycomer present on the surface of a mammalian macrophage, which glycomer, or structural mimic thereof, is also endogenous to, and present on the surface of, a bacterial cell.

This invention further provides a second antibody capable of specifically binding to a glycomer present on the surface of a mammalian intestinal epithelial cell, which glycomer, or structural mimic thereof, is also endogenous to, and present on the surface of, a bacterial cell.

This invention further provides a method of determining whether a subject is afflicted with a disorder characterized by the presence of a glycomer on the surface of macrophages in an afflicted subject, which glycomer, or structural mimic thereof, is also endogenous to, and present on the surface of, a bacterial cell, comprising: (a) contacting a sample of the subject's macrophages with the first antibody; and (b) determining whether the antibody specifically binds to the macrophages in the sample, such binding indicating that the subject is afflicted with the disorder.

Finally, this invention provides a method of determining whether a subject is afflicted with a disorder characterized by the presence of a glycomer on the surface of intestinal epithelial cells in an afflicted subject, which glycomer, or structural mimic thereof, is also endogenous to, and present on the surface of, a bacterial cell, comprising: (a) contacting a sample of the subject's intestinal epithelial cells with the second antibody; and (b) determining whether the antibody specifically binds to the intestinal epithelial cells in the sample, such binding indicating that the subject is afflicted with the disorder.

Figure 1:
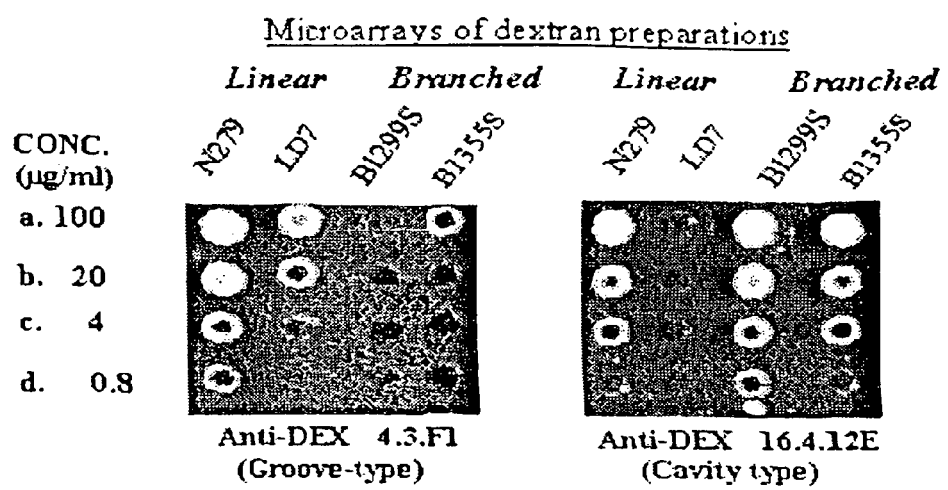
FIG. 1

This Figure shows a carbohydrate microarray and its application in characterizing the epitope-binding specificity of monoclonal antibodies ("mAb"). Dextran preparations of defined structural characteristics, including N279, LD7, B1299S and B1355S, were immobilized on a nitrocellulose-coated micro-glass slide in serial dilutions and stained with anti-$\alpha$(1,6)dextran antibodies. These antibodies were either a groove-type antibody, i.e., 4.3.F1, or a cavity-type antibody, i.e., 16.4.12E, and were conjugated with fluorescence. Their distinct epitope-binding specificities were visualized by scanning the carbohydrate microarray using a GMS 418 microarray scanner.

FIG. 2

This Figure shows an antigen-based microarray and its application in studying the cross-reactivity of monoclonal antibodies. Forty-nine distinct antigen preparations, including microbial polysaccharides, blood group substances and other glycoconjugates, were arrayed on slides and incubated with fluorescence-labeled mAbs. FIG. 2A: anti-DEX 4.3.F1; FIG. 2B: anti-DEX 16.4.12E. Intensity values of cross-reacting spots were compared with those of specific binding to $\alpha$(1,6)dextran N279. N279 was applied as a series of 1:5 dilutions of a 100 µg/ml solution (a). Other antigens were applied as 500 µg/ml. Identical antigens are arrayed in FIG. 2A and FIG. 2B.

FIG. 3

This Figure shows the detection of a cell population in the small intestine of an adult mouse by a groove-type anti-$\alpha$(1,6)dextran antibody 4.3.F1 (IgG3), which showed cross-reactivity to a chondroitin sulfate B preparation. The cryostat sections of small intestine were stained either by mAb 4.3.F1 (IgG3) or by an IgG3 isotype control mAb obtained from BD PharMingen. The two mAbs were fluorescent conjugates. Sections were co-stained with DAPI for the cell nucleus to visualize the overall tissue structure. The 4.3.F1-positive cells were seen in the lamina propria of the small intestine. FIGS. 3A-3D: mAb 4.3.F1; FIGS. 3E-3H: isotype control.

FIG. 4

This Figure shows that groove-type and cavity-type anti-$\alpha$(1,6)dextran monoclonal antibodies recognize distinct cellular markers: a groove-type mAb 45.21.1 (IgA) identifies a cell population in the lamina propria of the small intestine (FIGS. 4C and 4F), and a cavity-type mAb 16.4.12E (IgA) stains the epithelial cells in the crypts of the small intestine (FIGS. 4B and 4E). An IgA isotype control mAb purchased from BD PharMingen was applied as a background control (FIGS. 4A and 4D).

FIG. 5

This Figure shows the recognition of a cell population in the human small intestinal tissue using anti-$\alpha$(1,6)dextran antibodies. The intestinal section of a normal (FIGS. 5A and 5B) and of a celiac individual (FIGS. 5C and 5D) were stained with the fluorescence-conjugate of mAb 16.4.12E (FIGS. 5B and 5D) and co-stained with DAPI to reveal the intestinal structures (FIGS. 5A and 5C).

FIG. 6

This Figure shows the immobilization of polysaccharides on a nitrocellulose-coated glass slide. Panel A: Image of the carbohydrate microarray (microarrays of dextrans and inulin) spots before and after washing. Panel B: Quantitative illustration of the relation of fluorescence intensity and the concentration of printed carbohydrate microarrays before and after washing. Fluorescent conjugates of dextrans or inulin were dissolved in saline (0.9% NaCl) and spotted at an initial concentration of 10 mg/ml and then diluted in serial dilutions of 1:5. The microarray slides were scanned before and after washing. The data of six repeats of the same experiment is statistically analyzed and presented. Legend: ■: 2000 k; ▲: 70 k; ●: 20 k; ♦: Inulin.

FIG. 7

This Figure shows the immunological characterization of surface-immobilized dextran molecules. Panel A: Microarray binding curves of a groove-type anti-Dex 4.3F1 (IgG3/Kappa) and a cavity-type anti-dextran 16.4.12E (IgA/Kappa) to dextran molecules of distinct structure. Dextran molecules were printed with an initial concentration of 0.1 mg/ml and diluted by a 1:5 series titration. The printed arrays were washed to remove unbound antigens and then stained with biotinylated anti-dextran, either 4.3F1 or 16.4.12E, at a concentration of 1 µg/ml, and then stained with Cy3-streptavidin at 1:500 dilutions. The readout of the experiment (i.e., fluorescent intensity of the microspot) reflects the amounts of antigen immobilized and epitopes displayed for antibody recognition. The cavity-type mAb 16.4.12E bound to N279 and B12995, but not LD7. By contrast, the groove-type mAb 4.3F1 bound to the dextran preparations N279 and LD7, but bound poorly to B1299S. Panel B: ELISA binding curve of anti-Dex 4.3F1 and 16.4.12E. Dextran preparations were coated on an ELISA plate at an initial concentration of 10 μg/ml and then diluted by a 1:5 series titration in 0.02 M borate-buffered saline, pH 8.0. The antigen-coated plates were incubated with biotinylated anti-dextrans at a concentration of 1 μg/ml. The bound antibodies were revealed with an alkaline phosphatase (AP)-streptavidin conjugate and AP substrate. Legend: ♦: N279; □: LD7; ▲: B-1299S. Left Panel: 4.3F1 (Groove-type); Right Panel: 16.4.12 (Cavity-Type).

FIG. 8

*Bacillus anthracis* exposes and releases a number of antigens of distinct structural characteristics to trigger and induce a comprehensive picture of a host response. Left: Schematic of the life cycle of *Bacillus anthracis*. Dormant spores present in vitro are highly resistant to adverse environmental conditions. In a suitable environment, spores establish vegetative growth. In an early infection, these infective particles are ingested by the phagocytic cells and accumulate in the local lymphoid tissue. Some may survive from the phagocytes and initiate their germination and vegetative growth. The vegetative form of the bacteria is square-ended and capsulated. In the late infection, they multiply rapidly, express their virulence factors to kill the host and develop to the stage of resporulation in vivo. Antigens & toxins: Vegetative *bacillus* releases multiple factors, such as toxins, protein factors, and soluble polysaccharides (1-3,4 of the Third Series of Experiments). The protein fractions, such as the protective antigen, named PA, can provide strong protection to the immunized animals. It is now well understood that PA is an integrated component of the lethal toxin of *Bacillus anthracis*. It binds to a specific cellular receptor and forms toxic, cell bound complexes with edema factor (EF) and lethal factor (LF) (1-3 of the Third Series of Experiments). Neutralization antibodies to PA or a polyvalent factor that inhibits the formation of the complex may protect animals from the lethal attack by the toxin (5 of the Third Series of Experiments). A considerable amount of polysaccharides are also present in the culture media of the growing bacteria. Its sugar compositions are similar (if not identical) to the cell wall Gal-NAG polysaccharide. Right: An outline of the human immune system. The native immunity forms the first line of a host anti-infection response. These include macrophages, natural killer cells (NK), pre-existing "natural antibody" of IgM isotype and perhaps a specific B cell lineage, the B-1 cells, TCR γδ T cells, and other cells. In the anthrax infection, the phagocytic cells may play multiple roles in the host-microbe interaction. These may include both protective and pathogenic effects (see below for details). The acquired immune system includes B cells (the bone marrow derived B cells, or B-2 cells) and T cells (the thymus derived TCR αβ T cells). B cells mount a specific antibody response to a microbial antigen, either a independent antigen, such as an anthrax polysaccharide, or a T-dependent antigen, for example the protective antigen (PA) of *B. anthracis*; specific T cells can be activated by a TD protein antigen to regulate a B cell responses, either positively (T helper, Th1 and Th2) or negatively. There is also activation of specific cytotoxic T cells (Tc), which can kill the cells that express a foreign antigen. Many host cells, including immune cells and non-immune cell types, may produce cytokines or other inflammation factors to assist a host anti-infection response.

FIG. 9

This Figure shows a simple and efficient procedure for producing a carbohydrate microarray. Microspotting: Carbohydrate antigens were printed using Cartesian Technologies' PIXSYS 5500C (Irvine, Calif.) with STEALTH 3 pins. Supporting substrate: FAST Slides (Industrial partner A, Schleicher & Schuell, Keene, N.H.). The printed carbohydrate microarrays were air dried and stored at room temperature without desiccant before application. Immuno-staining: Immediately before use, the microarrays were rinsed with phosphate-buffered saline (PBS). The staining procedure utilized is essentially identical to regular immunofluorescent staining of tissue sections. Microarray-scanning: A ScanArray 5000 Standard Biochip Scanning System and its QuantArray software (Packard Biochip Technologies, Inc.) were applied for scanning and data capturing.

FIG. 10

This Figure shows a schematic of the 8-chamber sub-arrays.

FIG. 11

This Figure shows probing of the repertoires of human serum antibodies using Antigen Chip 4000. Left: HIV negative normal serum. Right: Serum of an HIV-1 infected individual. For each microarray analysis, 10 ml of serum were applied on an antigen chip at 1:10 dilutions. Anti-human antibodies with distinct fluorescent tags were applied to recognize and quantify the bound human IgG, IgM and IgA. In this Figure, human IgG was stained in Red/Cy5 and human IgM in Green/Cy3. The two images of contrasting colors were overlaid. IgA human antibodies were detected on the same chip with an anti-human IgA$^{FITC}$ (data was not shown).

FIG. 12

This Figure shows the scanning of human antibodies specific for a large panel of HIV proteins using a protein-based microarray biochip. Serum specimens of four normal individuals and six AIDS patients were characterized by a protein biochip that displays a large panel of HIV-1 proteins. Each preparation was printed four times on the same biochip. For each assay, 10 μl of serum were applied at 1:10 dilutions on a single chip. Human IgG that was captured by the immobilized antigens was recognized and quantified by a Cy3-labeled second antibody. Data of each group, normal and HIV-infected individuals, were statistically analyzed. Results were presented as the mean value of the ratio of fluorescent intensity over the background of given microspots (Histogram). Their standard division was also shown. Significant variations that were observed in the HIV-1 infected group may reflect the diversity of the HIV-1 specific antibody responses, as well as the level of antigenic cross-reactivities of HIV-1 proteins that were expressed by different clades or strains of HIV-1 virus.

FIG. 13

This Figure shows a schematic of a hypothetical structural and immunological relationships of the type II backbone structure of blood group substances, type XIV pneumococcal polysaccharide and the cell wall Gal-NAG polysaccharide.

FIG. 14

This Figure shows a carbohydrate microarray characterization of human and murine antibodies. Forty-eight distinct antigen preparations were arrayed on slides at antigen concentrations of 0.5 mg/ml and 0.02 mg/ml. They were incubated with combined human serum specimens at a concentration equivalent to 1:100 dilutions of each specimen or with binotinylated mouse monoclonal antibodies at 1 mg/ml. The human IgM captured by microarrays was visualized using an anti-human IgM-AP conjugate and the color developed using Vector Red. The human IgG anti-carbohydrates were detected using a biotinylated anti-human IgG. A Cy3-Streptoavidin conjugate was then applied to visualize the human IgG or murine monoclonal antibodies bound on microarray. The readout of the experiment, i.e., fluorescent intensity of the microspot, reflects the amounts of antigen immobilized and epitopes displayed for antibody recognition. Data of four repeats of microarray staining are summarized in Table 2.

FIG. 15

This Figure shows the prediction of protein structure using TMHMM version 2.0 (55 of the Third Series of Experiments): PX01-54 of *B. anthracis* encodes a S-layer protein, a novel molecular target for anthrax diagnosis and vaccination.

FIG. 16

This Figure shows biochip detection of human antibody reactivities to either anthrax polysaccharide or Pneumococcus type XIV polysaccharide in mixed human serum specimen which confirms that these antigen preparations are applicable for producing diagnostic microarrays.

FIG. 17

This Figure shows a schematic of diagnosis and surveillance of emerging infectious diseases using antigen arrays. An emerging infection may attack human as well as animal populations. Detecting specific antibodies in their bodily fluids using antigen microarrays is a powerful means for the diagnosis and surveillance of emerging infectious diseases. Left: schematic of the life cycle of *Bacillus anthracis*; Right: host antibodies elicited by an infection are important molecular targets for the diagnosis and surveillance of emerging infectious diseases.

FIG. 18

This Figure shows long-lasting antigenic reactivities of protein microarrays in some but not all preparations.

FIG. 19

This Figure shows that clustering analysis identified reproducible global pattern of antigenic reactivities on biochips.

FIG. 20

This Figure shows that purified GFPuv protein is stably immobilized on the nitrocellulose-coated slide (upper row) but is less stable on a poly-Lys treated DNA ready slide (bottom row). A preparation of purified GFPuv was spotted on slide at 0.5 mg/ml (left side) and 0.05 mg/ml (right side). Scanning was performed 1) at the same day after spotting; 2) after overnight air-drying the slide; and 3) after washing the slide extensively in a buffer containing 0.1% Tween 20 1×PBS.

FIG. 21

This Figure shows the structure of PA and its four domains: PA is a long, flat molecule of dimensions 100×~50×30 Å. and is composed of four domains[46]. Domain 1 (residues 1-258) comprises a b-sandwich with jelly-roll topology, several small helices, and a pair of adjacent calcium ions coordinated by residues in a variant of the EF-hand motif. Domain 2 (residues 259-487) has a b-barrel core with modified Greek-key topology and elaborate excursions, including a large flexible loop between strands 2b2 and 2b3 that is implicated in membrane insertion. Domain 3 (residues 488-595) has a four-stranded mixed b-sheet, two smaller sheets and four helices; it adopts the same fold as ferredoxins and resembles domain A of toxic-shock-syndrome toxin-1. Domain 4 (residues 596-735) has an initial hairpin and helix, followed by a b-sandwich with an immunoglobulin-like fold. Domains 1, 2 and 3 are intimately associated, but domain 4 has limited contact with the other. 3 domains. D1 is the N-terminal domain, contains two calcium ions and the cleavage site for activating proteases. D2 contains a large flexible loop for membrane insertion. D3 is a small domain of unknown function. D4 is the C-terminal receptor-binding domain. (Domain description from Petosa et al. *Nature Vol.* 305 (1997); image generated from the structure of protective antigen using NCBI's Cn3D version 4.0).

FIG. 22

This Figure shows a schematic of a molecular approach to construct GFP fusion proteins of PA and its derivatives. Primers for PCR reactions are designed based on sequence information of each domain target. Restriction sites are selected to avoid digesting the PA chains or its domains.

Following are primer sequences of PA derived portion: Integral PA (nt bases 143,799-146,073): 5' ATGGTTCTT-TAGCTTTCTG (19 mer, Start: 143,409) (SEQ ID NO: 1); 3' CCTAGAATTACCTTATCCTATC (22 mer, Stop: 146,085) (SEQ ID NO: 2). P63 (nt bases 144,376-146,070): 5' GCGAAGTACAAGTGCTGG (18 mer, Start: 144,363) (SEQ ID NO: 3); 3' TTGAATGTGCAATTGTCCTC (20 mer, Stop: 146,321) (SEQ ID NO: 4). PA Domain 1 (nt bases 143,866-144,639): 5' TCAGGCAGAAGTTAAACAGG (20 mer, Start: 143,859) (SEQ ID NO: 5); 3' GATAAGCTGCCA-CAAGGG (18 mer, Stop: 144,643) (SEQ ID NO: 6). PA Domain 2 (nt bases 144,640-145,326): 5' TGGCAGCT-TATCCGATTG (18 mer, Start: 144,632) (SEQ ID NO: 7); 3' GCAGTTGTTTCTTGAATTTGCG (22 mer, Stop: 145,331) (SEQ ID NO: 8). PA Domain 3 (nt bases 145,327-145,650): 5' CAAGAAACAACTGCACGTATC (21 mer, Start: 145,318) (SEQ ID NO: 9); 3' CTTCTCTATGAGCCTCCTTAAC (22 mer, Stop: 145,720) (SEQ ID NO: 10). PA Domain 4 (nt bases 145,651-146,070): 5' TATCAAGAATCA GTTAGCG (19 mer, Start: 145,548) (SEQ ID NO: 11); 3' ACCTTATC-CTATCTCATAGCC (21 mer, Stop: 146,076) (SEQ ID NO: 12).

FIG. 23A

This Figure shows lectin staining of α-Gal specific oligosaccharides displayed by the neoglycoconjugates.

FIG. 23B

This Figure shows that α-Gal-sugar chains are displayed by the PAGE-based neoglycoconjugates and are detected by the human anti-α-Gal antibodies.

FIG. 24

This Figure shows a carbohydrate microarray characterization of antibody fingerprints in rabbit serum specimens. Panel A: A microarray staining of rabbit anti-anthrax spore antiserum revealed a broad spectrum of antibody specificities; Panel B: Clustering analysis of antibody profiles of an unimmunized (subject 1) and two anthrax spore-immunized rabbit antibodies, one obtained from an U.S. company (subject 2) and another from an U.K.-based company (subject 3).

FIG. 25

This Figure shows dimension reduction analysis to reveal anthrax specific anti-carbohydrate activities. Panel A: Anti-anthrax antiserum-U.S.; Panel B: Anti-anthrax anti-serum-U.K. Slashed open circles represent the diagnostic index of antigens relevant to *B. anthracis*, including the anthrax cell-wall polysaccharide, Pn14-polysaccharide which is cross-reactive to anthrax cell-wall polysaccharide, anthrax protective protein (PA) and the Pn23-polysaccharide, which is proposed by this investigation as a cross-reactive antigen to the sugar structure(s) of anthrax spores. Black spots represent the diagnostic index of antigens that are not relevant to *B. anthracis* based on our current understanding and available information. The two lines are set to 2 times the standard deviation from the mean value of the corresponding chip. Spots distributed outside the lines are statistically significant. The only slashed open circle outside the green lines is Pn23 polysaccharide, which is commonly seen in the two anti-anthrax spore responses from different subjects. The dimension reduction analysis algorithm was developed in our laboratory. In principle, we applied the microarray signals detected in non-immunized/uninfected serum specimens as the "filters" to subtract the microarray signals that exist in both the experimental condition and the control condition.

FIG. 26

This Figure shows ELISA confirmation of the cross-reactivities of rabbit anti-anthrax spore antibodies to Pn23-polysaccharide but not Pneumococcus type 14 (Pn14). Polysaccharides were coated on an ELISA plate at concentration of 10 μg/ml in 0.02M BBS. The initial concentration of rabbit sera were 1/250 with serial 1:5 dilution titrated in 2% NBC-PBS/tween20. Panel A: ELISA binding curves of non-immunized rabbit serum (rabbit-D); and Panel B: anthrax spore immunized rabbit serum (rabbit-G). Panel C: ELISA value for anti-anthrax spore antibodies of rabbit serum at OD 405 nm at serum dilution of 1/250.

FIG. 27

This Figure shows the structural unit of Pn23 polysaccharide (from van Steijn et al.[41]). Glcp represents the p ring form of glucose, Galp represents the p ring form of galactose, and Rhap represents the p ring form of 6-deoxy-mannose. Linkages between the sugars have two possible anomeric designators: a (alpha) or b (beta), and are indicated in the structure. D or L stands for two possible absolute designators. The numbers presented between the two linked sugars specify which carbon molecules form the disaccharide bonds. Since the two numbers are presented between the two sugars that are bonded, the number that is closest to the respective sugar represents the carbon number of the sugar that forms the linkage. For example, in the adjacent molecule, carbon 1 from the glucose molecule is linked to carbon 4 of the galactose molecule.

FIG. 28

This Figure shows the antigenic cross-reactivities of anti-anthrax spore antibodies to Pn23 polysaccharide that were substantially reduced by pre-absorption of the rabbit anti-sera with the spores of *B. cereus* 4342.

FIG. 29

This Figure shows lectin staining of α-Gal specific oligosaccharides displayed by the neoglycoconjugates.

FIG. 30

This Figure shows non-covalent absorption to immobilize proteins and polysaccharides on a nitrocellulose-coated microchip.

DETAILED DESCRIPTION OF THE INVENTION

Definitions

As used in this application, except as otherwise expressly provided herein, each of the following terms shall have the meaning set forth below.

"Affixed" shall mean attached by any means. In one embodiment, affixed shall mean attached by a covalent bond. In another embodiment, affixed shall mean attached non-covalently.

"Agent" shall mean any chemical entity, including, without limitation, a glycomer, a protein, an antibody, a lectin, a nucleic acid, a small molecule, and any combination thereof.

"Antibody" shall mean (a) an immunoglobulin molecule comprising two heavy chains and two light chains and which recognizes an antigen; (b) polyclonal and monoclonal immunoglobulin molecules; and (c) monovalent and divalent fragments thereof. Immunoglobulin molecules may derive from any of the commonly known classes, including but not limited to IgA, secretory IgA, IgG and IgM. IgG subclasses are also well known to those in the art and include, but are not limited to, human IgG1, IgG2, IgG3 and IgG4. Antibodies can be both naturally occurring and non-naturally occurring. Furthermore, antibodies include chimeric antibodies, wholly synthetic antibodies, single chain antibodies, and fragments thereof. Antibodies may be human or nonhuman. Nonhuman antibodies may be humanized by recombinant methods to reduce their immunogenicity in man.

"Aqueous solution" shall mean any solution in which water is a solvent. Examples of aqueous solutions include water and water-based buffer solutions.

"Associated with *Bacillus anthracis*" shall mean physically derived from *Bacillus anthracis*, present on or within *Bacillus anthracis*, a derivative or degradation product of *Bacillus anthracis* or a portion thereof, and/or able to bind to any or all of the forementioned. Examples of agents associated with *Bacillus anthracis* include, without limitation, any anti-*Bacillus anthracis* antibody and an immunogenic oligosaccharide present on the surface of *Bacillus anthracis*.

"Complex carbohydrate" shall mean a carbohydrate polymer comprising more than two types of saccharide monomer units. Examples of complex carbohydrates include blood group substances such as Lewis X and Lewis Y.

"Composition of compounds" at a discrete locus shall mean the identity of the one or more compounds at that locus. For example, if locus 1 has compounds A and B, and locus has compounds A and C, then the composition of compounds at locus 1 differs from that at locus 2.

"Compound" shall mean any molecule. Compounds include, but are not limited to, proteins, nucleic acids, glycomers, lipids and small molecules.

"Dextran" shall mean a branched polymer of glucose consisting mainly of α(1,6)-glycosidic linkages.

"Discrete locus" shall mean a point, region or area for the affixation of a compound which does not overlap with another such point, region or area, and which may further be separated from another such point, region or area by physical space.

"Glycomer" shall mean any carbohydrate-containing moiety. Glycomers include, without limitation, (a) complex carbohydrates, (b) polysaccharides, (c) oligosaccharides and (d) glycoconjugates. "Glycoconjugates" include, without limitation, glycoproteins, glycolipids and glycopolymers. In one embodiment of the glycomer, the carbohydrate moiety thereof is conjugated, either covalently or noncovalently, to polyacrylamide.

"Insoluble protein" shall mean any protein which does not solubilize in aqueous solution. Examples of insoluble proteins include trans-membrane proteins.

"Lectin" shall mean a protein that is capable of agglutinating erythrocytes, binding sugars, and/or stimulating mitosis. Examples of lectins include concavalin A.

"Microarray" shall mean (a) a solid support having one or more compounds affixed to its surface at discrete loci, or (b) a plurality of solid supports, each support having one or a plurality of compounds affixed to its surface at discrete loci. The instant microarrays can contain all possible permutations of compounds within the parameters of this invention. For example, the instant microarray can be an all-glycomer microarray, an all-insoluble protein microarray, an all-antibody microarray, a disease-specific microarray, a species-specific microarray, or a tissue-specific microarray.

"Nitrocellulose or Hydrogel support" shall mean any solid support having nitrocellulose or Hydrogel affixed to its surface. Nitrocellulose or Hydrogel supports include, without limitation, nitrocellulose-coated or Hydrogel-coated chips (e.g. silicone chips), slides (e.g. glass slides), filters, plates and beads.

"Polysaccharide" shall mean a carbohydrate polymer comprising either one or two types of saccharide monomer units. Examples of polysaccharides include bacterial cell surface carbohydrates.

"Sample", when used in connection with the instant methods, includes, but is not limited to, any body tissue, skin lesion, blood, serum, plasma, cerebrospinal fluid, lymphocyte, urine, exudate, or supernatant from a cell culture.

"Specifically bind" shall mean the binding of a first entity to a second entity based on complementarity between the three-dimensional structures of each. In one embodiment, specific binding occurs with a $K_D$ of less than $10^{-5}$. In another embodiment, specific binding occurs with a $K_D$ of less than $10^{-8}$. In a further embodiment, specific binding occurs with a $K_D$ of less than $10^{-11}$.

"Subject" shall mean any organism including, without limitation, a mouse, a rat, a dog, a guinea pig, a ferret, a rabbit and a primate. In the preferred embodiment, the subject is a human being.

Embodiments of the Invention

This invention provides six microarrays and two articles useful for making same. The first microarray comprises a nitrocellulose or Hydrogel support having affixed to its surface at discrete loci a plurality of compounds, wherein (a) at least one discrete locus is affixed a compound selected from the group consisting of a glycomer, an insoluble protein, a lectin and an antibody, and (b) the composition of compounds at each discrete locus differs from the composition of compounds at least one other discrete locus.

The second microarray comprises a plurality of nitrocellulose or Hydrogel supports, each support having one or a plurality of compounds affixed to its surface at a single discrete locus or a plurality of compounds affixed to its surface at discrete loci, wherein (a) at at least one discrete locus is affixed a compound selected from the group consisting of a glycomer, an insoluble protein, a lectin and an antibody, and (b) the composition of compounds at each discrete locus differs from the composition of compounds at least one other discrete locus.

The first article comprises a nitrocellulose or Hydrogel support having dextran affixed to its surface at discrete loci. In one embodiment the dextran is α(1,6) dextran.

The third microarray comprises the first article, wherein at least one compound is affixed to the dextran at each discrete locus, the composition of compounds at each discrete locus differing from the composition of compounds at least one other discrete locus.

The second article comprises a plurality of nitrocellulose or Hydrogel supports, each support having dextran affixed to its surface at one or more discrete loci. In one embodiment the dextran is α(1,6) dextran.

The fourth microarray comprises the second article, wherein at least one compound is affixed to the dextran at each discrete locus, the composition of compounds at each discrete locus differing from the composition of compounds at least one other discrete locus.

In one embodiment of the first and third microarrays, the nitrocellulose or Hydrogel support is selected from the group consisting of a chip, a slide, a filter, and a plate. In one embodiment of the second and fourth microarrays, the nitrocellulose or Hydrogel support is selected from the group consisting of a chip, a slide, a filter, a plate, and a bead.

In one embodiment of the above microarrays, the number of discrete loci is at least 100. In another embodiment, the number of discrete loci is at least 1000. In a further embodiment, the number of discrete loci is at least 10,000. In a further embodiment, the number of discrete loci is at least 50,000.

In one embodiment of the first and second microarrays, a glycomer is affixed at least one locus. In another embodiment, an insoluble protein is affixed at least one locus. In another embodiment, a lectin is affixed at at least one locus. In a further embodiment, an antibody is affixed at least one locus. In a further embodiment, the microarray has affixed to its surface two or more compounds selected from the group consisting of a glycomer, an insoluble protein, a lectin and an antibody. In a further embodiment, the microarray has further affixed to its surface a compound selected from the group consisting of a soluble protein, a nucleic acid and a small molecule.

In one embodiment of the third and fourth microarrays, a glycomer is affixed to the dextran at least one locus. In another embodiment, an insoluble protein is affixed to the dextran at least one locus. In another embodiment, a lectin is affixed to the dextran at least one locus. In a further embodiment, an antibody is affixed to the dextran at least one locus. In another embodiment, the microarray has affixed to the dextran two or more compounds selected from the group consisting of a glycomer, an insoluble protein, a lectin and an antibody. In another embodiment, the microarray has affixed to its surface a compound selected from the group consisting of a soluble protein, a nucleic acid and a small molecule.

In one embodiment of the instant microarrays, at each locus is affixed only one compound. In another embodiment, at least one locus is affixed a plurality of compounds.

This invention provides six methods for detecting the presence of agents in a sample. The first method is a method of detecting in a sample the presence of one or more agents which specifically bind to one or more known glycomers, which method comprises: (a) contacting the sample with the first or second microarray, wherein each known glycomer is affixed at least one discrete locus and wherein the contacting is performed under conditions which would permit an agent, if present in the sample, to specifically bind to its corresponding glycomer in the microarray; and (b) determining whether any known glycomer in the microarray has an agent specifically bound thereto, thereby detecting the presence of the one or more agents in the sample.

The second method is a method of detecting in a sample the presence of one or more agents which specifically bind to one or more known insoluble proteins, which method comprises: (a) contacting the sample with the first or second microarray, wherein each known insoluble protein is affixed at least one discrete locus and wherein the contacting is performed under conditions which would permit an agent, if present in the sample, to specifically bind to its corresponding insoluble protein in the microarray; and (b) determining whether any'known insoluble protein in the microarray has an agent specifically bound thereto, thereby detecting the presence of the one or more agents in the sample.

The third method is a method of detecting in a sample the presence of one or more agents which specifically bind to one or more known antibodies or lectins, which method comprises: (a) contacting the sample with the first or second microarray, wherein each known antibody or lectin is affixed at least one discrete locus and wherein the contacting is performed under conditions which would permit an agent, if present in the sample, to specifically bind to its corresponding antibody or lectin in the microarray; and (b) determining whether any known antibody or lectin in the microarray has an agent specifically bound thereto, thereby detecting the presence of the one or more agents in the sample.

In one embodiment of the above methods, the agent is an antibody which correlates with a disease. In a further embodiment of the first method, the agent is an antibody which correlates with an inflammatory disease. In additional embodiments of the above methods, the agent is an antibody which correlates with an infection or the presence of a tumor.

In one embodiment of the instant methods, the method comprises detecting the presence of a plurality of agents in the sample, each of which binds to either a plurality of glycomers, a plurality of insoluble proteins, or a plurality of lectins or antibodies, as applicable. In another embodiment of the instant methods, the method comprises determining the amount of a plurality of agents in the sample, each of which binds to either one glycomer, one insoluble protein or one lectin or antibody, as applicable.

"Determining" whether an agent is bound to a compound in a microarray can be performed according to methods well known in the art. Such methods include, but are not limited to, fluorescence, radioimmunoassay, and immunolabeling detection.

In the instant methods of detection, several embodiments are provided which include, without limitation, the following: (a) one agent in a sample binds to one compound on the instant microarray; (b) one agent in a sample is detected that binds to more than one compound on the microarray; (c) the collective presence of a plurality of agents in a sample is detected, wherein each such agent binds to one or more compounds on the microarray; and (d) each of a plurality of agents in a sample is individually detected, wherein each such agent binds to one or more compounds on the microarray.

This invention further provides three quantitative methods. The first method is a method of determining the amount of one or more agents in a sample, each of which specifically binds to one or more known glycomers, which method comprises: (a) contacting the sample with the first or second microarray, wherein each known glycomer is affixed at least one discrete locus, and wherein the contacting is performed under conditions which would permit an agent, if present in the sample, to specifically bind to its corresponding glycomer in the microarray; (b) for each known glycomer in the microarray, determining the amount of agent specifically bound thereto; and (c) comparing the amounts so determined to a known standard, thereby determining the amount of the one or more agents in the sample.

The second method is a method of determining the amount of one or more agents in a sample, each of which specifically binds to one or more known insoluble proteins, which method comprises: (a) contacting the sample with the first or second microarray, wherein each known insoluble protein is affixed at least one discrete locus, and wherein the contacting is performed under conditions which would permit an agent, if present in the sample, to specifically bind to its corresponding insoluble protein in the microarray; (b) for each known insoluble protein in the microarray, determining the amount of agent specifically bound thereto; and (c) comparing the amounts so determined to a known standard, thereby determining the amount of the one or more agents in the sample.

The third method is a method of determining the amount of one or more agents in a sample, each of which specifically binds to one or more known antibodies or lectins, which method comprises: (a) contacting the sample with the first or second microarray, wherein each known antibody or lectin is affixed at least one discrete locus, and wherein the contacting is performed under conditions which would permit an agent, if present in the sample, to specifically bind to its corresponding antibody or lectin in the microarray; (b) for each known antibody or lectin in the microarray, determining the amount of agent specifically bound thereto; and (c) comparing the amounts so determined to a known standard, thereby determining the amount of the one or more agents in the sample.

In one embodiment of the instant quantitative methods, the agent is an antibody which correlates with a disease.

In a further embodiment of the first method, the agent is an antibody which correlates with an inflammatory disease. In additional embodiments of the above methods, the agent is an antibody which correlates with an infection or the presence of a tumor.

In one embodiment of the instant quantitative methods, the method comprises determining the amount of a plurality of agents in the sample, each of which binds to either a plurality of glycomers, a plurality of insoluble proteins, or a plurality of lectins or antibodies, as applicable. In another embodiment of the instant quantitative methods, the method comprises determining the amount of a plurality of agents in the sample, each of which binds to either one glycomer, one insoluble protein or one lectin or antibody, as applicable.

"Determining" the amount of an agent which is bound to a compound in a microarray can be performed according to well known methods in the art. The "known standards" useful for the instant quantitative methods include, for example, correlations between known concentrations of agents in a control sample and their corresponding values as determined using the instant microarray.

In the instant quantitative methods, several embodiments are provided which include, without limitation, the following: (a) one agent in a sample binds to one compound on the instant microarray; (b) one agent in a sample is quantitated that binds to more than one compound on the microarray; (c) the collective amount of a plurality of agents in a sample are quantitated, wherein each such agent binds to one or more compounds on the microarray; and (d) each of a plurality of agents in a sample is individually quantitated, wherein such agent binds to one or more compounds on the microarray.

This invention further provides three diagnostic methods. The first method is a method of determining whether a subject is afflicted with a disorder characterized by the presence or absence in an afflicted subject of an agent which specifically binds to a known glycomer, which method comprises: (a) contacting a suitable sample from the subject with the first or second microarray, wherein the known glycomer is affixed at least one discrete locus and wherein the contacting is performed under conditions which would permit the agent, if present in the sample, to specifically bind to the known glycomer in the microarray; and (b) determining whether the known glycomer in the microarray has the agent specifically bound thereto, thereby determining whether the subject is afflicted with the disorder.

The second method is a method of determining whether a subject is afflicted with a disorder characterized by the presence or absence in an afflicted subject of an agent which specifically binds to a known insoluble protein, which method comprises: (a) contacting a suitable sample from the subject with the first or second microarray, wherein the known insoluble protein is affixed at least one discrete locus and wherein the contacting is performed under conditions which would permit the agent, if present in the sample, to specifically bind to the known insoluble protein in the microarray; and (b) determining whether the known insoluble protein in the microarray has the agent specifically bound thereto, thereby determining whether the subject is afflicted with the disorder.

The third method is a method of determining whether a subject is afflicted with a disorder characterized by the presence or absence in an afflicted subject of an agent which specifically binds to a known antibody or lectin, which method comprises: (a) contacting a suitable sample from the subject with the first or second microarray, wherein the known antibody or lectin is affixed at least one discrete locus and wherein the contacting is performed under conditions which would permit the agent, if present in the sample, to specifically bind to the known antibody or lectin in the microarray; and (b) determining whether the known antibody or lectin in the microarray has the agent specifically bound thereto, thereby determining whether the subject is afflicted with the disorder.

In one embodiment of the instant diagnostic methods, the subject is human. In one embodiment of the first method, the disorder is an inflammatory disorder. In another embodiment of the first method, the inflammatory disorder is celiac disease. In one embodiment of the third method, the disorder is HIV-1 infection.

The following are specific examples of the instant diagnostic methods. In the first example, a subject's serum is analyzed for the presence of HIV-1 gp120 and IgG-anti-HIV-1 gp120, the presence of both indicating active HIV-1 infection. In the second example, a subject's serum is analyzed for the presence of either HIV-1 gp120 and IgG-anti-HIV-1 gp120, the absence of the HIV-1 gp120 and the presence of IgG-anti-HIV-1 gp120 antibody indicating HIV-1 infection or immunization. In the third example, a subject's serum is analyzed for the presence of HIV-1 gp120 and IgG-anti-HIV-1 gp120, the absence of both indicating that the subject is neither HIV-1 infected nor immunized. In the fourth example, a subject's serum is analyzed for the presence of IgA-anti-gliadin and IgA-anti-TGt, the presence of both indicating that the subject is afflicted with celiac disease. Finally, in the fifth example, a subject's serum is analyzed for the presence of IgA-anti-gliadin, the presence of this antibody indicating the possibility that the subject is afflicted with celiac disease.

This invention further provides a method of determining whether an antibody known to specifically bind to a first glycomer also specifically binds to a second glycomer, which method comprises: (a) contacting the antibody with the first or second microarray, wherein a plurality of glycomers, other than the first glycomer, are affixed at discrete loci in the microarray, and wherein the contacting is performed under conditions which would permit the antibody to specifically bind to the first glycomer if it were present in the microarray; and (b) determining whether any of the glycomers in the microarray, other than the first glycomer, has the antibody specifically bound thereto, thereby determining whether the antibody also specifically binds to a second glycomer.

This invention further provides a method of determining whether an antibody known to specifically bind to a first insoluble protein also specifically binds to a second insoluble protein, which method comprises: (a) contacting the antibody with the first or second microarray, wherein a plurality of insoluble proteins, other than the first insoluble protein, are affixed at discrete loci in the microarray, and wherein the contacting is performed under conditions which would permit the antibody to specifically bind to the first insoluble protein if it were present in the microarray; and (b) determining whether any of the insoluble proteins in the microarray, other than the first insoluble protein, has the antibody specifically bound thereto, thereby determining whether the antibody also specifically binds to a second insoluble protein.

This invention further provides a method of making a microarray comprising a nitrocellulose or Hydrogel support having affixed to its surface at discrete loci a plurality of compounds, which method comprises contacting the nitrocellulose or Hydrogel support with the compounds under suitable conditions, whereby (a) at least one discrete locus is affixed a compound selected from the group consisting of a glycomer, an insoluble protein, a lectin and an antibody, and (b) the composition of compounds at each discrete locus differs from the composition of compounds at least one other discrete locus.

This invention further provides a method of making a microarray comprising a plurality of nitrocellulose or Hydrogel supports, each support having one or a plurality of compounds affixed to its surface at a single discrete locus or a plurality of compounds affixed to its surface at discrete loci, which method comprises contacting the nitrocellulose or Hydrogel supports with the compounds under suitable conditions, whereby (a) at least one discrete locus is affixed a compound selected from the group consisting of a glycomer, an insoluble protein, a lectin and an antibody, and (b) the composition of compounds at each discrete locus differs from the composition of compounds at least one other discrete locus.

This invention further provides a method of making the first article comprising contacting a nitrocellulose or Hydrogel support with dextran at discrete loci under suitable conditions.

In one embodiment of this method, the method further comprises the step Of affixing at least one compound to the dextran at each discrete locus, whereby the composition of compounds at each discrete locus differs from the composition of compounds at least one other discrete locus.

This invention further provides a method of making the second article comprising contacting a plurality of nitrocellulose or Hydrogel supports with dextran, whereby each support has dextran affixed to its surface at one or more discrete loci.

In one embodiment of this method, the method further comprises the step of affixing at least one compound to the dextran at each discrete locus, whereby the composition of compounds at each discrete locus differs from the composition of compounds at least one other discrete locus.

This invention further provides six kits. The first kit comprises one of the instant microarrays and instructions for use. The second kit comprises one of the instant microarrays and a desiccant. The third kit comprises one of the instant microarrays immersed in an aqueous solution.

The fourth kit is a kit for practicing the first diagnostic method, which comprises: (a) a microarray comprising a nitrocellulose or Hydrogel support having affixed to its surface at discrete loci a plurality of compounds, wherein (i) at least one discrete locus is affixed the glycomer to which the agent present or absent in an afflicted subject specifically binds, and (ii) the composition of compounds at each discrete locus differs from the composition of compounds at least one other discrete locus; and (b) instructions for use.

The fifth kit is a kit for practicing the second diagnostic method, which comprises: (a) a microarray comprising a nitrocellulose or Hydrogel support having affixed to its surface at discrete loci a plurality of compounds, wherein (i) at least one discrete locus is affixed the insoluble protein to which the agent present or absent in an afflicted subject specifically binds, and (ii) the composition of compounds at each discrete locus differs from the composition of compounds at least one other discrete locus; and (b) instructions for use.

The sixth kit is a kit for practicing the third diagnostic method, which comprises: (a) a microarray comprising a nitrocellulose or Hydrogel support having affixed to its surface at discrete loci a plurality of compounds, wherein (i) at least one discrete locus is affixed the antibody or lectin to which the agent present or absent in an afflicted subject specifically binds, and (ii) the composition of compounds at each discrete locus differs from the composition of compounds at least one other discrete locus; and (b) instructions for use.

This invention further provides a first antibody capable of specifically binding to a glycomer present on the surface of a mammalian macrophage, which glycomer, or structural mimic thereof, is also endogenous to, and present on the surface of, a bacterial cell. In one embodiment, the antibody is a groove-type antibody. In another embodiment, the antibody is designated 4.3.F1 (ATCC Accession No. PTA-3259). In a further embodiment, the antibody is designated 45.21.1 (ATCC Accession No. PTA-3260).

This invention further provides a second antibody capable of specifically binding to a glycomer present on the surface of a mammalian intestinal epithelial cell, which glycomer, or structural mimic thereof, is also endogenous to, and present on the surface of, a bacterial cell. In one embodiment, the antibody is a cavity-type antibody. In another embodiment, the antibody is designated 16.4.12E (ATCC Accession No. PTA-3261).

This invention further provides a method of determining whether a subject is afflicted with a disorder characterized by the presence of a glycomer on the surface of macrophages in an afflicted subject, which glycomer, or structural mimic thereof, is also endogenous to, and present on the surface of, a bacterial cell, comprising: (a) contacting a sample of the subject's macrophages with the first antibody; and (b) determining whether the antibody specifically binds to the macrophages in the sample, such binding indicating that the subject is afflicted with the disorder. In one embodiment the subject is human. In another embodiment, the disorder is an immune disorder or an inflammatory disorder.

This invention provides a method of determining whether a subject is afflicted with a disorder characterized by the presence of a glycomer on the surface of intestinal epithelial cells in an afflicted subject, which glycomer, or structural mimic thereof, is also endogenous to, and present on the surface of, a bacterial cell, comprising: (a) contacting a sample of the subject's intestinal epithelial cells with the second antibody; and (b) determining whether the antibody specifically binds to the intestinal epithelial cells in the sample, such binding indicating that the subject is afflicted with the disorder. In one embodiment the subject is human. In another embodiment, the disorder is an immune disorder or an inflammatory disorder. In a further embodiment, the disorder is celiac disease.

In one embodiment of each facet of this invention (i.e., each of the instant compositions of matter and methods), the glycomer, insoluble protein, lectin or antibody of the instant microarray is conjugated with a green fluorescent protein (GFP), and this conjugate is affixed to a nitrocellulose or Hydrogel support either via the GFP moiety or not. "Conjugation" as used herein includes, without limitation, conjugation by covalent or noncovalent means. In a further embodiment, conjugation of a second protein with GFP is accomplished via formation of a fusion protein with the second protein. As used herein, "a fusion protein" includes, for example, a protein encoded by a gene that comprises a GFP-encoding region and a non-GFP-encoding region. As used herein, GFP includes, without limitation, whole GFP as well as fluorescent fragments thereof. In a further embodiment of each facet of this invention, GFP alone (i.e., unconjugated form), is bound to the instant microarray.

The fifth microarray comprises a nitrocellulose or Hydrogel support having affixed to its surface at discrete loci a plurality of compounds, wherein (a) at least one discrete locus is affixed a compound associated with *Bacillus anthracis* and selected from the group consisting of a glycomer and a protein, and (b) the composition of compounds at each discrete locus differs from the composition of compounds at least one other discrete locus.

The sixth microarray comprises a plurality of nitrocellulose or Hydrogel or Hydrogel supports, each support having one or a plurality of compounds affixed to its surface at a single discrete locus or a plurality of compounds affixed to its surface at discrete loci, wherein (a) at least one discrete locus is affixed a compound associated with *Bacillus anthracis* and selected from the group consisting of a glycomer and a protein, and (b) the composition of compounds at each discrete locus differs from the composition of compounds at least one other discrete locus.

The fourth method of detection is a method of detecting in a sample the presence of one or more agents associated with *Bacillus anthracis* which specifically bind to one or more glycomers, which method comprises: (a) contacting the sample with the fifth or sixth microarray, wherein each glycomer is affixed at least one discrete locus and wherein the contacting is performed under conditions which would permit an agent, if present in the sample, to specifically bind to its corresponding glycomer in the microarray; and (b) determining whether any glycomer in the microarray has an agent specifically bound thereto, thereby detecting the presence of the one or more agents in the sample.

The fifth method of detection is a method of detecting in a sample the presence of one or more agents associated with *Bacillus anthracis* which specifically bind to one or more proteins, which method comprises: (a) contacting the sample with the fifth or sixth microarray, wherein each protein is affixed at least one discrete locus and wherein the contacting is performed under conditions which would permit an agent, if present in the sample, to specifically bind to its corresponding protein in the microarray; and (b) determining whether any known protein in the microarray has an agent specifically bound thereto, thereby detecting the presence of the one or more agents in the sample.

The sixth method of detection is a method of detecting in a sample the presence of one or more glycomers or proteins which specifically bind to one or more antibodies or lectins associated with *Bacillus anthracis*, which method comprises: (a) contacting the sample with the fifth or sixth microarray, wherein each antibody or lectin is affixed at least one discrete locus and wherein the contacting is performed under conditions which would permit an agent, if present in the sample, to specifically bind to its corresponding antibody or lectin in the microarray; and (b) determining whether any antibody or lectin in the microarray has an agent specifically bound thereto, thereby detecting the presence of the one or more agents in the sample.

Also envisioned in this invention are all embodiments of the microarray technology described herein as applied to agents associated with *Bacillus anthracis*. Specifically, this invention provides, for example, all such embodiments relating to methods of quantitative detection, diagnosis, binding detection, making microarrays, kits, and antibodies and glycomers identified using the instant methods, as applicable.

This invention will be better understood from the Experimental Details that follow. However, one skilled in the art will readily appreciate that the specific methods and results discussed are merely illustrative of the invention as described more fully in the claims which follow thereafter.

Experimental Details

First Series of Experiments

This invention provides novel antigen- and antibody-based microarrays for monitoring and quantifying a broad spectrum of biological molecules and their molecular interactions. A microarray technique is used to spot thousands of antigens and/or antibodies on a solid surface. This strategy can be applied to any molecular target, including naturally occurring proteins, carbohydrates, lipids and nucleic acids, as well as synthetic compounds. The instant microarray is useful for monitoring the expression of specific antibodies and other cellular factors in body fluids, and is therefore useful for disease diagnosis and basic immunological investigation. When a large repertoire of distinct monoclonal antibodies are arrayed, an antibody library microarray is produced. Application of these microarrays for global analysis of gene expression at the translational and post-translational levels is envisioned. The Elvin A. Kabat Collection of antigens and antibodies at Columbia University is useful in practicing this technology.

Figure 2:
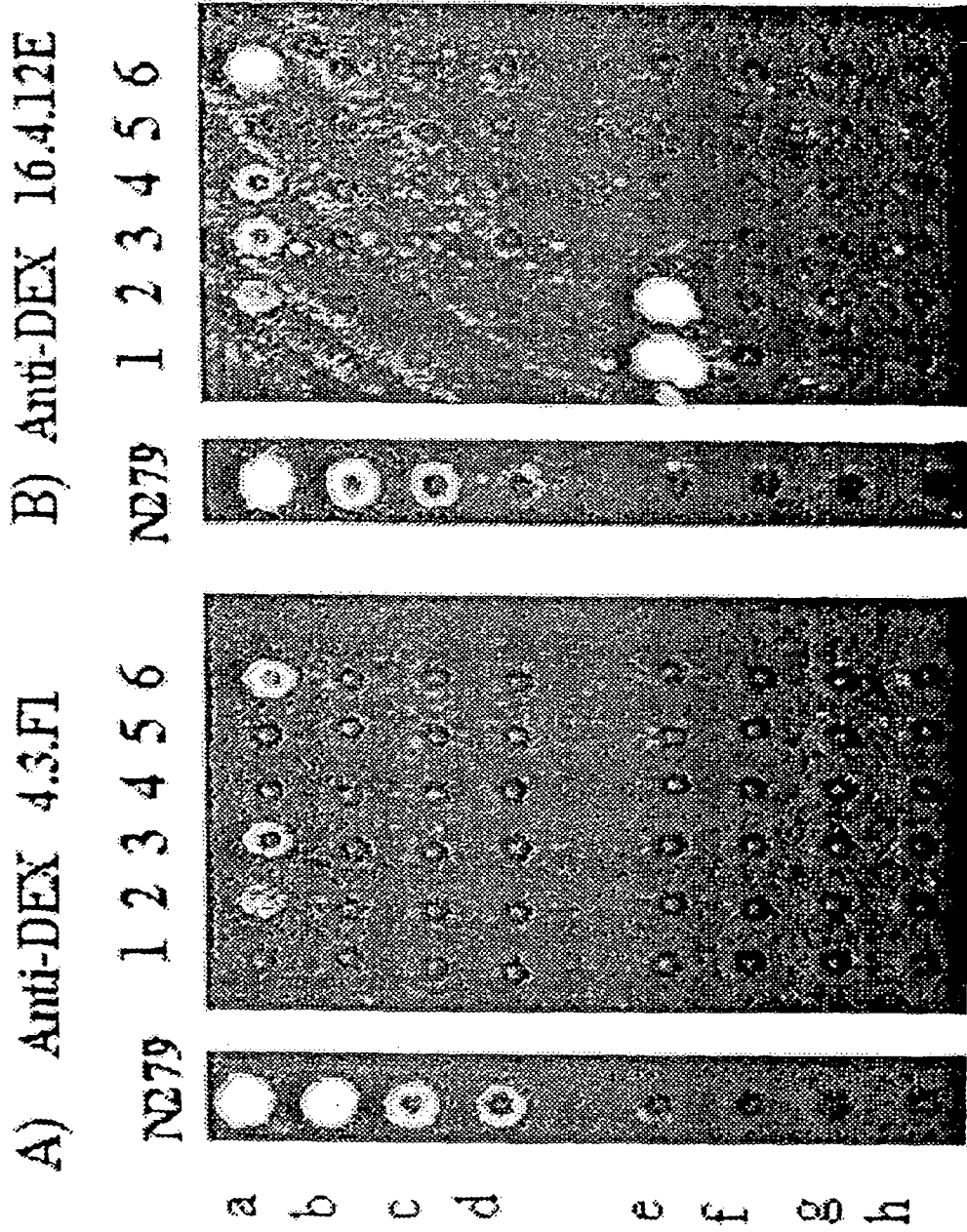

I. Materials, Methods and Results (A) Method for Antigen/Antibody Immobilization It is experimentally demonstrated here that nitrocellulose-coating can serve as a suitable matrix for immobilizing polysaccharides, glycoprotein, glycolipid, protein and antibodies on a glass surface without chemical conjugation. A set of commercially available glass slides, including those coated with nitrocellulose (ONCYTE Film-Slides, Grace Bio-Labs, Inc., Bend, Oreg.), poly-L-lysine. (POLY-PREP™, Sigma), aminoalkylsilane (SILANE-PREP™, Sigma) and regular micro-glass slides, were compared for their capacity to immobilize macromolecules of distinct structural properties. In the initial experiments, fluorescence-conjugated dextran molecules were applied. An extended panel of antigen preparations, including polysaccharide, glycoprotein, glycolipid, protein and antibody, were then investigated. Examples of these investigations are shown in FIGS. 1 and 2.

(B) Printing and Long-Term Storage of Antigen/Antibody Microarrays

A high-precision robot designed to produce cDNA microarrays (GMS 417 Arrayer, Genetic Microsystems, Inc., Woburn Mass.) was used to spot carbohydrate antigens onto a glass slide pre-coated with nitrocellulose polymer (ON-CYTE Film-Slides, Grace Bio-Labs, Inc., Bend, Oreg.). Spots of antigens were printed with spot sizes at approximately 200 micron and 400 micron intervals, center-to-center. They were air dried and stored at room temperature before use. Conditions for long-term storage of the printed antigen/antibody microarrays were compared. The results show that (1) the air-dried carbohydrate microarrays can be stored at room temperature for at least one year without significant inactivation of their immunological activities; and (2) the antibody microarrays can be stored in an aqueous solution at 4° C. for at least one year without significant decrease in their antigen-binding activity, as illustrated using antibodies with anti-carbohydrate specificity.

(C) Proper Macromolecules for Coupling Smaller Bioreactive Molecules and Displaying them on a Solvent-Accessible Surface Dextran preparations, especially α(1,6)dextrans, can serve as carrier molecules to conjugate other biologically active molecules. Such dextran-containing conjugates can be immobilized on a nitrocellulose-surface without further chemical conjugation. This method was demonstrated by immobilizing the fluorescence-α(1,6)dextran conjugates of different molecular weights, ranging from 35 kD to 2000 kD, on a nitrocellulose-coated glass slide. The fluorescence group is accessible to the anti-fluorescence antibodies in solution, thereby demonstrating specific binding. Methods for producing dextran-conjugates for surface immobilization follow.

(1) Mild Sodium Periodate Oxidization of Dextran to Create Highly Reactive Aldehyde Functional Groups (CHO)

α(1,6)dextran, preparation N279 (B512), was dissolved in 0.01M NaAcetate buffer, pH 5.5, at 10 mg/ml and warmed in a 37° C. water bath for 30 minutes. $NaIO_4$ was then added to the final concentration of $1 \times 10^{-2}$ M. The solution was mixed well and left to stand at room temperature for one hour in the dark. The preparation was dialyzed against 0.02M BBS (Borate buffered saline) pH 8.0, 4° C., overnight.

(2) Mild Oxidization of Carbohydrate Structure of IgG to Create CHO Group for Surface Immobilization The above protocol was also applied to produce active CHO groups in carbohydrate molecules that exist naturally in the C region of IgG molecules. Such CHO-activated IgG is then covalently linked to the amino group of an amino-dextran molecule that was immobilized on a nitrocellulose-coated glass slide. Preparations of amino-dextrans are commercially available (Molecular Probes, Eugene). This method of IgG immobilization uses a carbohydrate structure attached in the Fc region of IgG, which is away from the antibody combining sites of antibody molecule, and thus preserves the antibodies' binding activity.

(3) Coupling of Biotin-LC-Hydrazide to the Oxidized Dextran

The above oxidized dextran was diluted 10-fold in 0.1M NaAcetate, pH 5.5. A 1/3 volume of 5 mM Biotin-LC-Hydrazide was added dropwise. The mixture was shaken at room temperature for one hour. The reaction was terminated by addition of 0.5 ml of 1M Tris HCl, pH 7.5, and the mixture was then dialyzed against Tris buffer (0.1M Tris pH 7.5, 0.1 M NaCl, 2.0 mM MgCl2). The biotinylated dextrans are then ready to be immobilized on nitrocellulose-coated glass slides so that their biotin-groups are accessible to other molecules in solution.

(4) Surface, Immobilization of Biotinylated Molecules

Standard methods were applied to couple NHS-Biotin (BRL #5533LA) to target molecules, i.e., either protein or polysaccharide. The biotinylated molecule was incubated with avidin at a proper molar ratio depending on the molecular weight of the target and its molar ratio with biotin. The molecules were then spotted on a surface that was precoated with biotin-dextran and blocked with BSA or gelatin. This strategy allows a flexible arrangement of antigen or antibody microarrays for a desired purpose, and avoids non-specific binding of target molecules on a surface.

(5) Glutaraldehyde-Conjugation to Generate Dextran-Small Molecule Conjugates

Small bioactive molecules containing amine group(s) can be coupled to amino-dextrans (Molecular Probes) by glutaraldehyde. Glutaraldehyde was added to the mixtures of the target molecule and amino-dextran (at proper molar ratios) to a final concentration of 0.2%. They were at room temperature for two hours. The reaction was stopped by addition of 1M ethanolamine at 6.1 μl/ml. The mixture was at room temperature for an additional two hours and then dialyzed against 1×PBS or other proper solution, overnight. The dextran-small molecule conjugates were then spotted on nitrocellulose-coated slides. This method is suitable for generating microarrays having a large repertoire of small molecules and useful for high throughput drug screening or other biomedical investigations.

(D) Solutions for Preparing Macromolecules of Distinct Physicochemical Properties (1) Solution Storage Microbial polysaccharides, blood group substances and glycolipids were solubilized and stored in saline at a concentration of about 1 mg/ml at 4° C. A small droplet of chloroform was added to prevent microbes. In this simple way, most solutions, can be stored for years. The agents were diluted in saline at required concentrations immediately before spotting.

(2) Protein Antigens

Soluble protein preparations were prepared at relatively high concentrations in 1×PBS (mg/ml) with addition of 20% glycerol and frozen at −80° C. They were diluted in 1×PBS before use and stored at 4° C. for a short period of time (a few days). Antibody preparations were generally stored at 4° C. in 1×PBS except in special cases. Some E. Coli-expressed protein antigens are water-insoluble. The preparations were purified in a denatured condition and stored them in the same solution at 4° C. The freezing process is avoided for these proteins. In most cases these preparations can be immobilized on a nitrocellulose matrix without special treatment. This method has been applied successfully in applicant's laboratory for hybridoma screening.

(E) Staining and Scanning of Antigen/Antibody Microarrays (1) General Application Protocol Immediately before use, the printed antigen/antibody microarrays were rinsed with 1×PBS with 0.05% TWEEN® 20 and then blocked by incubating the slides in 1% BSA in PBS containing 0.05% $NaN_3$ at 37° C. for 30 minutes. The microarrays were then incubated at room temperature with fluorescent-antibody conjugate at proper titration in 1% BSA PBS containing 0.05% $NaN_3$ and 0.05% TWEEN® 20 (polysorbate 20). Slides were rinsed with 1×PBS with 0.05% TWEEN® 20 (polysorbate 20) five times, air-dried at room temperature and then scanned for fluorescent signals. A ScanArray 5000 Standard Biochip Scanning System (GSI Lumonics, Inc. and Packard BioChip Technologies, Inc.) which is equipped with multiple lasers, emission filters, ScanArray Acquisition Software and QuantArray Microarray Analysis Software, was used to scan the stained antigen microarray, quantify spot-associated fluorescent-signals and analyze data.

(2) Special Application Protocols (a) Method for Improving Signal Detection

A technical problem that has limited the application of the nitrocellulose-coated glass slide is its association with "white color" and non-specific fluorescent signals upon scanning. This problem is solved using the method that follows. (a) After staining a microarray glass slide, allow it to air-dry for a few minutes (at this stage, the nitrocellulose-coated region is white in color). (b) Soak the slide in 100% ethanol for 1-2 minutes until the white color of the nitrocellulose-coated region disappears and the entire slide becomes transparent. (c) Quickly spin the slide to remove extra ethanol. (d) Scan the slide when it is completely transparent. After storage for a few days or longer, depending on the humidity level in the air, the slide may turn back to the white color. One may repeat the above process to make the slide transparent again if necessary.

(b) Staining Antigen/Antibody Microarrays Using Non-Fluorescent Dyes

The antigen/antibody microarray can be stained with antibodies, antigens or other reactors that are conjugated with non-fluorescent dyes. The commonly used alkaline phosphatase (AP) and peroxidase are useful alternatives. One may practice this method as follows. (a) Stain an antigen microarray with a human serum sample at the proper dilution as described above. (b) After washing, stain the slide with an AP-conjugated anti-human IgG antibody at the proper dilution. (c) Wash the slide and develop the color by adding AP substrate BCIP alone or BCIP plus NBT. (d) Stop the reaction by adding a Tris-EDTA solution (20 mM Tris, pH 7.5, 5 mM EDTA). (e) Rinse the slide with distilled water and then scan it with a non-fluorescent slide scanner, or observe the color reaction under a regular microscope.

(F) Sensitivity of Antigen Microarrays

Sensitivity is one of the critical parameters that determine the diagnostic value of antigen microarrays. In, preliminary experiments (FIG. 1), dextran preparations were arrayed on nitrocellulose-coated glass slides in concentrations ranging from 100 µg/ml to 3.3 ng/ml. They were stained with fluorescence-labeled anti-dextran mAbs, either 4.3.F1 or 16.4.12E, at a concentration of 1 µg/ml. In both cases, the captured fluorescent signals (intensities) detected were positively correlated to the antigen concentrations. For example, 4.3.F1 was only detectable when the concentrations of N279, LD7 and B1299S are higher than 0.4, 20 or 100 µg/ml, respectively (spots of antigens with concentrations lower than 0.4 µg/ml were not shown in FIG. 1). Signal saturation was not observed even at the highest concentration of 100 µg/ml, showing the technical potential for improving the sensitivity of antigen microarrays.

(G) Epitope-Specific Antigen Microarray

Glycoconjugate technology was used to produce an "epitope-specific antigen microarray". A naturally occurring antigen may be composed of multiple antigenic determinants. Frequently, one or a few of them serve as predominant antigenic determinants for host recognition. Antibodies specific for some carbohydrate epitopes of a microbial polysaccharide can be more protective than those reacting with others. There are also cross-reactive antigenic determinants that may be shared among strains or even species of microorganisms. Such cross-reactivities may cause difficulty in typing corresponding infectious agents. Thus, it is useful to define the fine specificities of antibodies elicited by an infection or by vaccination.

To produce an epitope-specific microarray, preparations of glycoproteins displaying $\alpha(1,6)$-linked glucoses, i.e., isomaltotriose-coupled BSA (IM3-BSA) or its KLH-conjugate (IM3-KLH), were applied in a microarray experiment. These conjugates have the terminal non-reducing end epitope of $\alpha(1,6)$dextran in common but differ in their protein carriers. As expected, mAb 16.4.12E (cavity-type), but not mAb 4.3.F1 (groove-type), bind to the microspots of IM3-protein conjugates (FIGS. 1E and 2E). Thus, glycoproteins can be immobilized on a nitrocellulose-coated glass slide and their antigenic determinants remain accessible to antibodies in solution.

Neoglycolipids, i.e., glycolipid conjugates, were used to produce epitope-specific microarrays, wherein stearylamine-isomaltosyl oligosaccharide conjugates, ST-IM3, ST-IM5 and ST-IM7, were applied (data not shown). Such glycolipid conjugates are homogeneic, since each lipid molecule can only be coupled by a single oligosaccharide. Unlike a glycoprotein conjugate, the sugar chain can be conjugated on to multiple sites of a protein molecule, generating a heterogenic population of antigenic determinants. Both sugar epitope and the amino acid residues adjacent to it may be structurally involved in forming these antigenic determinants.

(H) Antibody Microarrays

Experiments were performed to develop antibody-based microarrays. A panel of anti-dextran mAbs were immobilized at a concentration of 0.5 mg/ml on a set of glass slides. These included (a) a nitrocellulose-coated glass slide (ONCYTE Film-Slides, Grace Bio-Labs, Inc., Bend, Oreg.); (b) a poly-lysine treated slide (POLY-PREP™, Sigma); (c) a silane-treated glass slide (SILANE-PREP™, Sigma); and (d) an un-treated, pre-cleaned glass slide. These slides were then reacted with fluorescence-tagged dextran preparations of distinct structures. Only the nitrocellulose-slides showed spots of specific fluorescent signals. Thus, anti-dextran mAbs arrayed on the nitrocellulose-glass slide retained their antigen binding specificities. As described above, the antibody microarrays can be stored at room temperature in an air-dried condition for a few months and maintain their antibody-binding activity. The antibodies investigated include monoclonal antibodies of different isotypes (IgM, IgG and IgA).

II. Application of Antigen-Antibody Biochip Technology for Basic Research and Clinical Investigation (A) Mapping Antibody Combining Sites by Applying Antigen/Antibody Microarrays A well-established antigen-antibody system, i.e., dextrans and anti-dextran monoclonal antibodies (mAbs) [10,11], was used for these investigations. A panel of purified dextran preparations of different linkage compositions and of different ratios of terminal/internal epitopes [10] were immobilized on nitrocellulose-coated glass slides and then incubated with monoclonal antibodies of defined specificities, either the cavity-type or the groove-type anti-dextrans [12]. The former is specific for the terminal non-reducing end structure of α(1, 6)dextran; the latter recognizes the internal linear chain of the polysaccharide. When a cavity-type mAb, 16.4.12E, was applied on the glass slide, it bound to the immobilized α(1, 6)dextran preparations having branches, but not those with only internal linear chain structures. By contrast, a groove-type mAb, 4.3.F1, bound to the dextran preparations dominated by linear chain structures, but not to the heavily branched α(1,6)dextrans (FIG. 1). Thus, the use of polysaccharides of defined structure in microarrays is an important strategy for studying antibody specificities and for characterizing immune responses to microbial infections.

As described above, methods to produce epitope-specific microarrays were also established, allowing characterization of the fine specificity of antibodies. Considering the presence of both the internal chain epitopes and the terminal non-reducing end epitopes in many polysaccharides, application of both polysaccharide macromolecules and their oligosaccharide conjugates on the instant microarrays will significantly enhance the power of the system, including its sensitivity, specificity and the detecting repertoires of antigenic determinants.

(B) Investigation of the Specificity and Cross-Reactivity of Antibodies/Receptors An advantage of the instant microarray is that it provides a high throughput strategy to characterize the specificity and cross-reactivity of an antibody or a lectin molecule. FIG. 2 shows an example of this approach. A collection of about 50 carbohydrate-containing antigens, including microbial polysaccharides, blood group substances and other glycoconjugates, were arrayed on the nitrocellulose-coated slide. They were then stained with anti-dextran mAbs, 4.3.F1, or 16.4.12E. As shown in FIG. 2, certain cross-reactive signals were detected for a few antigen preparations, being spots 2a, 3a and 6a for mAb 4.3.F1, and 2a, 3a, 4a, 6a, 1e, and 2e for 16.4.12E. Antigens arrayed at these locations are: 2a. *Klebsiella* polysaccharide type 11; 3a. *Klebsiella* type 13; 4a. *Klebsiella* type 21; 6a. Chondroitin sulfate B polysaccharide; 1e. IM3-BSA and 2e. IM3-KLH.

Figure 3:
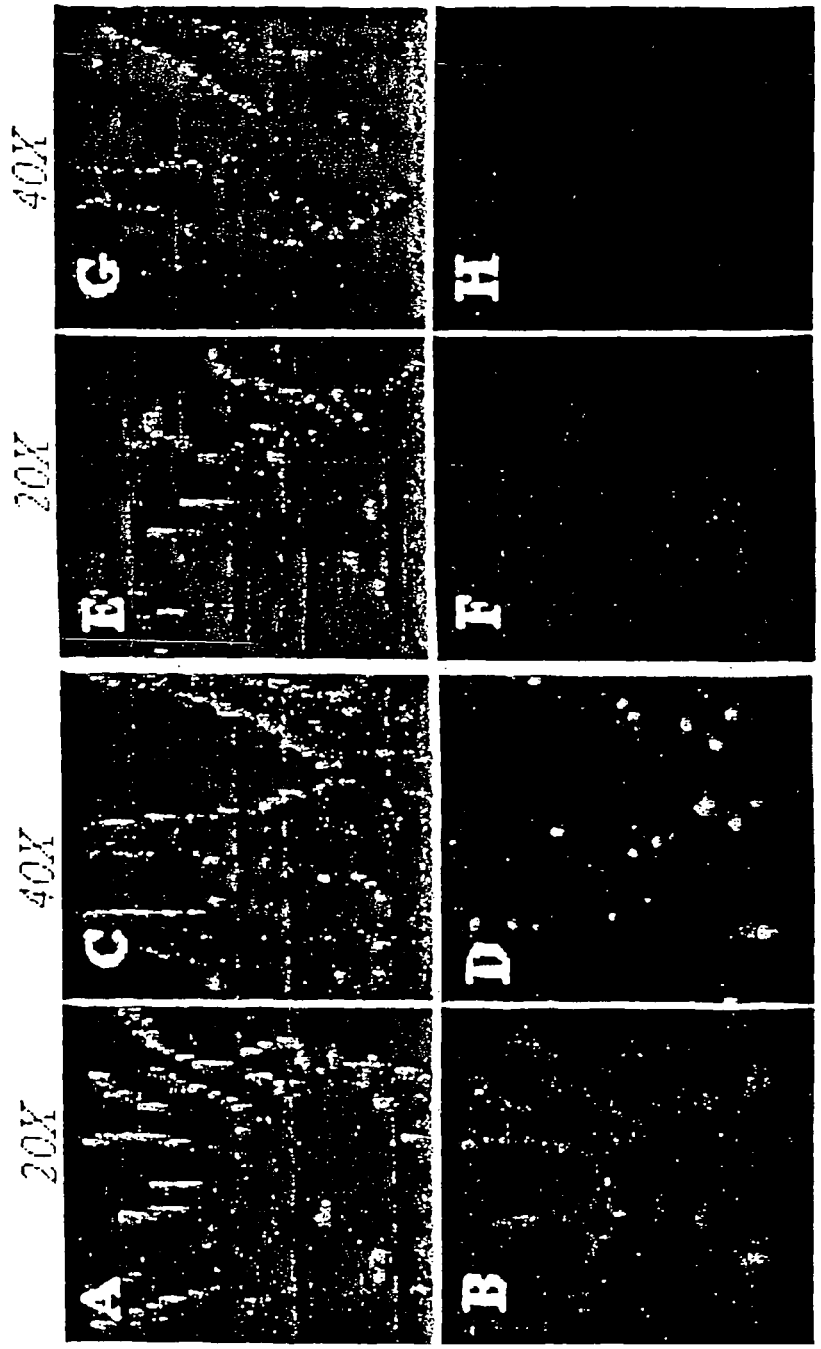
Figure 4:
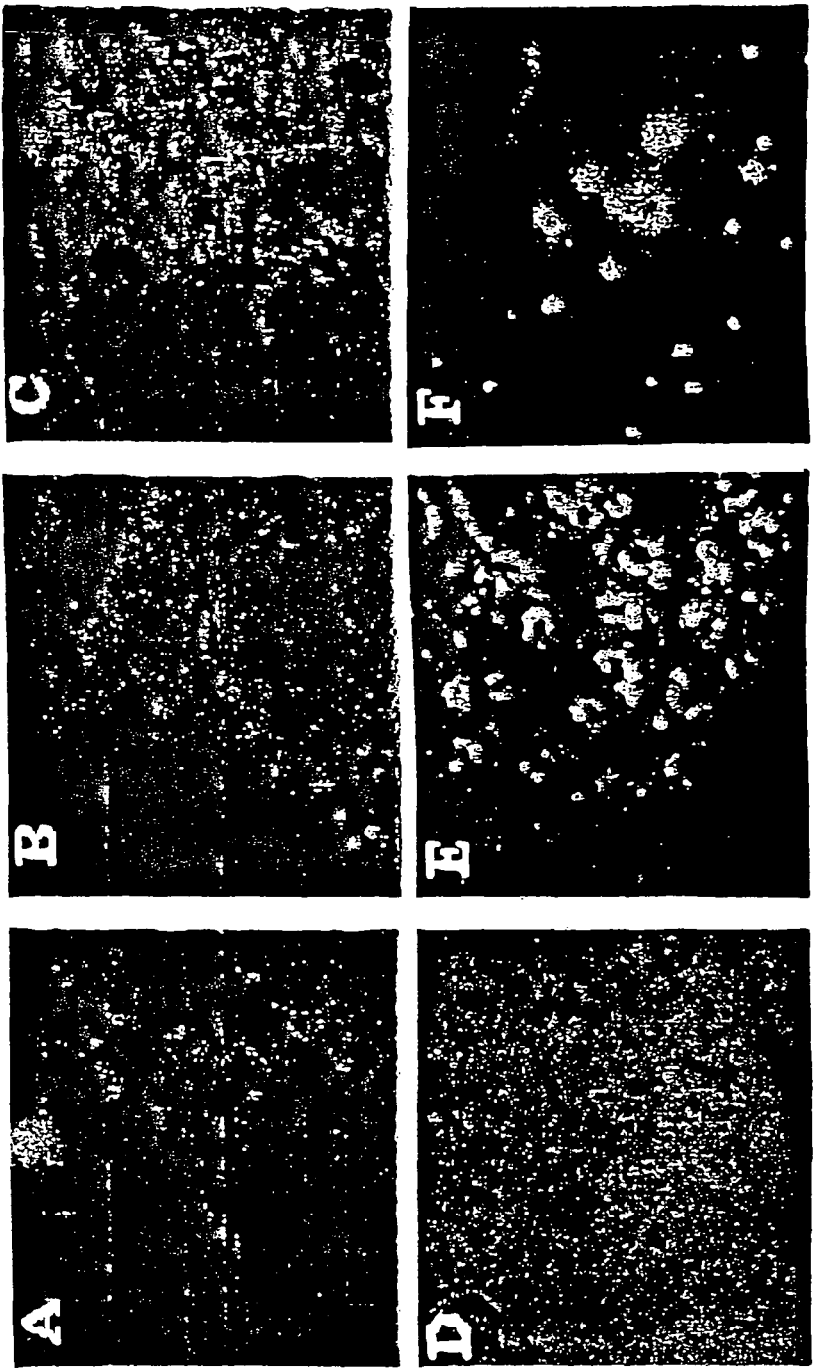
Figure 5:
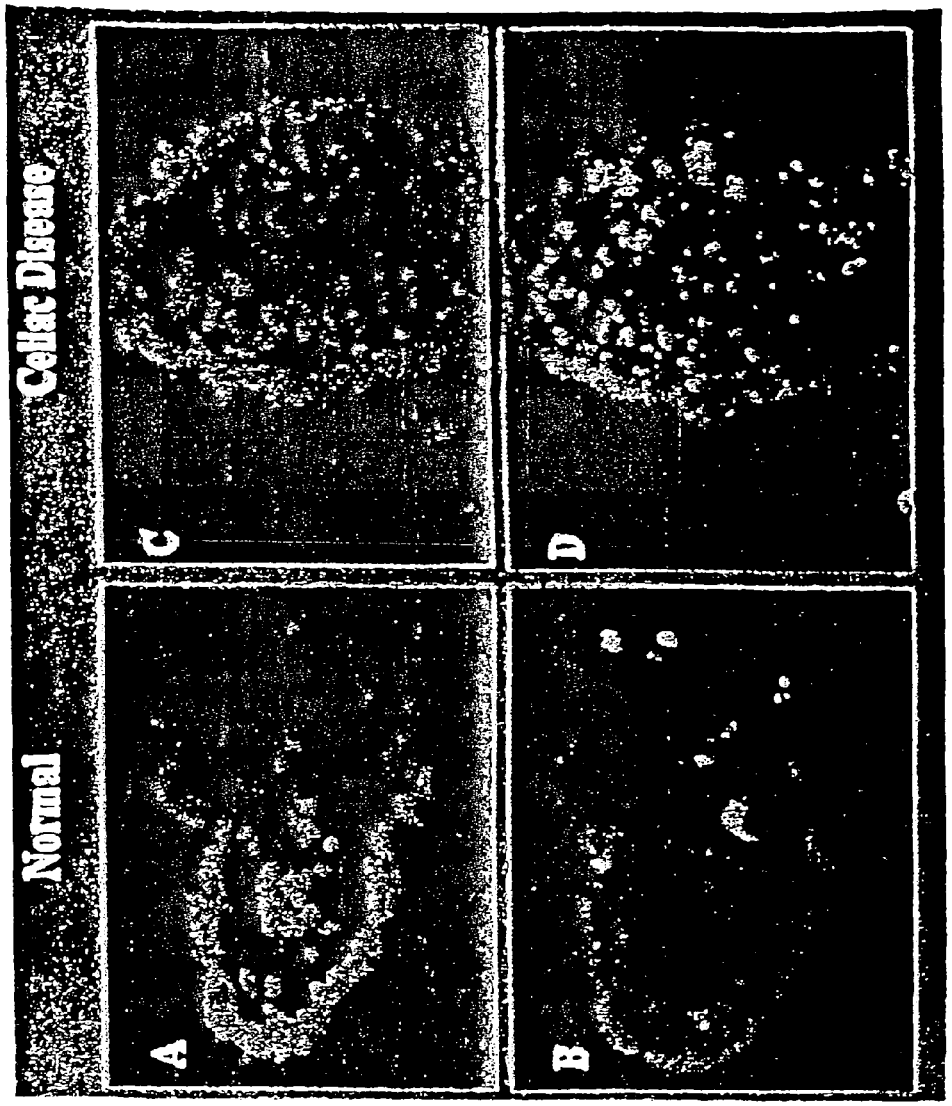

As discussed above, the binding of 16.4.12E (cavity-type), but not 4.3.F1 (groove-type), to IM3-BSA (1e) and IM3-KLH (2e) reflects the epitope-specific binding activities of these two monoclonal antibodies. Their binding to other antigens is, however, unexpected. The fluorescent intensities of cross-reactivities are much weaker than the binding to α(1,6)dextran N279. They were detected at a high antigen concentration (500 µg/ml), corresponding to or lower than the signals of specific bindings at much lower antigen concentrations (0.8 to 4 µg/ml). On an ELISA plate, such weak cross-reactivities are not detectable (data not shown). The cross-reactivities to CS-B polysaccharide (FIG. 2A and FIG. 2B), is interesting since CS-B is not a microbial antigen and was prepared from the intestinal mucosa of porcine. Further investigation of such reactivity led to the discovery of Dex-IdX as a cell type-specific marker in mouse and human (FIGS. 3-5).

(C) Clinical Application of Antigen Microarrays

The antigen-based microarray can be applied for detection and characterization of a wide range of microbial infections. During infection, whether viral, bacterial, fungal or parasitic, the host usually responds with the formation of antibodies which can be detected by a modified version of any of the methods used for antigen detection. The formation of antibodies and their time course depends on the antigenic stimulation provided by the infection. Recognition of these patterns provides evidence of recent or past infection. Microarrays of a large panel of antigens allow detection of many specificities in a single assay and thus allow a rapid diagnosis of infections. The diagnostic power of the instant microarrays will only increase as more microbial antigens and/or their antigenic determinants are characterized and applied.

To demonstrate this principle, a small scale antigen microarray with about 50 antigens was produced (FIG. 2) and tested with human sera from normal individuals and celiac patients. These specimens were diluted at 1:20 in 1% BSA-PBS with 0.025% Tween 20 and applied to the microarray. The bound human antibodies were visualized by application of a second antibody specific for human IgG or IgA that was conjugated with a fluorescent molecule (an anti-human $IgG^{Cy3}$ and an anti-human $IgA^{Cy5}$). The positive staining of the microspots of these arrayed antigens by the serum specimens ranged from 6% (three of fifty spots were detected) to 12% (six of fifty spots were detected). The antigens detected were mainly microbial polysaccharides, including *Klebsiella* polysaccharide type 7, 13, 14, 21 and 33, Dudmans *Rhizobium* Trifelli TA1 and Levan.

The majority of the positive staining was of human IgG antibodies, although IgAs were also detected. This investigation has demonstrated that the instant microarray has the sensitivity to detect specific antibodies in human serum. Given the current capacity of microspotting technology in the art, about twenty thousand antigens can be arrayed on a single glass slide. It is expected, therefore, that this microarray is capable of characterizing a wide range of microbial infections using very limited samples in a single experiment.

III. Discussion

The instant microarrays are significantly different from known cDNA microarray and oligo-chip technologies, which target only nucleic acids. Applicant has employed high throughput microarray technology to develop a novel strategy for detecting, quantifying and characterizing proteins, carbohydrates and other biological molecules, and useful in the new areas of post-genomic research, namely proteomics and glycomics.

Differing from current immunoassays which detect specific molecules one-by-one, this technology is designed to detect and quantify a large repertoire of distinct biological molecules in a single assay. Combining a high throughput microarray technique and a sensitive confocal fluorescent scanning method, this technology is useful for detecting thousands of distinct molecules using a small amount of biological specimen, such as a drop of blood or other bodily fluid. This technology can be extended to the genome-wide scanning of protein expression and post-translational modification.

REFERENCES

1. Ramsay, G., DNA chips: state-of-the art. Nature Biotechnology, 1998. 16(1): p. 40-4.
2. Brown, P. O. and D. Botstein, Exploring the new world of the genome with DNA microarrays. Nature Genetics, 1999. 21(1 Suppl): p. 33-7.
3. DeRisi, J. L., V. R. Iyer, and P. O. Brown, Exploring the metabolic and genetic control of gene expression on a genomic scale. Science, 1997. 278(5338): p. 680-6.
4. Lueking, A., et al., Protein microarrays for gene expression and antibody screening. Analytical Biochemistry, 1999. 270(1): p. 103-11.
5. Ge, H., UPA, a universal protein array system for quantitative detection of protein-protein, protein-DNA, protein-RNA and protein-ligand interactions. Nucleic Acids Research, 2000. 28(2): p. e3.
6. Varki, A., Biological roles of oligosaccharides: all of the theories are correct. Glycobiology, 1993. 3(2): p. 97-130.
7. Feizi, T., Carbohydrate recognition systems in innate immunity. Advances in Experimental Medicine & Biology, 1998. 435: p. 51-4.
8. Feizi, T. and R. W. Loveless, Carbohydrate recognition by *Mycoplasma pneumoniae* and pathologic consequences. American Journal of Respiratory & Critical Care Medicine, 1996. 154(4 Pt 2): p. S133-6.
9. Zareba, T. W., et al., Binding of extracellular matrix proteins by enterococci. Curr Microbiol, 1997. 34(1): p. 6-11.
10. Wang, D. and E. A. Kabat, Carbohydrate Antigens (Polysaccharides), in Structure of Antigens, M. H. V. V. Regenmortal, Editor. 1996, CRC Press: Boca Raton New York London Tokyo. p. 247-276.
11. Wang, D., et al., The repertoire of antibodies to a single antigenic determinant. Molecular Immunology, 1991. 28(12): p. 1387-97.
12. Cisar, J., et al., Binding properties of immunoglobulin combining sites specific for terminal or nonterminal antigenic determinants in dextran. J. Exp. Med., 1975. 142: p. 435-459.
13. Matsuda, T. and E. A. Kabat, Variable region cDNA sequences and antigen binding specificity of mouse monoclonal antibodies to isomaltosyl oligosaccharides coupled to proteins T-dependent analogues of α(1,6)dextran. J. Immunol., 1989. 142: p. 863-870.
14. Chen, H. T., S. D. Makover, and E. A. Kabat, Immunochemical studies on monoclonal antibodies to stearyl-isomaltotetraose from C58/J and a C57BL/10 nude mouse. Mol. Immunol., 1987. 24: p. 333-338.
15. Wang, D., et al., Two families of monoclonal antibodies to α(1,6)dextran, $V_H$19.1.2 and $V_H$9.14.7, show distinct patterns of $J_k$ and $J_H$ minigene usage and amino acid substitutions in CDR3. J. Immunol., 1990. 145: p. 3002-3010.

Second Series of Experiments

I. Materials and Methods

A. Carbohydrate Antigens and Antibodies

Figure 7:
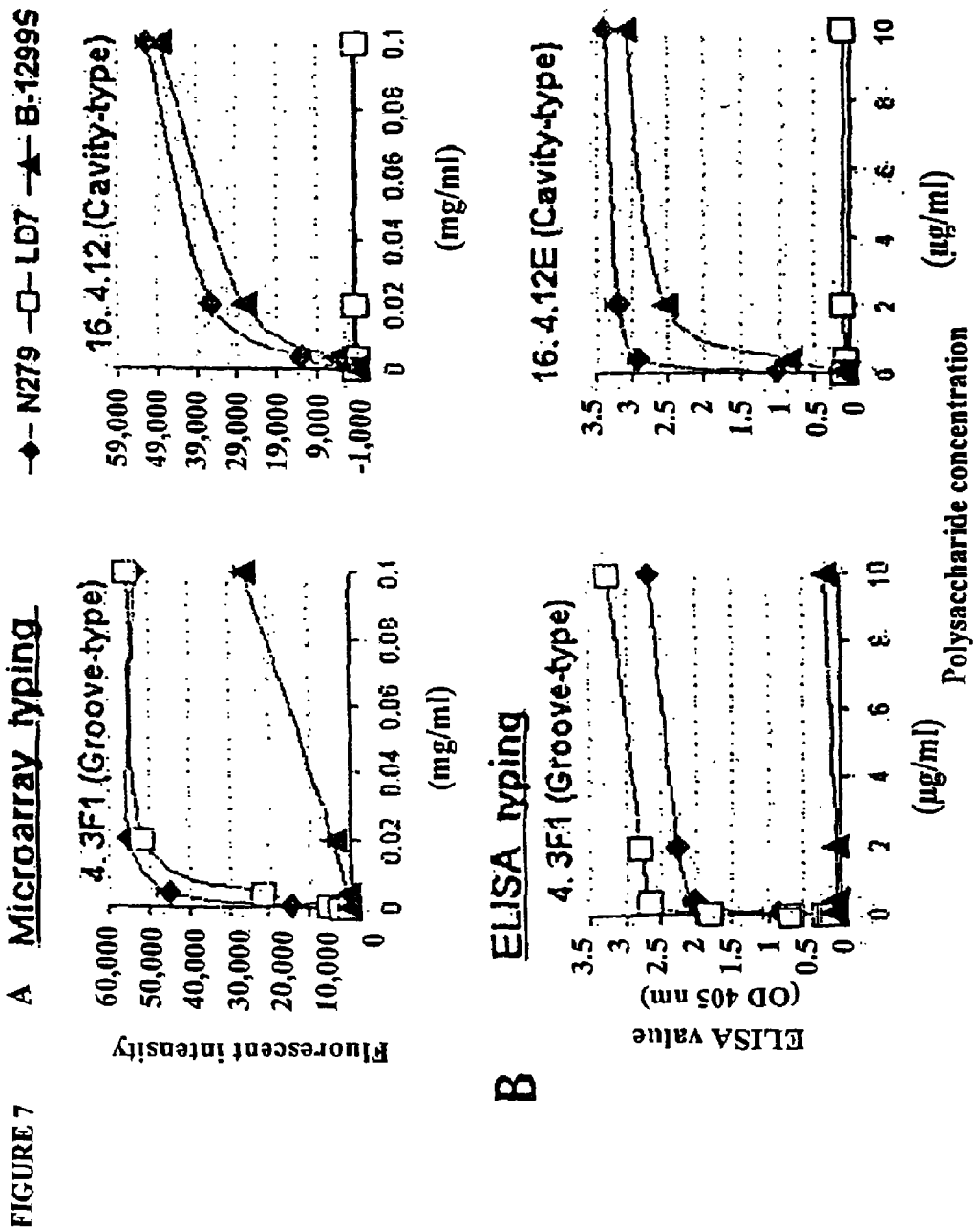
Figure 9:
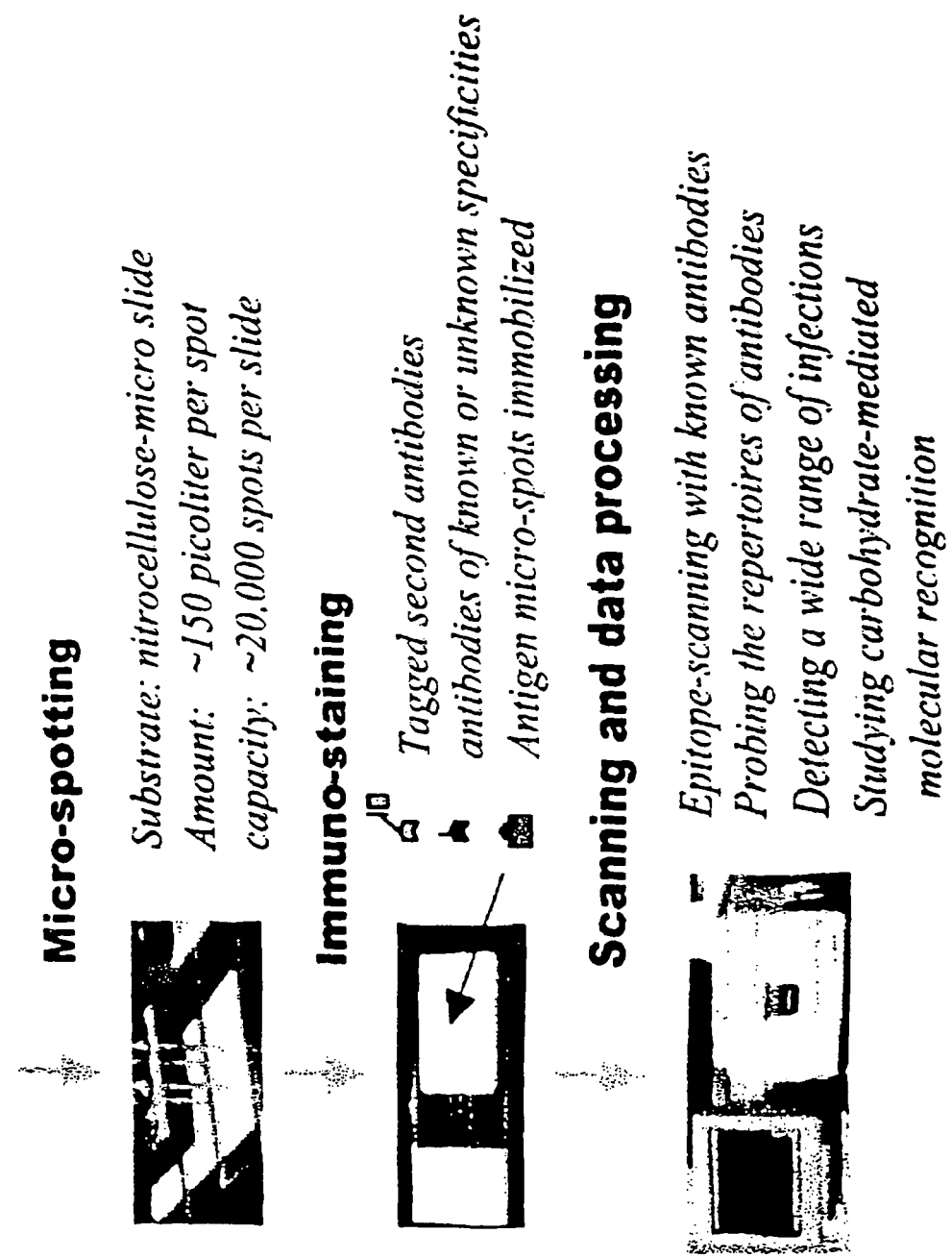

Carbohydrate-containing macro-molecules applied in FIG. 7, and anti-α(1,6) dextran mAbs, 16.4.12E (IgA/kappa) (6), 4.3F1 (IgG3/kappa) (5), and 45.21.1 (IgA/kappa) (8), were adopted from the collection of the late Professor Elvin A. Kabat of Columbia University. Purified proteins of 4.3F1, 45.21.1 and 16.4.12E were obtained by a procedure of affinity purification as described (9). The biotinylated or FITC-conjugated anti-dextran antibodies were prepared in our laboratory following standard protocols (10). The FITC-conjugated α(1,6) dextrans of molecular weight 20 kDa, 70 kDa, and 2,000 kDa, FITC-inulin, a biotinylated anti-human IgG antibody, an alkaline phosphatase-conjugated anti-human IgM, and streptavidin conjugates, were purchased from Sigma (St. Louis, Mo.). Antibodies for cell type/lineage analysis, including antibodies specific for murine CD11b/MAC1, MACS, TCR-α, TCR-β, CD3, CD4, CD5, CD8, CD19, B220, Syndecan-1, a mouse IgG3 isotype standard (A12-3), and a streptavidin conjugate of Texas Red, were from BD-PharMingen (San. Diego, Calif.). A streptavidin-Cy3 conjugate was purchased from Amersham Pharmacia (Piscataway, N.J.), and a red fluorescence substrate of alkaline phosphatase, Vector Red, from Molecular Probes, Inc. (Burlingame, Calif.).

B. Printing Carbohydrate Microarrays

A high-precision robot designed to produce cDNA microarrays (GMS 417 Arrayer; Genetic Microsystems, Inc., Woburn, Mass.) was utilized to spot carbohydrate antigens onto the glass slides precoated with nitrocellulose polymer (FAST Slides; Schleicher & Schuell, Keene, N.H.). Carbohydrate antigens were dissolved in saline (0.9% NaCl) in concentrations as specified in the Figure legends. They were printed with spot sizes of ~150 µm and at 375-µm intervals, center to center. The printed carbohydrate microarrays were air-dried and stored at room temperature without desiccant before application.

C. Staining and Scanning of Carbohydrate Microarrays

Immediately before use, the printed carbohydrate microarrays were rinsed with PBS, pH 7.4, with 0.05% (vol/vol) TWEEN® 20 (polysorbate 20) and then blocked by incubating the slide in 1% (wt/vol) BSA in PBS containing 0.05% (wt/vol) $NaN_3$ at 37° C. for 30 minutes. They were then incubated at room temperature with antibodies at an indicated titration in 1% (wt/vol) BSA in PBS containing 0.05% (wt/vol) $NaN_3$ and 0.05% (vol/vol) TWEEN 20 (polysorbate 20). Application of secondary antibodies or streptavidin conjugates is specified in figure legends. The stained slides were rinsed five times with PBS with 0.05% (vol/vol) TWEEN® 20 (polysorbate 20), air dried at room temperature, and then scanned with a ScanArray 5000 Standard Biochip Scanning System (Packard BioChip Technologies, Inc., Billerica, Mass.) and data analyzed using Quant Array version 2.1 software associated with the system.

D. ELISA and In Situ Immunofluorescence

ELISA and immunofluorescence staining were carried out as described (6, 11). The dextranase treatments were performed by a preincubation of tissue sections with dextrnase (Sigma) at 0.5 unit/ml in 100 mM potassium PBS, pH 6.0, 37° C. for 60 minutes. This condition allows a complete removal of molecules of FITC-α(1,6) dextran that were specifically trapped by immune cells in the spleen sections of α(1,6) dextran-immunized mice (11).

II. Results and Discussion

A model system for establishing carbohydrate microarray technology. The dextrans and anti-dextran antibodies (1, 2) were applied to establish methods for immobilizing carbohydrate polymers on glass slides. Dextrans are polymers composed entirely of glucose, produced mainly by bacteria of the family Lactobacillaceae and of the genera *Leuconostoc* and *Streptococcus*. Dextran molecules derived from different strains may, however, differ significantly in their glycosidic linkage compositions. Unlike proteins that are linked solely by a peptide bond, carbohydrates utilize many possible glycosidic linkages so as to diversify their structures extensively. Some dextran preparations are predominantly or solely α(1,6)-linked, forming molecules with dominantly linear chain structures; others are composed of multiple glycosidic linkages, including α(1,6)-, α(1,3)-, α(1,2)-, and others, generating heavily branched molecules (3) (Table 1). Previous immunological studies (2, 4) have demonstrated that such structural characteristics are detectable by antibodies specific for different antigenic determinants or epitopes of dextran molecules. This system is, therefore, suitable for developing methods for immobilization of carbohydrate antigens and for investigating their immunological properties in a surface-immobilized configuration.

Figure 6:
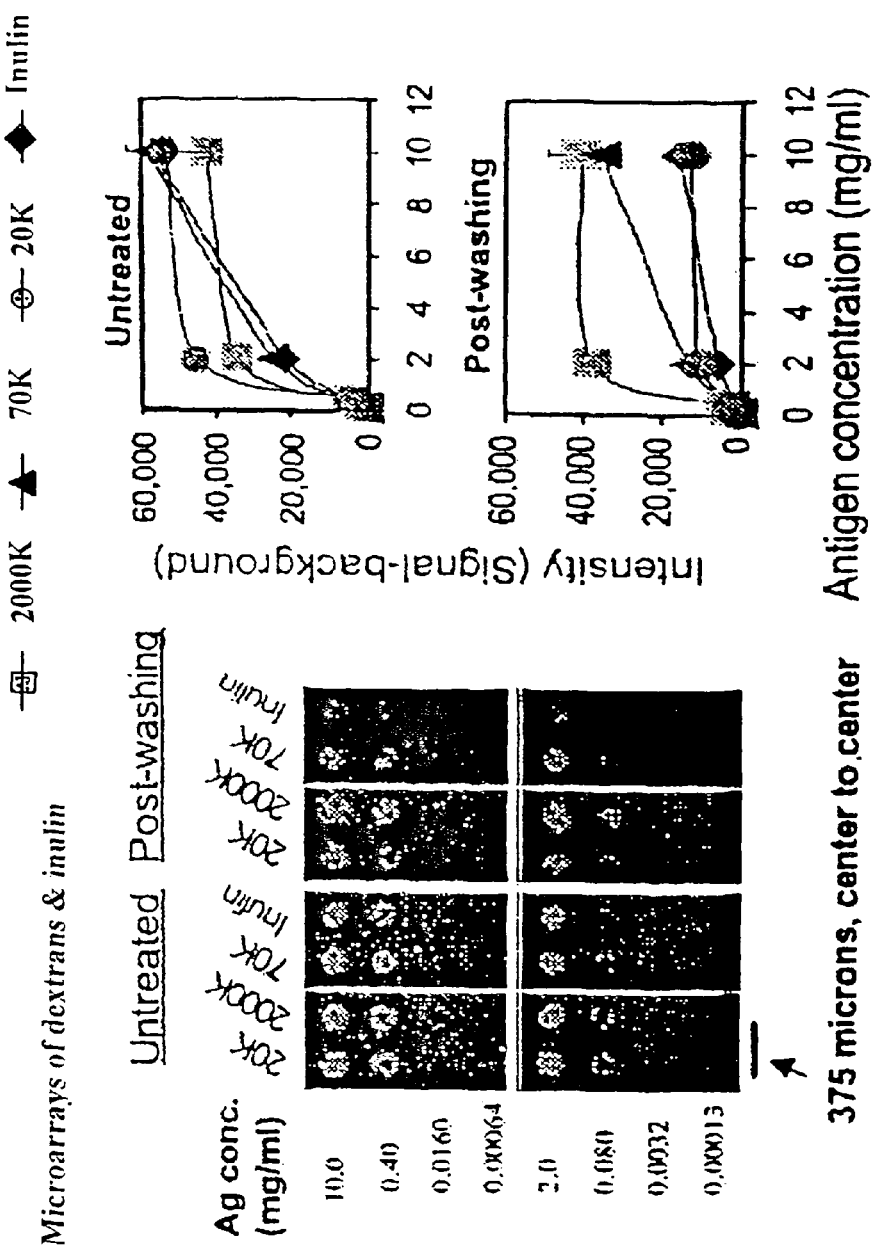

We applied the fluorescein isothiocyanate (FITC)-conjugated polysaccharides as probes to investigate whether nitrocellulose-coated glass slides can be used to immobilize microspots of carbohydrate polymers without covalent conjugation. FITC-α(1,6) dextran preparations of different molecular weights and a structurally distinct polysaccharide, inulin, were printed on the glass slides using a microprinting device to produce a carbohydrate microarray (FIG. 6A). Their fluorescent signals were then captured and quantified by a microscanning system that was developed for scanning complementary DNA (cDNA) microarrays. By analyzing the fluorescent intensities retained on the slides after extensive washing, we demonstrated that dextran preparations ranging from 20 kDa to 2,000 kDa and inulin of 3.3 kDa were all stably immobilized on the nitrocellulose-coated slide without chemical conjugation. The efficiency of their immobilization was, however, significantly influenced by the molecular weight. The larger dextran molecules were better retained than the smaller ones (FIG. 6A, B).

To investigate whether immobilized carbohydrate macromolecules preserve their antigenic determinants or epitopes, dextran preparations of different linkage compositions (3) and of different rations of terminal to internal epitopes (1, 4) were printed on nitrocellulose-coated glass slides. These preparations include N279, displaying both internal linear and terminal nonreducing end epitopes; B1299S, heavily branched and expressing predominantly terminal epitopes; and LD7, a synthetic dextran composed of 100% α(1,6)-linked internal linear chain structure. The dextran microarrays were incubated with monoclonal antibodies (mAbs) of defined specificities, either a groove-type anti-α(1,6) dextran 4.3F1 (IgG3) (5) or a cavity-type anti-α(1,6) dextran 16.412E (IgA) (6). The former recognizes the internal linear chain of α(1,6) destrans; the latter is specific for the terminal nonreducing end structure of the polysaccharide. As shown in FIG. 7A (left), the groove-type mAb, 4.3F1 (refs 5,7) bound to the dextran preparations with predominantly linear chain structures, N279 and LD7, but bound poorly to the heavily branched α(1,6) dextran, B1299S. By contrast, when the cavity-type mAb 16.4.12E (FIG. 7A, right) was applied, it bound to the immobilized dextran preparations having branches (N279 and B1299S) but not those with only internal linear chain structure (LD7). These patterns of antigen-antibody reactivities are characteristically identical to those recognized by an ELISA binding assay (FIG. 7B) and other classical quantitative immunoassays for either the groove-type (4, 5, 7) or the cavity type (4, 6) of anti-dextran mAbs. We conclude, therefore, that dextran molecules immobilized on a nitrocellulose-coated glass slide have their immunological properties well preserved. Both their nonreducing end structure, recognized by the cavity-type anti-α(1,6) dextrans, and the internal linear chain epitopes, bound by the groove-type anti-α(1,6) dextrans, are displayed on the surface after immobilization and are accessible to antibodies in an aqueous solution.

REFERENCES

1. Wang, D. & Kabat, E. A. Carbohydrate antigens (polysaccharides); *Structure of Antigens*, Vol. 3 (ed. M. H. V. V. Regenmortal) 247-276 (CRC Press, Boca Raton Fla.; 1996).
2. Wang, D. et al., The repertoire of antibodies to a single antigenic determinant. *Mol. Immunol.* 28, 1387-1397 (1991).
3. Jeanes, A. Immunochemical and related interactions with dextrans reviewed in terms of improved structural information. *Mol. Immunol.* 23, 999-1028 (1986).
4. Cisar, J., Kabat, E. A., Dörner, M. M. & Liao, J. Binding properties of immunoglobulin combining sites specific for terminal or nonterminal antigenic determinants in dextran. *J. Exp. Med.* 142, 435-459 (1975).
5. Wang, D. et al., Two families of monoclonal antibodies to α(1,6) dextran, $V_H19.1.2$ and $V_H9.14.7$, show distinct patterns of $J_K$ and $J_H$ minigene usage and amino acid substitutions in CDR3. *J. Immunol.* 145, 3002-3010 (1990).
6. Matsuda, T. & Kabat, E. A. Variable region cDNA sequences and antigen binding specificity of mouse monoclonal antibodies to isomaltosyl oligosaccharides coupled to proteins. T-dependent analogues of α(1,6)dextran. *J. Immunol.* 142, 863-870 (1989).
7. Chen, H. T., Makover, S. D. & Kabat, E. A. Immunochemical studies on monoclonal antibodies to stearyl-isomaltotetraose from C58/J and a C57BL/10 nude mouse. *Mol. Immunol.* 24, 333-338 (1987).
8. Sharon, J., Kabat, E. A. & Morrison, S. L. Association constants of hybridoma antibodies specific for α(1-6) linked dextran determined by affinity electrophoresis. *Mol. Immunol.* 19, 389-397 (1982).
9. Lai, E. & Kabat, E. A. Immunochemical studies of conjugates of isomaltosyl oligosaccharides to lipid: production and characterization of mouse hybridoma antibodies specific for stearyl-isomaltosyl oligosaccharides. *Mol. Immunol.* 22, 1021-1037 (1985).
10. O'Shannessy, D. J., Dobersen, M. J. & Qarles, R. H. A novel procedure for labeling immunoglobulins by conjugation to oligosaccharide moieties. *Immunol. Lett.* 8, 273-277 (1984).
11. Wang, D., Wells, S. M., Stall, A. M. & Kabat, E. A. reaction of germinal centers in the T-cell-independent response to the bacterial polysaccharide α(1-6)dextran. *Proc. Natl. Acad. Sci.* USA 91, 2502-2506 (1994).

Third Series of Experiments

I. Introduction

A microbial infection may expose and release multiple antigenic substances to a host, eliciting a comprehensive host immune response, including a B cell response, which produces specific antibodies, and a T cell response, resulting in specific T cell activation and cytokine production. There is also an activation of macrophage, dendritic cells and other accessory cells, leading to production of differential profiles of cytokines and inflammation factors. Some microbial substances are lethal to a host upon their immediate release or after interacting with host cells or cellular factors. The interplay of different types of host cells and multiple protein factors and their interaction with the invading pathogen determine the progress and consequence of a microbial infection. For example, in an anthrax infection, the pathogen *Bacillus anthracis* may expose and release a number of antigens of distinct structural characteristics to a host, eliciting a comprehensive picture of a host response (FIG. 8).

To better understand the pathogenesis mechanisms of an infectious disease, it is crucially important to monitor the full-spectrum of the multi-parameter host responses and identify the characteristic patterns of the response. Monitoring such a complex host response and host-microbe interaction has long been a challenge to biomedical scientists and clinicians. Many antigen-antibody binding assays are currently in use for clinical diagnosis of infectious and non-infectious diseases. These include the classical direct immunoassays, such as, immunodiffusion, immunoelectrophoresis, agglutination and immunoprecipitation, and recently developed methods, including immunofluorescence, radioimmunoassay (RIA), enzyme-immunoassay (EIA) and western blot. These approaches take advantage of the specificity of antigen-antibody interaction but are designed to operate on a one-by-one basis.

Rapid progress of the genome sequencing projects has led to the development of a generation of high throughput technologies for biological and medical research. These include the nucleic acid-based microarrays (6,7) or DNA chips (8), and the protein-based microarrays (9,10). Our recent efforts have been focusing on the development of a carbohydrate and protein-based microarray technology to extend the scope of biomedical research on carbohydrate-mediated molecular recognition and anti-infection responses (see reference 11 and next section for our most recent progress).

The microspot format of surface displaying biological molecules has the advantage of achieving a highly sensitive and simultaneous detection of multiple binding partners in solution. Since the amount of molecule in the solution phase that is required for saturating the surface immobilized microspots of molecules is considerably small, binding can be achieved with a relatively lower molar concentration of molecules in solution. In brief, it is believed that the smaller microspot is better than the bigger spot in its sensitivity of detection in an assay system (12,13).

(A) Category A Pathogens and their Genomic Information

High-priority infectious agents that pose current risks to our national security include multiple microbial pathogens known as Category A pathogens, such as *Bacillus anthracis* (anthrax), *Clostridium botulinum* (botulism), *Yersinia pestis* (plague), Variola virus (smallpox), *Francisella tularensis* (tularemia) and viral hemorrhagic fevers (Lassa virus, Ebola virus, Marburg virus and Lymphocytic Choriomeningitis virus). An assay system that allows detection and characterization of these pathogens in a single assay using limited clinical specimens is currently unavailable.

A great deal of genomic information is available for numerous pathogens (14-16), providing many opportunities to the field of infectious disease research. The identification of candidates from a large repertoire of genes, including a large panel of genes whose function is unknown, for developing diagnostic protein biochip s is, however, a current challenge. As detailed below, we have established a strategy to facilitate the selection and identification of genes that have potential to serve as novel molecular targets for vaccination and diagnosis. Information provided by whole genome sequencing of microbes may also boost progress in the molecular engineering of artificial species of desired characteristics. There is also concern that the release of laboratory amplified genetic material to the environment may facilitate the natural occurrence of recombinant or newly evolved microbial species or strains. Such emerging microbes could be either beneficial or harmful to public health depending on the nature of the microorganism as well as the way by which they are utilized. Therefore, in designing a high throughput immunoassay one must consider the detection of existing pathogens as well as their mutants or recombinant forms. This goal is achievable if a panel of antigens of a given microbe and/or their specific antibodies are applied to produce a diagnostic biochip to detect multiple molecular targets of the pathogen. Applicants have tested the feasibility of this proposal by printing a panel of HIV-1 proteins on a single chip to monitor the HIV-1 infections by different classes or clades of HIV-1 viruses (see FIGS. 11 and 12).

(B) Antigen-Based Biochip

An antigen biochip is designed to detect and quantify antibodies in body fluids. During infection, whether viral, bacterial, fungal, or parasitic, the host usually responds with formation of antibodies, which can be detected by modification of any of the methods used for antigen detection. The formation of antibodies and their time course depends on the antigenic stimulation provided by the infection. Recognition of these patterns provides us with evidence of recent or past infection. Establishing a biochip to display a large panel of microbial antigens and the host derived autoantigens will substantially extend the scope of biomedical research on the biological relationship between host and microorganism, as well as understanding the molecular mechanisms of infectious diseases. Both carbohydrate antigens and protein antigens can be of importance for the design and production of a diagnostic biochip.

Carbohydrate structures of microbial origin, including polysaccharides, glycolipids and glycoproteins, frequently serve as the main antigenic structures to which host cells recognize and mount a response (17). A single microbial antigen may, however, display multiple antigenic determinants, with one or a few of them predominating in a given infection. For example, a relatively simple microbial polysaccharide, $\alpha(1,6)$ dextran N279, displays both the internal linear chain and terminal non-reducing end structures as distinct antigenic determinants. When the polysaccharide was injected to a Balb/c mouse, it elicited a predominant antibody response directed to the internal linear chain epitope of $\alpha(1,6)$dextran. The internal linear chain epitope is thus defined as a dominant antigenic determinant to the host. The antibodies elicited were solely or dominantly of the groove-type anti-dextran. In this case, the terminal non-reducing end structure is apparently the minor antigenic determinant. A dominant antigenic determinant should, therefore, be placed as a high priority to serve as a target for vaccine design or for developing an immunoassay for diagnosis.

Identifying a minor antigenic determinant is, however, also important since there is the possibility that a dominant antigenic structure is not suitable for vaccination or diagnostic application; whereas, a minor antigenic determinant may serve as a molecular target for these applications. Some microbial antigens may share or mimic host components. This is known as antigenic cross-reactivity. For examples, a $(1\rightarrow8)$NeuNAc in the capsule of the group B meningococcus and of *E. coli* K1 is found on glycoproteins and gangliosides of human tissues, complicating the application of the capsular polysaccharides for vaccination, especially in infants who have expression of polymeric forms of the carbohydrate structure. There are also circumstances that a dominant antigenic structure can be useful for diagnosis but not for vaccination. For example, the Gag p24 protein of HIV-1 elicits a dominant antibody response in most AIDS patients. Detecting anti-Gag antibodies has diagnostic value. These antibodies, however, have no HIV-1 neutralization activity since Gag is not expressed on the surface of the HIV-1 virus. Even for the envelope protein, gp120 of HIV-1, which is surface displayed and accessible to antibody recognition, there are only a few epitopes of the glycoprotein to which antibodies can be effective in virus neutralization (18).

With current immunological advances, converting a minor antigenic determinant into a dominant one is technically achievable. For example, the antigen may be coupled with a carrier molecule, forming a highly antigenic conjugate molecule. As demonstrated with a model antigenic system $\alpha(1,6)$dextran, an isomaltotriose (IM3), which is derived from the polysaccharide $\alpha(1,6)$dextran, can be coupled to BSA or KLH to produce a semi-synthetic glycoprotein to display the minor antigenic determinant of the polysaccharide, i.e., the terminal non-reducing end epitopes of α(1,6)dextran. When this glycoconjugate was injected to Balb/c, a dominant antibody response to the terminal antigenic determinant is induced. Immunization with such an artificial semi-synthetic glycoconjugate is now well known as the conjugate vaccine. A notable example is vaccination with the protein-conjugates of *Haemophilus influenza* type b polysaccharide that resulted in the decline in the incidences of *H. influenza* meningitis and other infections in infants and children (19,20). The presence of polysaccharides and glycoproteins in *Bacillus anthracis* has been recognized for some time (4, 21,22). Whether these carbohydrate structures are suitable targets for anthrax vaccination is, however, an open question.

Recognition of cross-reactive antigenic determinants is frequently shown to be of biological and medical significance. There are a number of documented cases in which microbial antigens mimic the structures of host components, assisting a microbe to escape from a host's immune defense (23,26). Such mimicking microbial antigens may also induce autoimmune disorders and contribute to the pathogenesis of an infectious disease (23,27). Identification and characterization of such antigenic structures may lead to a better understanding of the molecular mechanisms of infectious diseases.

Antigenic structures that are not expressed on the surface of a microorganism also have an important diagnostic value. For example, detection of antibodies that are specific for the surface antigen of hepatitis B (HBsAg) may indicate an early viral infection or a successful vaccination; detecting antibody specificities to multiple viral antigens, such as surface antigen (HBsAg) plus core antigen (HBcAg) or HBsAg plus a relevant e antigen (HBeAg) suggests an active infection or the progression of the disease (28,29). A microbial pathogen, either a virus or a bacterium, may release multiple antigenic substances that trigger host antibody responses. In an early infection, as an initial immune response, the antibodies elicited are mainly those bound to the surface antigens and are predominantly IgM antibodies. With the progression of an infectious disease, for example in an AIDS patient a few months post-serum conversion, a large panel of IgG antibodies with different specificities, including anti-gp120 (envelope protein) and anti-Gag p55 polyproteins of HIV-1, can be detected in the serum of the patient. Thus, applying a combination of surface and non-surface antigens on a biochip for diagnosis can assist in the recognition of the stages or steps of an infection and provide information to predict disease progression and to evaluate the efficacy of a therapeutic agent or strategy.

Development of drugs or therapeutic strategies against microbial infection requires a better understanding of the pathogenic mechanisms of an infectious disease. For example, the anthrax toxin is lethal upon its activation. This process involves multiple steps of molecular and cellular interactions of anthrax proteins, host cells and protein factors (1-3). The protective antigen of anthrax, named PA, is an integrated component of the lethal toxin of *Bacillus anthracis*. It binds to a specific cellular receptor and forms toxic, cell bound complexes with edema factor (EF) and lethal factor (LF) (1-3). This understanding leads to the development of a polyvalent inhibitor-based therapeutic strategy to protect a host from lethal attack by the toxin (5). Technically, it is of crucial importance to identify the structural moieties or epitopes that play key roles in forming the toxic complex or in the interaction of PA and its macrophage receptor. Generally speaking, the epitopes of a protein or a glycomer that interact with or are recognized by their partners are surface exposed and are, therefore, recognizable by specific antibodies. Identifying such antigen-antibody pairs is of crucial importance. Such pairs could serve as specific probes for the screening of smaller molecules to identify drug candidates that may block the effect of the anthrax toxin. Development of an antigenic structure-based biochip of large capacity and diversity would facilitate efforts to identify such key structural elements and screen for their specific antibodies for drug development.

Thus, for the purpose of diagnosis, vaccination and drug development, it is important to recognize the dominant and minor antigenic determinants for a specific anti-infection antibody response to characterize the specificity and cross-reactivity of an antigenic structure; and to have a full-panel scanning of the repertoires of antibody specificities elicited by an infection. Such investigation has been impossible owing to a lack of a high throughput, multi-parameter assay system. Developing a carbohydrate and protein-based biochip to present a large repertoire of antigenic structures, including those displaying a single antigenic determinant on each microspot, would substantially facilitate these investigations.

(C) Antibody-Based Biochip

In principle, an antigen-based biochip is designed to detect and quantify specific antibodies and therefore, diagnose an infection. This method is not for the detection and quantification of antigens that are released from an infectious agent. Detecting microbial antigens in serum or other body fluids is generally more difficult than detecting antibodies. The former has, however, higher diagnostic value than the latter. It is, therefore, necessary to establish a highly sensitive antibody-based microarray to detect microbial antigens.

The complexity of a host anti-infection response further challenges the development of a multi-parameter immunoassay for characterizing infectious diseases. During an infection, a large panel of antigenic substances of distinct structural characteristic, including protein, polysaccharide, glycolipid, glycoproteins and nucleic acid, may be released to trigger the host immune response. These substances may differ significantly in their immunological properties and, therefore, elicit characteristic patterns of host responses. For example, protein antigens fail to elicit antibody responses in mice lacking a thymus but polysaccharides and other macromolecules with repetitive antigenic determinants can induce unimpaired antibody responses in these mice (30-32). The former are termed T-dependent (TD) antigens and the latter are T-independent (TI) antigens. The differences of TI- and TD-antigenic responses, which are recognizable by in vitro immunoassay, include a series of humoral factors, such as antigen specific antibodies, their Ig-isotypes, cytokines and other inflammation factors.

To better understand infectious disease, the full spectrum of anti-infection responses must be studied. These include specific antibody responses as well as the antigen-non-specific cytokine responses and other host responses. Cytokines are soluble proteins or glycoproteins, which play a critical role in controlling development or differentiation of lymphocytes and in regulating their anti-infection responses. For example, a microbial infection or vaccination may activate certain sub-types of T cells, either T helper 1 (Th1) cells or T helper 2 (Th2) cells. These specialized Th cells can produce unique profiles of cytotokines. Th1 secrete IL-2, IL-3, TNF-α and IFN-γ; Th2 secrete IL-3, IL-4, IL-5, IL-6, IL-9, IL-10 and some TNF-α. For anti-infection responses, induction of IgA-antibodies at mucosal sites is of critical importance T cells and their cytokines, have been shown to play a critical role in various stages of IgA response (33-35), including induction of Ig class switching of IgM to IgA and of terminal differentiation of IgA-committed B cells. Many researchers believe that IgA responses are highly Th-2 dependent (36-39), since there is evidence that Th2 cytokines, such as IL-4, IL-5 and IL-6, are required to induce terminal differentiation of IgA-committed B cells. By contrast, the Th1 cytokine, IFN-γ, antagonizes IL-4 in its IgA induction.

Our current efforts focus on the development of high throughput post-genomic technologies to extend the scope of biomedical research on human infectious diseases and the human immune response. A carbohydrate and protein-based microarray has been prepared, making it possible to display a large collection of antigens on a single biochip for probing the repertoires of antibody specificities and for studying carbohydrate and protein mediated molecular recognition on a large scale. This microarray platform has achieved the sensitivity to detect a broad range of human antibodies with as little as a few microliters of serum specimens and has reached the capacity to include antigenic preparations of most common pathogens. This technology is, therefore, readily applicable for large-scale production of an antigen/antibody microarray. In this invention, we describe the establishment of a detailed procedure for the industrial scale production of diagnostic biochips to enable simultaneous detection and characterization of a wide range of microbial infections, which include all listed Category A biological warfare agents. These include (a) the design and production of a carbohydrate-based microarray composed of microbial polysaccharides, its derivatives and a large panel of carbohydrate-containing macromolecules of distinct sugar structure; (b) a procedure to take advantage of the genomic information available for specific pathogens to design and produce proteomic microarrays to identify novel molecular targets for vaccination, diagnosis and drug development; (c) a method to produce an antibody-based microarray system to monitor microbial antigens in vivo and in vitro and to enable full-panel scanning of cytokines and other inflammation factors with limited amount of clinical specimens; and (d) the design and production of highly sensitive diagnostic biochips, including Diagnostic Biochip A and B for the rapid detection of all the biological warfare agents listed by the CDC as Category A pathogens and Diagnostic Biochip C for simultaneous detection and characterization of a wide range of common infectious diseases, which are caused by about 200 human pathogens.

II. Methods to Produce Large Capacity and High-Density Biochips (~30,000 Microspots/Microchip)

Compared with DNA- and protein-based microarrays, the carbohydrate microarray technology has certain technical advantages and disadvantages. An obvious advantage is that the purified polysaccharides are generally stable in various conditions, either as dried solid or in aqueous solution, at room temperature or at 4° C. in storage. Unlike protein microarrays, wherein protein-denaturing and/or conformational alteration in microarray printing and storage is a major challenge to the technology, there is no such serious concern for most (if not all) carbohydrate antigens. A disadvantage of the carbohydrate microarray technology is that methods for high throughput production of carbohydrate macromolecules or complex carbohydrates, which is equivalent to the PCR for amplifying DNA or the cloning and expression method for producing proteins, are yet to be developed. Classical methods to obtain pure carbohydrate antigens include (a) isolation and purification from biological materials, such as cells, tissues or biological fluids; (b) chemical synthesis; and (c) enzymatic in vitro synthesis. A Rapid progress in establishing high throughput technology for the in vitro synthesis of carbohydrate macromolecules or complex carbohydrate molecules is most likely unexpected. The availability of purified carbohydrate antigens is, therefore, a potential rate-limiting factor to the carbohydrate microarray industry.

Our optimized methods for printing microarrays allows one: (i) to reduce amount of antigen needed for microarray printing; (ii) to increase the detection sensitivity and biochip capacity; (iii) to reduce the time that is necessary for a microarray printing cycle; (iv) to prevent cross-contaminations in printing microarrays; and (v) to reduce the cost of producing a diagnostic biochip substantially.

(A) Printing Microspots of Smaller Sizes and High-Densities

The general printing procedure is schematically illustrated in FIG. 9. A high-precision robot designed to produce cDNA microarrays was utilized to spot carbohydrate antigens onto glass slides that were pre-coated with nitrocellulose polymer. In addition, the following were also used:

a) STEALTH 3 pins for printing microspots 150 microns in diameter on nitrocellulose slides. This allows the arraying of 10,368 spots per FAST-slide with spot intervals of 250 micron, center-to-center; and b) STEALTH 2.5 pins for printing spots at about 100 microns in diameter on the surface. 28,800 spots can be patterned on a single FAST slide. If each antigen preparation is printed as an array of four identical microspots, (See FIG. 12 below), 7,200 antigenic molecules can be included on a single slide. This system has, therefore, enough capacity to include most known human microbial pathogens and tumor-associated antigens.

III. Diagnostic Biochips (A) Diagnostic Biochip A

This biochip is designed to enable the simultaneous detection of all Category A infectious diseases. In its clinical application, two-step staining is required. A number of carefully selected pairs of antigen and antibody are be printed on slides for each pathogen. The immobilized antigen serves as a probe to detect antibody in solution; the surface displayed antibody is used to capture a specific antigen in the solvent. This assay is, therefore, capable of detection of both antigens and antibodies in a single assay. Since an immobilized antigen may display multiple antigenic determinants, a microspot of antigen may capture antibodies that recognize different antigenic determinants expressed by the antigenic molecule. This makes the biochip system highly sensitive. Its detection specificity is, however, at the level of the antigenic molecule but not at the level of a single antigenic determinant. In case an antigen expresses a cross-reactive antigenic determinant, its detection specificity will be reduced (See the design of diagnostic biochip B for further discussion).

(1) 8-Chamber Sub-Arrays (See FIG. 10):

Each micro-glass slide contains eight well-separated sub-arrays of identical contents. There are 600 microspots per sub-array, with spot sizes of approximately 200 micron at 300 micron intervals, center-to-center. A single slide is, therefore, designed to enable eight detections;

(2) Contains:

(a) Microspots: Each 600-spot sub-array is composed of carbohydrate and protein antigens, as well as antibodies specific to microbial antigens. The immobilized antigens will allow for the detection of human antibodies elicited by an infection; whereas immobilized antibodies are for the detection of microbial antigens;

(b) Repeats and dilutions: Each antigen/antibody will be printed at 0.5-1.0 mg/ml and at one to ten dilution of the initial concentration for the second concentration. Each preparation at a given concentration will be repeated three times; and (c) Antibody isotype standard curves: Human antibodies of IgG, IgA and IgM isotype of known concentrations will serve as standard curves for antibody detection and normalization.

(3) Assay Mechanisms:

(a) Detection of antibodies: use of immobilized antigens to capture antibodies in solution, which are then recognized by the tagged anti-human antibodies. In principle, this is an indirect immunoassay;

(b) Detection of microbial antigens: use of immobilized antibodies to capture antigens in solution and application of the tagged antibodies specific for the corresponding antigens to identify the captured antigens. This is known as a "Sandwich" immunoassay.

(4) Application and Staining Procedure:

Use of 0.5-1.0 microliters of serum specimens for the detection of a) specific antibodies in body fluids and b) presence of antigens in vivo and in vitro. Two steps of staining and approximately 5 hrs is required to complete the biochip analysis.

(5) Specificity & Sensitivity:

a highly sensitive biochip system with specificity at the level of an antigenic molecule.

(B) Diagnostic Biochip B

This biochip is designed to enable the rapid diagnosis of the Category A infectious diseases, which requires only a single step of staining in clinical diagnosis. The time required for a biochip assay is, therefore, substantially shorter. Competitive immunoassay is used for rapid diagnosis. A competitive immunoassay requires an antigen/antibody pair. Either antigen or antibody can be immobilized on the solid surface, which will then interact with an antigen or antibody in solution. The immobilized antigen and tagged antibody in solution forms a specific probe to detect both antigen and antibody in clinical specimens. The free-antigen or antibody competitively inhibits the binding of the tagged antibody to the antigen immobilized on the solid surface. Key characteristics of this "competitive" one-step biochip that differ from Diagnostic Biochip A are summarized below:

(1) Chip Contents:

A panel of carefully selected microbial antigens, whose specific antibodies are available, will be printed on the chip with the method described above.

(2) Assay Mechanisms:

The free antigens or antibodies can compete with the labeled antigen or antibody to bind the immobilized antigens or antibodies. Given that antibodies are generally more stable than other protein molecules in solution and are suitable for standardized production, printing antigen on a series of glass slides and using fluorescent-tagged antibodies for staining is preferred. If a clinical specimen in question contains a specific antibody for the target antigenic determinant or the antigen, the binding of the tagged antibody to the antigen will be competitively, inhibited.

(3) Application and Staining Procedure:

One-step staining of the biochip allows detection of specific antibodies in body fluids of antigens in vivo and in vitro. The time required for biochip analysis, is therefore, reduced by 4 hours.

(4) Specificity & Sensitivity:

Diagnostic Biochip B is a highly sensitive and specific biochip system. Its specificity is at the level of a single antigenic determinant.

(C) Diagnostic Biochip C

Diagnostic Biochip C is composed of a large repertoire of carbohydrate and protein antigens as well as antibodies. This is a largely extended Diagnostic Biochip A. This biochip makes it possible to diagnose and characterize a wide range of microbial infections using a few microliters of serum specimen. This microarray has the printing capacity to include most common pathogens. Practically, it is limited by the availability of specific antigen preparations and their antibodies. 1000-2000 distinct antigens and antibodies can be printed on the chip. This enables a simultaneous detection of about 300 microbes, which include about 50-100 human pathogens. General properties of the master microarray are summarized as follows:

(1) Capacity:

15,000-20,000 microspots per micro-glass slide, with spot sizes approximately 150 micron in diameter and at 200-micron intervals, center-to-center.

(2) Diversity:

1000-1500 distinct antigenic preparations, about 100 antibodies specific for microbial antigens and about 30-50 antibodies for detecting human cytokines and other inflammation factors.

(3) Repeats and Dilutions:

Each antigen has four dilutions (0.5 mg/ml to begin with) and each dilution has three repeats.

(4) Antibody Standard Curves:

Human antibodies of IgG, IgA and IgM isotype of known concentrations are printed on the chip to produce standard curves for normalization calculation of the titer of the specific antibodies of a given isotype captured by the carbohydrate antigen.

(D) Diagnostic Biochip D

This biochip is composed of about 4,000 microspots of antigen and antibody preparations. Each antigen or antibody preparation of a given dilution was printed with four repeats in a vertical line of microspots on the biochip. This allows us to visually observe and statistically analyze the reproducibility of microarray printing and staining. The significance and sensitivity of antibody detection for each antigen at a given antigen concentration can also be statistically calculated. Some preparations, for example the gp120 glycoprotein of HIV-1 as highlighted in a square in FIG. 11, were printed from left to right in a series dilution of one to five, beginning at 0.5-1.0 mg/ml and with four dilutions thereafter. These biochips were stained with the normal or HIV-1 infected human serum specimens with the methods described above. Pictures of the ScanArray visualization of the multi-color fluorescent staining of biochips are shown in FIG. 11.

In this experiment, we have demonstrated that: (a) a procedure for microarray printing, antigen/antibody immobilization and antibody staining is precisely reproducible. On the same biochip, the correlation factors of data crossing different microspots of the same preparation is in the range of (0.98) to (1.00); (b) detection of human serum antibodies by this method is highly sensitive. A few microliters of serum specimen allows a full-panel scanning of the repertoires of human antibodies of different Ig-isotypes in a single assay. A large repertoire of antibody specificities were recognized in the normal and HIV infected individuals; (c) the specificity of this system is illustrated by recognizing the epitope-binding specificities of monoclonal anti-dextran antibodies and by specific detection of human serum antibodies for the gp120 glycoproteins and gag p24 of HIV-1 in AIDS patients; (d) a large repertoire of microbial antigens can be patterned on a single micro-glass slide, reaching the capacity to include most common and conditional pathogens; and (e) a biochip-based high throughput technology requires a strong bioinformatic presence to support it. While one may need a day to perform a biochip assay for a given clinical specimen, one may need many days to process the large amount of data produced by the biochip analysis. Developing advanced computer algorithms to facilitate this process is of equal importance with improving the hardware of the biochip technology.

(E) Diagnostic Biochip E

Figure 12:
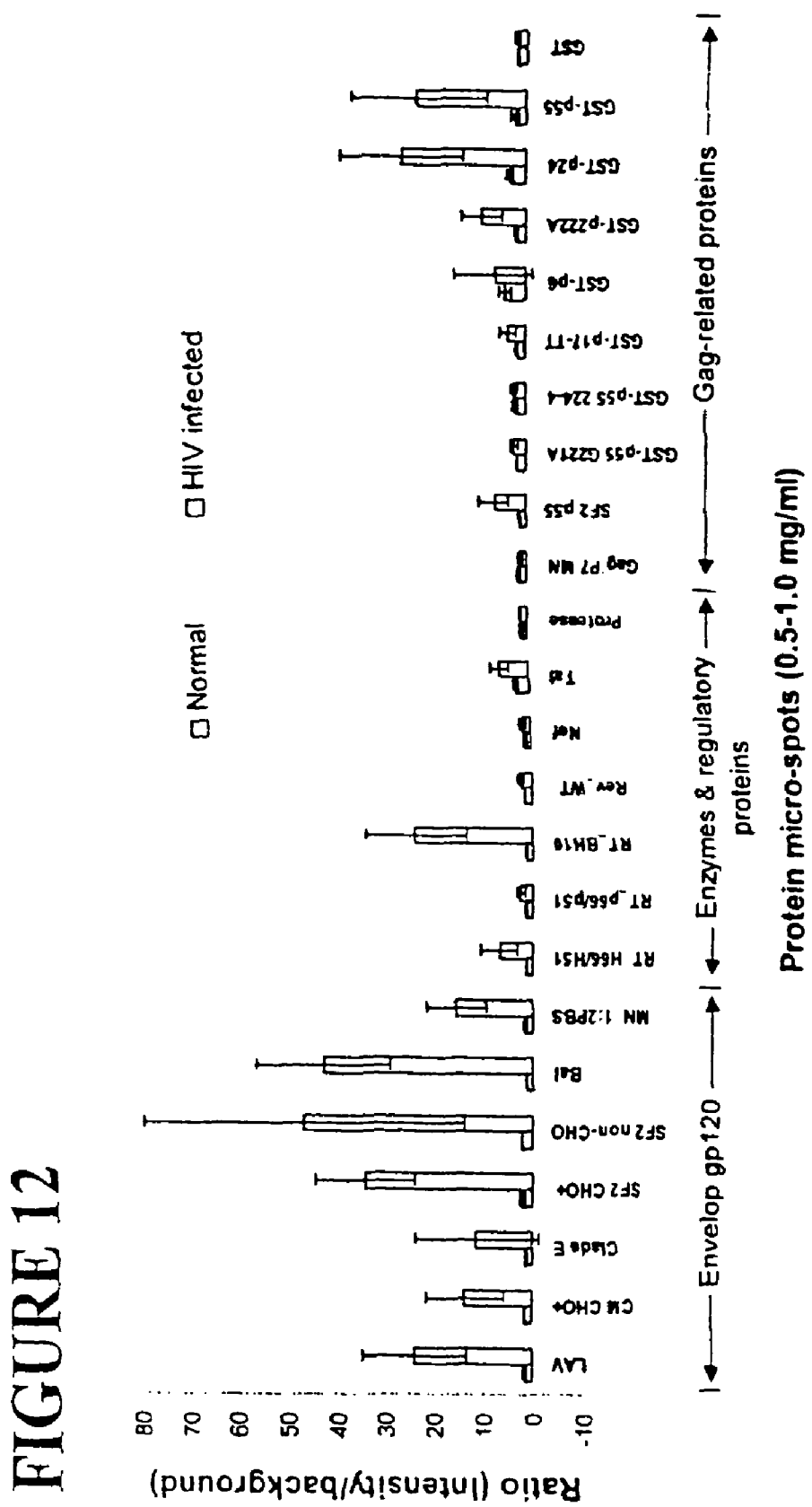
Figure 13:
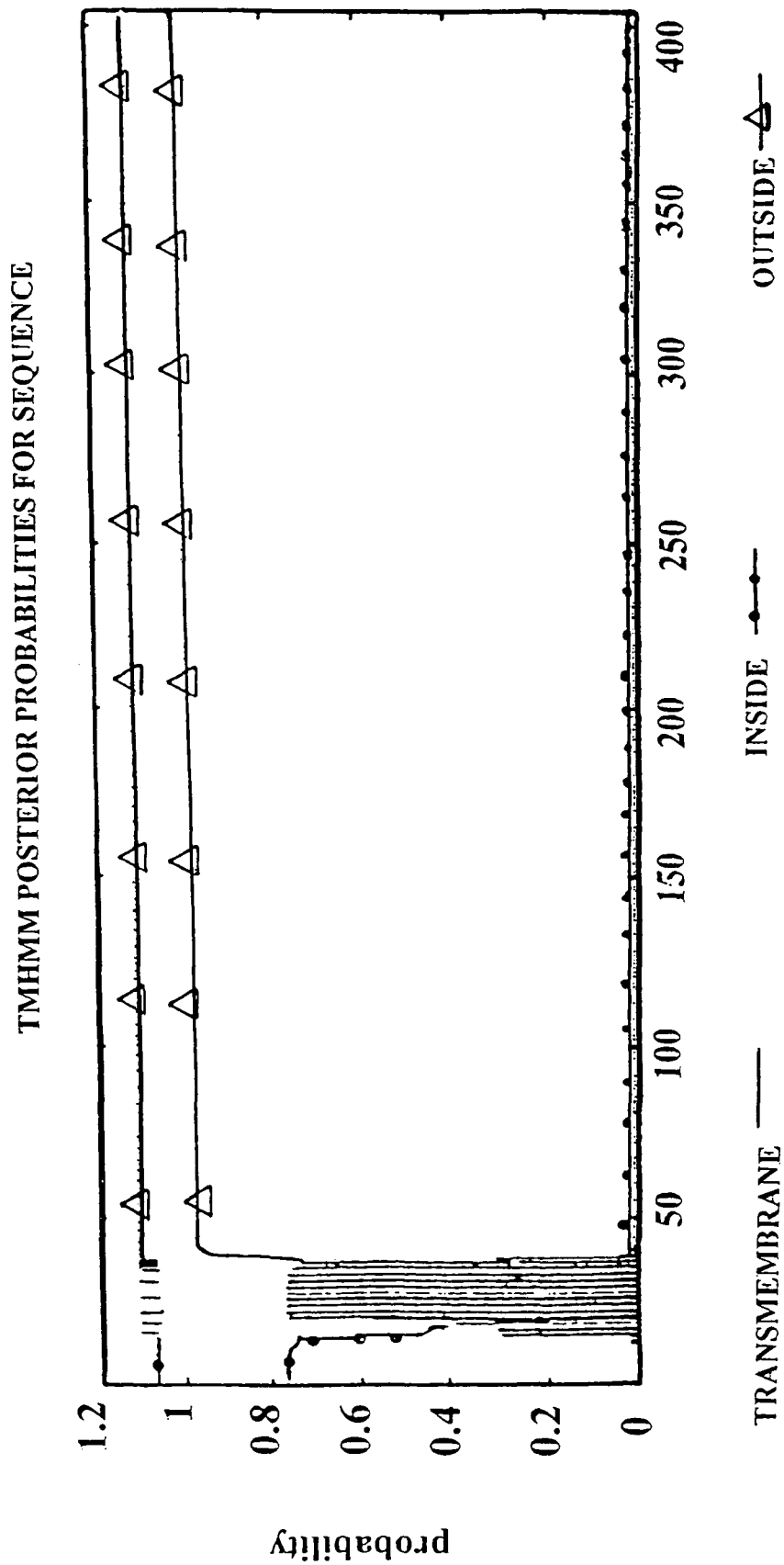

This is a proteomic microarray-based biochip produced with the microarray platform used to produce carbohydrate microarrays. Discovery of a large repertoire of genes in the genome of microorganisms has provided novel targets for vaccination, diagnosis, and drug development against microbial infection. To take advantage of this, HIV-1, whose genome is relatively small and has been completely sequenced, is used herein to establish the protein-based microarray technology. A large panel of purified HIV proteins, including gp120 proteins derived from different clades of HIV-1, Gag p55, p24, P6, P7, P17 and/or their E. coli expressed GST-fusion proteins, Tat, Nef, Integrase, and reverse transcriptase (RT), were printed and immobilized on the chemically modified glass slides. These protein chips were then applied to probe antibodies in normal and AIDS patients. As shown in FIG. 12, most HIV proteins printed on the chip gave positive detection of antibodies in HIV-infected individuals but not in normal controls, showing the sensitivity and specificity of this protein chip.

Therefore, we conclude that: (a) these positively stained HIV proteins were stably immobilized on the biochip and retained their immunological properties; (b) the protein microarray system has reached the sensitivity to probe the repertoires of antibodies in clinical specimens; and, most importantly, (c) it is feasible to introduce a large panel of protein products of genes, including both surface and non-surface proteins, and newly discovered genes, for our biochip production and diagnostic application. This finding is significantly important since it allows us to explore the application of genomic information and genetic material that has been accumulated by the genome projects.

(F) Diagnostic Biochip F

This is an antibody-based microarray and is designed to enable a full-panel scanning of human cytokine. Cytokine detection at the protein level is technically difficult. These proteins are potent biological agents that function at very low concentrations (7). Some cytokine molecules are unstable after secretion or activation (7). A highly sensitive specific assay is required to detect these molecules. A method currently used for cytokine detection, either ELISA-based assays or radioimmunoassays, takes advantage of the Sandwich-antibody assay. Specifically, the first cytokine-specific antibody is immobilized on a solid surface to capture cytokine in solution and then the second anti-cytokine antibody is applied to detect the surface-immobilized cytokine. The second anti-cytokine can be biotinylated, allowing signal amplification with a labeled Streptavidin. These methods are highly sensitive but limited in detecting a cytokine on a one-by-one base.

We have extended our microarray platform to produce the antibody-based biochips. The arrayed antigens allow specific capture of antibodies from body fluids and the antibodies immobilized on the glass chip can be used to detect soluble antigens and host factors, such as cytokines and other inflammatory factors. We immobilized a panel of anti-dextran mAbs at a concentration of 0.5 mg/ml on a set of glass slides. These include nitrocellulose-coated glass slides, polylysine treated slides, silane-treated glass slides and untreated, precleaned glass slides. These slides were then reacted with the fluorescence-tagged dextran preparations of distinct structures. Only the nitrocellulose-slides showed spots of specific fluorescent signals. Thus, anti-dextran mAbs were immobilized on the nitrocellulose-glass slide and retained their antigen binding specificities.

We further addressed whether the nitrocellulose-coated slide can be applied to immobilize antibodies on a chip for long-term storage. To investigate the condition for the preservation of antibody microarrays, we placed these microarrays under different conditions: (a) in an air-dried condition at room temperature; and (b) in a blocking solution, stored at 4'C. After six months, we stained these antibody microarrays with tagged antigens. We found that both group (a) and group (b) slides preserved antigen-capturing activities and specificities. Signals obtained by the two groups differ, however, significantly, with the latter much stronger than the former. These experiments have indicated the potential of the nitrocellulose-based non-chemical immobilization method for antibody microarray production.

An antibody microarray for a full-panel scanning of human cytokines was prepared. Polyclonal and monoclonal antibodies specific for human cytokines are currently available through various resources, providing a strong base for developing an antibody microarray to enable a highly sensitive, high throughput, full-panel cytokine scan.

We have found that the current microarray platform favors detection of IgG antibodies but not IgM antibodies in solution. The former is an immunoglobulin (Ig) monomer and the latter is an Ig pentamer. One theory for this result is that the pore size of FAST slides is too small to allow IgM antibody to enter and bind antigen immobilized in the deeper layer of the 3D nitrocellulose network structure (see ref. 40 for a 3D illustration of the nitrocellulose coating). This finding is of significance since it provides information for the development of an improved surface for producing a diagnostic biochip.

IV. Methods to Search and Identify Novel Carbohydrate Targets for Diagnosis and Vaccination A large collection of carbohydrate containing macromolecules are printed on the nitrocellulose-coated slides and then the carbohydrate microarrays are stained with antibody preparations or lectins to probe the microspots that display the antigenic determinants in question. The monoclonal and polyclonal antibodies elicited by a microbial antigen or by a pathogen, as well as serum specimens of an infected individual are all useful reagents for these analyses. A positively stained microspot indicates the presence of a target molecule or antigenic determinant. Further characterization of this antigen preparation could lead to the identification of a suitable diagnostic molecule for a given infectious disease.

We have employed B. anthracis as a model pathogen to illustrate our research approach, from the identification of a target molecule to the further characterization of the structure using our carbohydrate microarray technology.

(A) B. anthracis Related Carbohydrate Antigens as Diagnostic Molecular Targets

Carbohydrate structures present in B. anthracis are potential molecular targets for vaccine development and for diagnostic application. These carbohydrate structures include glycoproteins and polysaccharides. Glycoproteins are expressed by the dormant spore of B. anthracis and are recognizable by specific lectins, such as Glycine max (41). Since the spore surface interacts with the host initially in an anthrax infection, these structures are likely the targets for host recognition and antibody responses. They are therefore important for both vaccination and diagnosis. Polysaccharides are expressed by the germinating spores of B. anthracis, which are detected by monoclonal antibodies raised against the cell wall Gal-NAG polysaccharide of the pathogen (22). The exoand/or cell wall Gal-NAG polysaccharide, which is present in the culture medium for growing *B. anthracis* (4), can be isolated from the cell wall of the microbe (22,42). Given that the Gal-NAG polysaccharide is universally present among and specific for strains of *Bacillus anthracis* (22), its presence in solution and its structural stability, makes this molecule a potential target for the identification of *B. anthracis* and for developing an anthrax vaccine.

Early studies were conducted by the late Professors Michael Heidelberger (see ref. 43 page 451 for a description) and Elvin A. Kabat (44-46) to investigate the antigenic cross-reactivities among blood group substances (ABO), Pneumococcus type 14-polysaccharide and the cell wall polysaccharide of *B. anthracis*. A preparation of the anthrax polysaccharide is available in the KABAT collection at Columbia University. The anthrax polysaccharide was tested on a carbohydrate microarray and confirmed that the preparation has preserved its cross-reactivity to an anti-Pneumococcus type 14-polysaccharide antibody (data not shown).

Following are some important characteristics of the cell wall Gal-NAG polysaccharide: (a) it is 12,000 Da in molecular weight and contains galactose, N-acetylglucosamine, and N-acetylmannosamine in an approximate molar ratio of 3:2:1 (22) or 10:2:1. This slight difference in molar ratio is attributed to differences in the hydrolysis conditions applied (47); (b) it is pyruvylated although the sugar residue and position of pyruvylation are yet to be determined (47); (c) it is most likely *B. anthracis* specific and expressed by both germinating spores and the vegetative *bacillus* (22); (d) it shows antigenic determinants which are cross-reactive to Pneumococcus type 14 polysaccharide (43); (e) it has no human blood group substances A, B, or H activity (43); and (f) anti-serum elicited by the anthrax polysaccharide has, however, cross-reactivities with a preparation of hydrolyzed blood group substance A that contains the type II Gal-GlcNAc sequences (Gal β1→4GlcNAc) (see ref. 43, page 452 for a description of the study by Ivanovicx (1940)).

These characteristics lead to the conclusion that: (i) The Gal-NAG polysaccharide expresses potent antigenic determinants to mice and humans since the pyruvylated Gal-NAG structure is not present in the host; (ii) the polysaccharide itself is, however, poorly antigenic in solution since it is a T-independent antigen with relatively low molecular weight (1.2 KDa). Given this consideration, early observations that the polysaccharide was not protective to animals challenged by *B. anthracis* can be attributed to the nature of poor immunogenicity in its native configuration; (iii) its Gal-NAG core structure is similar to a core structure of blood group type II chain, Gal β1→4GlcNAc. Pyruvylation of the backbone structure blocks, however, its blood group substance H reactivity; and (iv) given that the pyruvate group is not seen in Pneumococcus type 14 polysaccharide, the anthrax polysaccharide may contain a non-pyruvylated antigenic determinant mimicking those of the Pneumococcus type 14 polysaccharide. This leads us to conclude, therefore, that the cell wall polysaccharide of *B. anthracis* contains more than one antigenic determinant.

A carbohydrate microarray was designed to maximize the surface display of its potential antigenic structures using the following method: (a) print the polysaccharide on a microchip to display its antigenic determinants in the native configuration; (b) isolate the pyruvylated and non-pyruvylated fractions of the polysaccharide and apply them on the microarray as described by Mesnage et al. (47). This allows investigation of the potential dominant role of the pyruvylated sugar structure in its antigenicity; and (c) synthesize a panel of oligosaccharide-protein conjugates.

In the chip design, we have also included structures of oligosaccharides that are identical to or derived from those of Pneumococcus type 14 polysaccharide and those reactive to lectin *Glycine max* (specific for alpha-D-galactose or 2-acetamido-2-deoxy-alpha-D-galactose residues) that recognize a proposed spore glycoprotein of *Bacillus anthracis* (41).

V. Methods to Search and Identify Pairs of Antigens and Antibodies for Antigen/Antibody Microarrays Detecting microbial antigens in serum or other body fluids is useful in the diagnosis of an infectious disease but generally it is difficult. It is, therefore, necessary to establish a highly sensitive antibody-based microarray to detect microbial antigens. In addition, such an antibody-based microarray will allow us to monitor a microbial pathogen in the environment as well as in host body fluids. Identification of highly specific antigens and antibodies for each pathogen is critical for the development of a diagnostic biochip.

Figure 14:
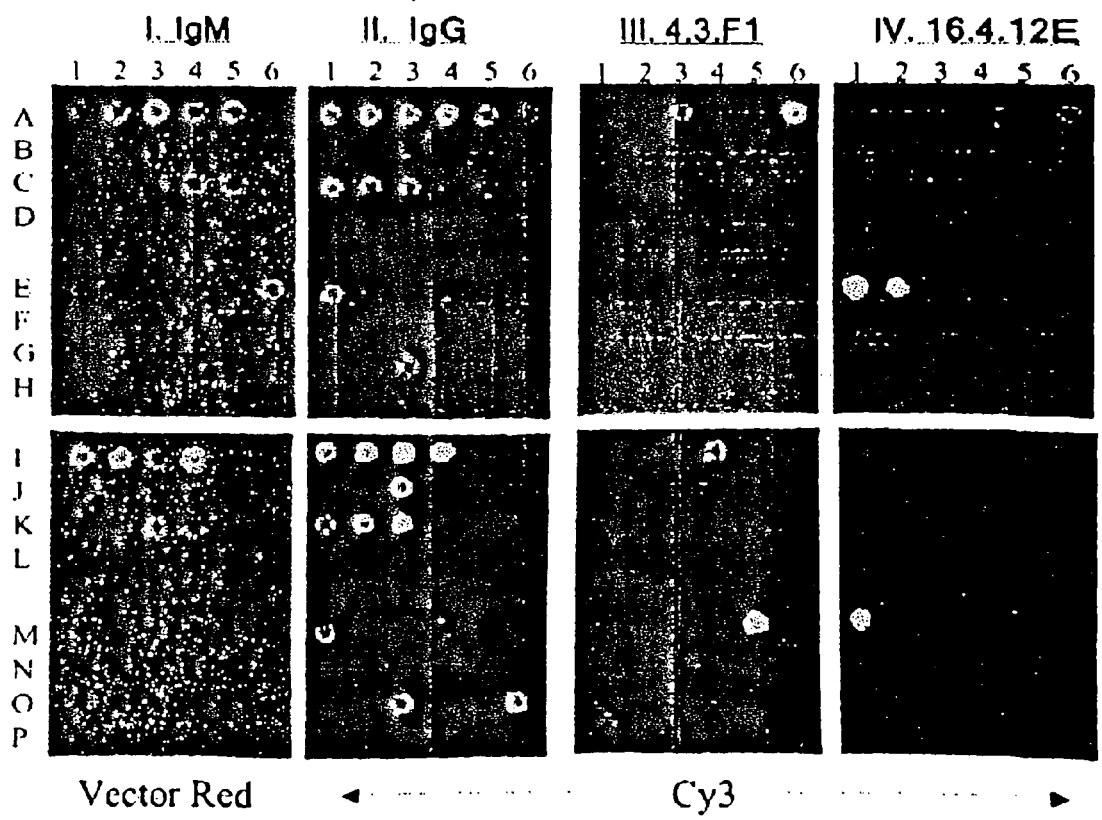

We have established a simple and effective strategy to screen for these reagents for microarray production. We printed a panel of forty-eight carbohydrate-containing macromolecules of distinct structural characteristics on a slide with the method established above. In previous investigations, these antigens were successfully applied to screen human myeloma and lymphoma proteins for antibodies with anti-carbohydrate activities (48, 52, 53). The carbohydrate microarray was applied to detect human serum antibodies. A total number of twenty serum specimens were randomly collected from normal individuals. As little as one micro-liter of serum specimen from each individual was applied for microarray staining. As shown in FIG. 14, twelve distinct specificities of IgM antibodies (12/48) and thirty-five IgG anti-carbohydrate antibodies (35/48) were identified. Carbohydrate molecules that were positively stained include twenty polysaccharides (20/24), eleven complex carbohydrates of cellular origin (11/19) and four semi-synthetic glycoconjugates (4/5). For anti-carbohydrate antibodies of IgM isotype, twelve distinct specificities were identified. The majority (7/12) were bound to *Klebsiella* polysaccharides. This is similar to our previous observation that antibodies bound to *Klebsiella* polysaccharides were most frequently found in the repertoire of human myeloma anti-carbohydrate antibodies (48-52). The repertoire of human IgG anti-carbohydrate antibodies is, however, broader than those of IgM isotype. There are twenty specific for microbial polysaccharides (20/24), including polysaccharides of microbial pathogens, *E. coli*-K92 and -K100; Pneumococcus type-C, -VIII, -IX, -SIV, -XIV and -27; Group B Meningococcus, *H. Influenza* Type A, and different types of *Klebsiella*. Human IgG antibodies specific for glycomers of complex carbohydrate structures (11/19) and those for the carbohydrate moieties of semi-synthetic glycoconjugates (4/5) were also detected.

This antigen microarray was then applied to characterize monoclonal antibodies (FIG. 14, panels III and IV) to critically evaluate their antigenic or epitope-binding specificities and cross-reactivities. Antigenic cross-reactivity between microbial polysaccharide α(1,6)dextran and a preparation of Chondroitin sulfate B polysaccharide that was derived from the intestinal mucosa of porcine was demonstrated. This has led to the recognition of a novel cross-reactive molecular marker of microbes and host cell (11). In addition, these experiments demonstrated that semi-synthetic glycoproteins are applicable for the construction of a carbohydrate microarray. This is of critical importance since it enables the application of rationally designed synthetic oligosaccharides for microarray construction and allows a critical examination of the specificity and cross-reactivity of carbohydrate-mediated molecular recognition.

The flexible 8-chamber biochip system, as described above, is sufficient for this type of initial screening of a panel of molecular targets. In this format, all the available antigen preparations of the eight Category-A pathogens can be printed at various dilutions in a single sub-array chamber. A specific antibody, for example, a mouse monoclonal antibody bound to the anthrax polysaccharide, can be applied on the sub-array biochip to react with all the antigens on the chip. It may also be applied in a series of dilutions on different sub-array chambers. This simple experiment allows us to critically evaluate (a) antibody binding specificity and cross-reactivity; (b) the affinity of antigen-antibody interaction; and (c) the quality of the printed antigen and method for immobilizing the antigen.

If an antigen/antibody pair is qualified by the 8-chamber biochip analysis, a further evaluation is conducted using a large-scale biochip, which displays both microbial antigens and those from human and other mammalian species. The highly specific pairs of antigens and antibodies are candidates for the diagnosis of corresponding microbial infections. Those who have cross-reactivities with human tissue antigens may be also useful for printing microarrays. As summarized above, identification of such cross-reactivities may lead to a better understanding of the biological relationship of microbes and their hosts, as well as the pathogenesis mechanisms of an infectious disease.

VI. Methods to Search and Identify Novel Protein Targets for Diagnosis and Vaccination As described above, we have already established that our microarray platform is useful for printing protein microarrays and have demonstrated the principle and method to apply a large panel of protein antigens to extend our scope of investigation of microbial infections. This investigation has provided insights into how one could incorporate the genomic information and genetic material that has been accumulated by the genome sequencing projects into the development of diagnostic protein biochips. We report here the establishment of a strategy to efficiently utilize the information from the various pathogen genome projects to assist in the identification of novel molecular targets for diagnosis and vaccination. The pX01 plasmid of *B. anthracis* will serve as a model to illustrate our strategy.

(A) Methods to Search and Identify Candidates for the Protein Microarray

Different categories of proteins can be used to produce the diagnostic protein microarray. For example, (a) both membrane-bound and secretory proteins of a pathogen, which may trigger the initial immune response in an infection, making them ideal targets for early diagnosis and vaccination; (b) non-surface expressed proteins, which could be useful in identifying and characterizing the progressive stages of an infection; and (c) the candidate genes that are unique to a given pathogen, namely the species-specific or stain-specific molecular targets, thereby enabling highly specific detection on the final biochip.

Two categories of bioinformatic software, predicative and comparative, are currently available on-line. A two-step analysis can be used to identify candidate gene products to be included on the microarray. First, the structure, cellular location, and function of newly discovered genes of the genome sequencing projects is predicted. Then a comparative analysis to predict the specificity and potential cross-reactivity of the candidate genes selected by the above structure-function predictive analysis is performed. A list of "predictive" software tools that will help in extrapolating a protein's function are available on-line. These include (a) TMHMM (www.cbs.d-tu.dk/services/TMHMM-2.0) for the prediction of transmembrane helices in proteins; (b) NetOGlyc 2.0 (www.cbs.dtu.dk/services/NetOGlyc) for prediction of mucin type GalNAc O-glycosylation sites in mammalian proteins; (c) PredictProtein (www.embl-heidelberg.de/predictprotein/predictprotein.html); for the prediction of secondary structure, solvent accessibility, and transmembrane segments; and (d) 3D-PSSM Web Server V 2.6.0 (www.bmm.icnet.uk/~3dpssm/) for protein fold recognition.

With the predicted location and structure of the protein now known, either through published gene annotation done upon completion of a genome sequence, or through predictive bioinformatic software, it is equally important to determine whether the gene of interest is unique to the species through a comparative proteomic analysis. This is crucial if we hope to design a biochip that can specifically identify if the patient is suffering from *B. anthracis*. A gene that is similar in both *B. anthracis* and *B. subtilis* would be a poor choice for the biochip, because it would lead to inconclusive results when deployed in the field. Therefore, careful study should be done in order to identify if genes are highly unique to the species, which would in turn result in a biochip with few cross-reactive ambiguous results. One example of a potentially valuable bioinformatic tool to address this problem is called the COGnitor program. This program takes an amino acid sequence and extrapolates its function by comparing the unknown protein's sequence of amino acids to amino acid sequences from other genes of characterized function in a series of genomes (54). Genes that are highly conserved in evolution would be identifiable using the COGnitor program; those that are unique to a given organism could be non-recognizable by a COGnitor search. Proteins that are not recognized by the COGnitor program are probably high priority candidates for diagnostic application since the proteins they encode are most likely species-specific antigens. For the genes that are recognized and classified by the program, additional steps of investigation must be taken to define whether they are suitable targets for a diagnostic use.

(B) A Model to Illustrate Our Comparative Genomic Strategy to Identify Unique Genes The pX01 plasmid of *Bacillus anthracis* has been fully sequenced, and 46 of the 142 identified genes have been functionally characterized in the literature (16). This provides us with a prime example of how a complete DNA sequence, with some gene annotation, would be approached using our comprehensive bioinformatic strategy.

Figure 15:
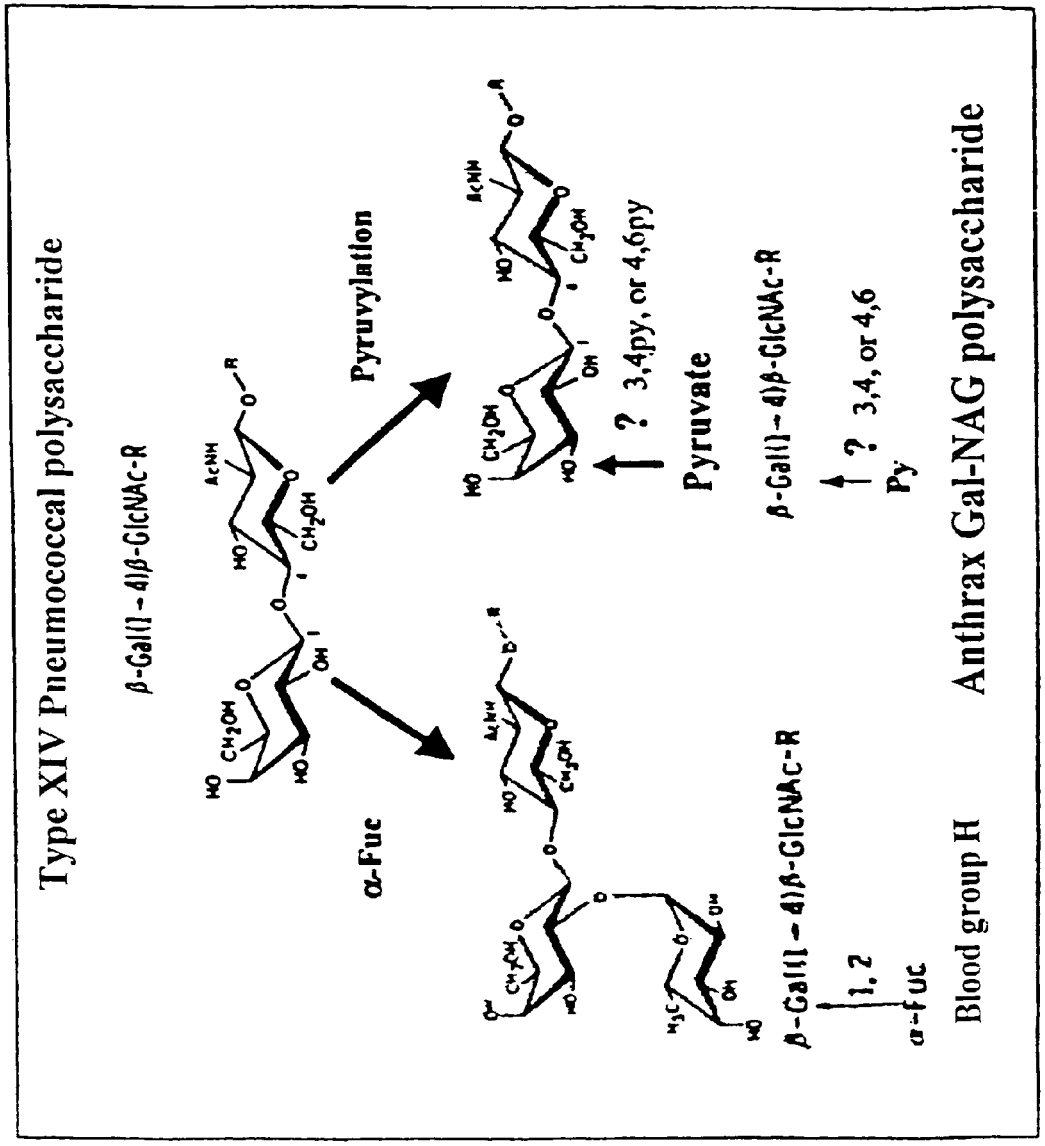
Figure 16:
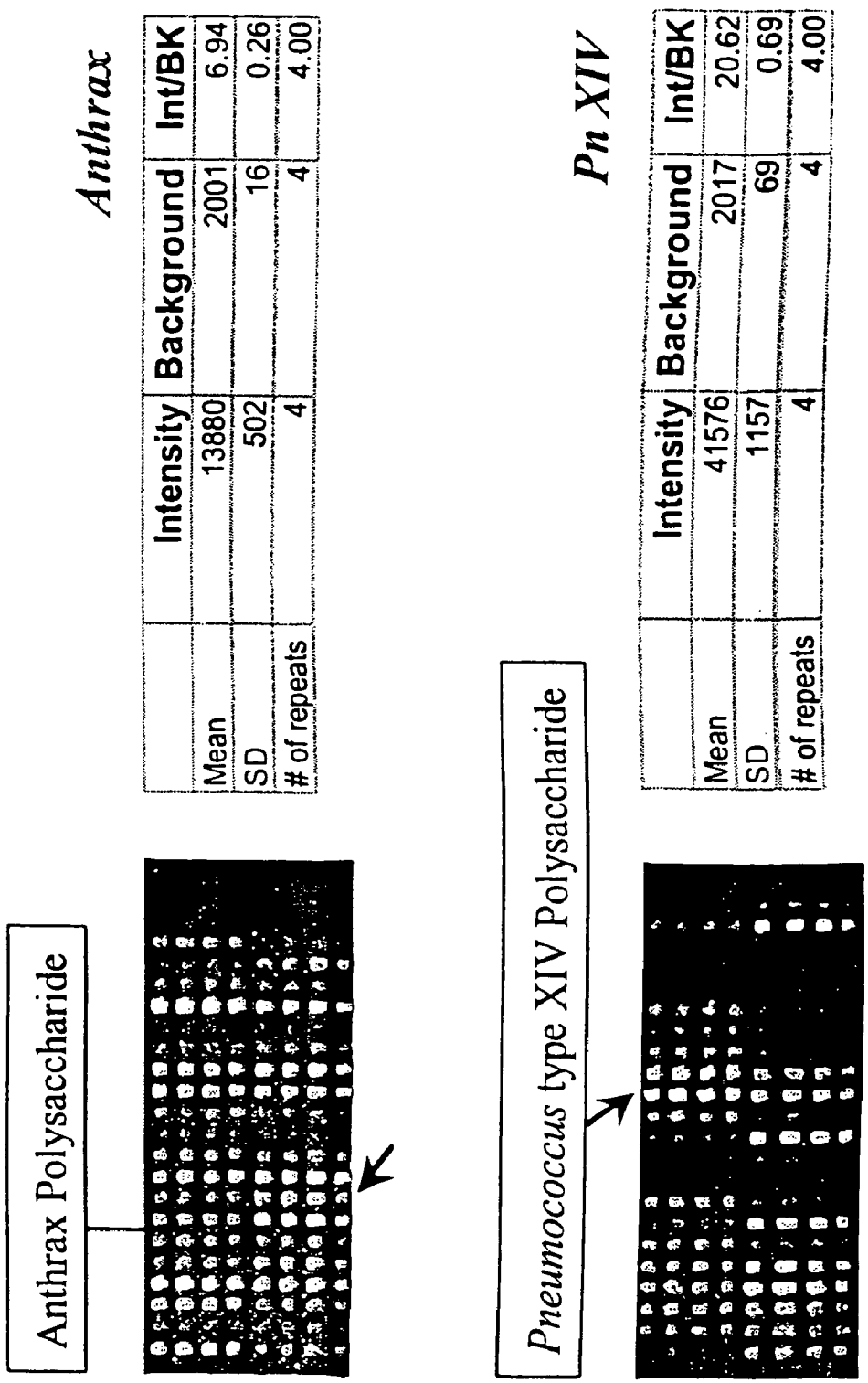

First, we use predictive bioinformatic software to determine the location and structural characteristics of the proteins from their amino acid sequences. One example of this is in predicting if a protein has transmembrane regions, as can be determined by TMHMM version 2.0 (55). We have selected the protein Px01-54 as an example. Okinaka et al. have given a description of this protein as a "S-layer precursor/surface layer protein." This protein was run through the transmembrane predicting software TMHMM version 2.0 (see FIG. 15).

It would seem that this protein contains both a transmembrane region, as well as a large extracellular component. One could hypothesize that, based on this result, the protein is on the surface of the bacteria, and is an ideal candidate to be printed on a microarray because it may play a role in initiating a primary immune response. Therefore, even if Okinaka et al did not characterize the gene, we could use this software to identify it as an ideal surface target that could induce a primary immune response.

With the completion of the predictive stage for function and location of a protein, the next stage of bioinformatic analysis is conducted, namely to determine if the gene of interest is unique to an organism. As described above, the COGnitor program (54) can be used to identify the species-specific genes/proteins for printing the diagnostic protein chips. To test this idea, we have run the amino acid sequences of all the 46 annotated genes of Px01 plasmid of *B. anthracis* through the COGnitor program. We present the results from this test in Table 2.

Of the 46 genes analyzed, 34 could be recognized and classified according to the COGnitor program. A large number of the COG-classified genes are of category L, namely DNA replication, recombination and repair. Indeed, it is likely that such proteins contain highly conserved domains across many species. At the other extreme, twelve genes were not recognized by the COGnitor program, and were thereby not able to be classified into the COG classifications. These unclassifiable proteins have been listed as "No Cog" in Table 2. This "No Cog" classification indicates that these proteins have no similarity to other proteins currently in the database. Since the COG database includes 74,059 classified protein sequences from the genomes of 43 species of both prokaryotic and eukaryotic organisms (but excludes the human genome), a "No Cog" result suggests that the protein in question is more likely to be species or strain-specific to the pathogen. At the very least, one can claim that it is highly unlikely for a "No Cog" protein to contain a known evolutionarily conserved ancient domain that exists across many species' genomes. Being able to select against genes that exhibit such conserved domains is a welcome tool, for this could help to lower the probability of selecting a protein that may yield ambiguous results on the final biochip due to cross reactivity. Interestingly, the genes of the most unique lethal nature, as well as a series of surface antigens, are not recognized by the COGnitor program because they match no other species' genes. One example of an ideal gene to select has been presented, namely the px01-54 protein of *B. anthracis*. This protein is expressed on the surface of the organism according to Okinaka et al. (16), spans a membrane according to the TMHMM program, and is not recognized by the COGnitor program, making it more likely to be unique to the species.

In conclusion, combining knowledge from the published literature and bioinformatic software on a gene product's function, location, and 'species unique' level will greatly enhance the use of the final biochip because it will allow clear and accurate clinical diagnosis of a patient's immune response to a wide panel of pathogenic agents.

REFERENCES

1. Blaustein, R. O., Koehler, T. M., Collier, R. J. & Finkelstein, A. Anthrax toxin: channel-forming activity of protective antigen in planar phospholipid bilayers. Proc Natl Acad Sci USA 86, 2209-2213. (1989).
2. Thorne, C. B. *Bacillus anthracis*. In *Bacillus subtilis* and Other Gram-positive Bacteria, ed. AL Sonenshein, J A Hoch, R Losick., 113-124 (1993).
3. Escuyer, V. & Collier, R. J. Anthrax protective antigen interacts with a specific receptor on the surface of CHO-K1 cells. Infect Immun 59, 3381-3386. (1991).
4. Strange, R. E. & Belton, F. C. Studies on a protective antigen produced in vitro from *bacillus anthracis*: Purification and chemistry of the antigen. Bri. J. Exp. Pathol. 35, 153-165 (1953).
5. Mourez, M. et al. Designing a polyvalent inhibitor of anthrax toxin. Nat Biotechnol 19, 958-961. (2001).
6. Brown, P. O. & Botstein, D. Exploring the new world of the genome with DNA microarrays. Nature. Genetics. 21, 33-37 (1999).
7. DeRisi, J. L., Iyer, V. R. & Brown, P. O. Exploring the metabolic and genetic control of gene expression on a genomic scale. Science. 278, 680-686 (1997).
8. Ramsay, G. DNA chips: state-of-the art. Nature. Biotechnology. 16, 40-44 (1998).
9. MacBeath, G. & Schreiber, S. L. Printing proteins as microarrays for high-throughput function determination. Science 299, 1760-1763 (2000).
10. Lueking, A. et al. Protein microarrays for gene expression and antibody screening. Analytical. Biochemistry. 270, 103-111 (1999).
11. Wang, D., Liu, S., Trummer, B. J., Deng, C. & Wang, A. Carbohydrate microarray leading to the recognition of cross-reactive molecular markers of microbes and host cells. Nature Biotechnology 20 (2002).
12. Ekins, R. P. Multi-analyte immunoassay. J Pharm Biomed Anal 7, 155-168 (1989).
13. Stoll, D. et-al. Protein microarray technology. Front Biosci 7, C13-32. (2002).
14. Volchkov, V. E. Ebola virus, complete genome. Institute of Virology, Philipps-University (2000).
15. Shchelkunov, S. N., Totmenin, A. V. and Sandakhchiev, L. S. Analysis of the nucleotide sequence of 23.8 kbp from the left terminus of the genome of variola major virus strain India-1967. Virus Res. 40, 169-183 (1996).
16. Okinaka, R. T. et al. Sequence and organization of pXO1, the large *Bacillus anthracis* plasmid harboring the anthrax toxin genes. J Bacteriol 181, 6509-6515. (1999).
17. Wang, D. & Kabat, E. A. in Structure of Antigens., Vol. Three. (ed. M. H. V. V. Regenmortal) 247-276 (CRC Press, Boca Raton New York London Tokyo; 1996).
13. Wyatt, R. et al. The antigenic structure of the HIVgp120 envelope glycoprotein. Nature 393, 705-711 (1998).
19. Robbins, J. B. & Schneerson, R. Polysaccharide-protein conjugates: a new generation of vaccines. J. Infct. Dis. 161, 821-832 (1990).
20. Schneerson, R., Barrera, O., Sutton, A. & Robbins, J. B. Preparation, characterization, and immunogenicity of *Haemophilus influenzae* type b polysaccharide-protein conjugates. J Exp Med 152, 361-376. (1980).
21. Gladstone, G. P. & Walton, E. Effect of iron on the bactericidal proteins from rabbit polymorphonuclear leukocytes. Nature 227, 849-851. (1970).
22. Ezzell, J. W., Jr., Abshire, T. G., Little, S.F., Lidgerding, B. C. & Brown, C. Identification of *Bacillus anthracis* by using monoclonal antibody to cell wall galactose-N-acetylglucosamine polysaccharide. J Clin Microbiol 28, 223-231. (1990).
23. Finne, J., Leinonen, M. & Makela, P. H. Antigenic similarities between brain components and bacteria causing meningitis. Implications for vaccine development and pathogenesis. Lancet. 2, 355-357 (1983).
24. Finne, J. & Makela, P. H. Cleavage of the polysialosyl units of brain glycoproteins by a bacteriophage endosialidase. Involvement' of a long oligosaccharide segment in molecular interactions of polysialic acid. Journal. of. Biological. Chemistry. 260, 1265-1270 (1985).
25. Mandrell, R. E. et al. Lipooligosaccharides (LOS) of some *Haemophilus* species mimic human glycosphingolipids, and some LOS are sialylated. Infection. &. Immunity. 60, 1322-1328 (1992).
26. Mandrell, R. E. Further antigenic similarities of *Neisseria gonorrhoeae* lipooligosaccharides and human glycosphingolipids. Infection. &. Immunity. 60, 3017-3020 (1992).

27. Feizi, T. & Loveless, R. W. Carbohydrate recognition by *Mycoplasma pneumoniae* and pathologic consequences. Am. J. Respir. Crit. Care. Med. 154, S133-136. (1996).
28. Burrel, C. J. Serological markers of hepatitis B. Clin Gastroenterol 9, 47-63. (1980).
29. Boxall, E. H., Peterson, S., Diment, J., Graham, S. E. & Shirley, J. A. A novel assay for hepatitis B e markers. J Med Virol 52, 280-285. (1997).
30. Basten, A. & Howard, J. G. in Contemporary Topics in Immunobiology, Vol. 2. (ed. A. J. S. Davies) 265 (Plenum, New York; 1973).
31. Humphrey, J. H., Parrott, D. M. V. & East, J. Studies on globulin and antibody production in mice thymectomised at birth. Immunology 7, 419-439 (1964).
32. Weissman, I. L., Gutman, G. A., Friedberg, S. H. & Jerabek, L. Lymphoid tissue architecture. III. Germinal centers, T cells, and thymus-dependent vs thymus-independent antigens. Adv. Exp. Med. Biol. 66, 229-237 (1976).
33. Beagley, K. W., Black, C. A., Dunkley, M. L. & McGhee, J. R. in Cytokine Regulation of Humoral Immunity. (ed. C. M. Snapper) 391-408 (John Wiley & Sons Ltd, Chichester, N.Y., Brisbane, Toronto, Singapore; 1996).
34. McGhee, J. R., Mestecky, J., Elson, C. O. & Kiyono, H. Regulation of IgA synthesis and immune response by T cells and interleukins. [Review]. Journal of Clinical Immunology 9, 175-199 (1989).
35. Mestecky, J. The common mucosal immune system and current strategies for induction of immune responses in external secretions. [Review]. Journal of Clinical Immunology 7, 265-276 (1987).
36. Mongini, P. K. A., Stein, K. E. & Paul, W. E. T-cell regulation of IgG subclass antibody production in response to T-independent antigens. J. Exp. Med. 153, 1-12 (1981).
37. Kagnoff, M.F. & Murray, P. D. T dependent induction of an IgA and IgM anti-polysaccharide response. Advances in Experimental Medicine & Biology, 155-167 (1987).
38. Ivars, F., Nyberg, G., Holmberg, D. & Coutinho, A. Immune response to bacterial dextrans. II. T cell control of antibody isotypes. Journal of Experimental Medicine 158, 1498-1510 (1983).
39. Ehrhardt, R. O. et al. Differential activation requirements of isotype-switched B cells. Eur. J. Immunol. 26, 1926-1934 (1996).
40. Tonkinson, J. L. & Stillman, B. A. Nitrocellulose: a tried and true polymer finds utility as a post-genomic substrate. Front Biosci 7, C1-C12. (2002).
41. Cole, H. B., Ezzell, J. W., Jr., Keller, K.F. & Doyle, R. J. Differentiation of *Bacillus anthracis* and other *Bacillus* species by lectins. J Clin Microbiol 19, 48-53. (1984).
42. Cohen, S. et al. Attenuated nontoxinogenic and nonencapsulated recombinant *Bacillus anthracis* spore vaccines protect against anthrax. Infect Immun 68, 4549-4558. (2000).
43. Smith, H. & Zwartouw, H. T. The polysaccharide from *Bacillus anthracis* grown in vivo. Biochem J 63, 447-452 (1956).
44. Kabat, E. A., Bezer, A. E., Baer, H. & Knaub, V. Immunochemical studies on blood groups. VII. Chemical changes associated with destruction of blood group activity and enhancement of the type XIV cross-reactivity by partial hydrolysis of hog and human blood group A, B, and O, substances. J. Exp. Med. 88, 43-57 (1948).
45. Kabat, E. A., Howe, C. & Schiffman, Immunnochemical studies on blood groups. J. Am. Chem. Soc. 80, 6656 (1958).
46. Kabat, E. A. Immunochemical studies on blood groups. J. Immunol. 82, 358-372 (1958).
47. Mesnage, S. et al. Bacterial SLH domain proteins are non-covalently anchored to the cell surface via a conserved mechanism involving wall polysaccharide pyruvylation. Embo J 19, 4473-4484. (2000).
48. Kabat, E. A. et al. Human monoclonal macroglobulins with specificity for *Klebsiella* K polysaccharides that contain 3,4-pyruvylated-D-galactose and 4,6-pyruvylated-D-galactose. J. Exp. Med. 152, 979-995 (1980).
49. Kabat, E. A. et al. The epitope associated with the binding of the capsular polysaccharide of the group B meningococcus and of *Escherichia coli* K1 to a human monoclonal macroglobulin, IgM NOV. J. Exp. Med. 168, 699-711 (1988).
50. Kabat, E. A., Liao, J., Sherman, W. H. & Osserman, E.F. Immunochemical characterization of the specificities of two human monoclonal IgM's reacting with chondroitin sulfates. Carbohydr. Res. 130, 289-297 (1984).
51. Kabat, E. A., Liao, J., Shyong, J. & Osserman, E.F. A monoclonal IgM lambda macroglobulin with specificity for lacto-N-tetraose in a patient with bronchogenic carcinoma. J. Immunol. 128, 540-544 (1982).
52. Kabat, E. A. et al. A human monoclonal macroglobulin with specificity for a (2----8)-linked poly-N-acetyl neuraminic acid, the capsular polysaccharide of group B meningococci and *Escherichia coli* K1, which crossreacts with polynucleotides and with denatured DNA. J. Exp. Med. 164, 642-654 (1986).
53. Nickerson, K. G., Liao, J. & Kabat, E. A. A monoclonal IgM kappa from a blood group B individual with specificity for alpha-galactosyl epitopes on partially hydrolyzed blood group B substance. Carbohydr. Res. 243, 345-357 (1993).
54. Tatusov, R. L., Koonin, E. V. & Lipman, D. J. A genomic perspective on protein families. Science 278, 631-637. (1997).
55. Krogh, A., Larson, B., von Heijne, G. & Sonnhammer, E. L. Predicting transmembrane protein topology with a hidden Markov model: application to complete genomes. J Mol Biol 305, 567-580. (2001).

Fourth Series of Experiments

HydroGel™ slides are produced by Packard BioScience for printing protein microarrays. We investigated whether Hydrogel can serve as an alternative substrate for producing carbohydrate microarrays and for producing HIV diagnostic protein microarrays.

I. Materials And Methods

A. Procedures for Printing and Staining of the Hydrogel-Based Biochips (1) Method for Printing on Hydrogel-Coated Slides The method for printing carbohydrates and proteins on Hydrogel-coated slides is essentially identical to that for printing on nitrocellulose slides. The only difference is that the pre-treatment of Hydrogel follows the method described by the manufacture as follows: (a) place HydroGel slides in 40° C. incubator for 20 minutes; and (b) remove prior to printing and allow slides to cool to room temperature for 5 minutes.

2) Method for Post-Printing Treatment

The procedures for post-printing treatment were modified from the manufacture's instruction as follows: (a) incubate arrays overnight in a humidified 30° C. chamber; (b) rinse briefly (for 20 seconds) in PBST (PBS+0.05% Tween 20), followed by 3, 30 minute washes with PBST. Rinse for 20 seconds in PBS (pH 7.4); and (c) dry slides by centrifugation at 1600 RPM for 5 minutes in a table-top centrifuge.

(3) Method for Staining The methods for staining Hydrogel biochips are identical to those for staining nitrocellulose biochips.

II. Results and Discussion

Applicants have shown the following surprising results:
1) Printing proteins and carbohydrate-containing macromolecules on hydrogel can be performed using Cartesian's PIXSYS 5500A Microarryer (CHIPMAKER 4), using a contact arraying procedure.
2) Protein preparations, including antibodies, BSA, Avidin and HIV-1 gp120, RT and gag proteins, can be quantitatively immobilized on the hydrogel, providing fine spots of about 150 microns in diameter and thus making it possible to produce a high density protein microarray.
3) Carbohydrate preparations, including polysaccharides, glycosaminoglycans, glycoproteins, semi-synthetic glycoconjugates and glycolipids, can be quantitatively immobilized on the hydrogel, providing fine spots of about 200 microns in diameter and thus making it possible to produce a high density carbohydrate microarray.
4) The immobilized protein and carbohydrate antigens analyzed have their immunological properties well-preserved at the time the slides were stained using specific antibodies.
5) Use of the Hydrogel-based protein and carbohydrate microarrays is advantageous due to their low fluorescent background. A disadvantage of the Hydrogel substrate is its absorption of relative lower amounts of materials on the biochip. For the same antigen preparations, the fluorescent signals detected on Hydrogel-slides are much lower than those detected on the nitrocellulose slides.
6) When the ratios of fluorescent intensity over background of given microspots are calculated, the results of nitrocellulose-chips and those of Hydrogel-chips are closely correlated in most cases (see Table 4 for a comparison among antigens of distinct structural characteristics).
7) The nitrocellulose-based biochip favors detection of IgG antibodies but not IgM antibodies in solution. The former is an immunoglobulin (Ig) monomer; and the latter is an Ig pentamer. Such bias is not seen in the Hydrogel-based biochips. This finding is of significance since it provides information to improve the nitrocellulose surface for producing a diagnostic biochip.

Fifth Series of Experiments

I. Introduction

An infectious agent may expose and release multiple antigenic substances to a host, eliciting specific antibody responses. Many antigen-antibody binding assays are currently in use for clinical diagnosis of infectious and non-infectious diseases. These include the classical direct immunoassays, such as, immunodiffusion, immunoelectrophoresis, agglutination and immunoprecipitation, and recently developed methods, including immunofluorescence, radioimmunoassay (RIA), enzyme-immunoassay (EIA) and western blot. These approaches take advantage of the specificity of antigen-antibody interaction but are designed to operate on a one-by-one basis. Their successful diagnostic application for infectious diseases is, therefore, largely dependent on whether a clinician makes the correct decision regarding which diagnostic test should be run.

Establishment of technologies to enable the simultaneous detection and characterization of a wide range of microbial infections represents a current challenge to the worldwide effort of biodefense. High-priority infectious agents that pose current risks to our national security include multiple microbial pathogens, such as *Bacillus anthracis* (anthrax), *Clostridium botulinum* (botulism), *Yersinia pestis* (plague), Variola virus (smallpox), *Francisella tularensis* (tularemia) and viral hemorrhagic fevers (Lassa virus, Ebola virus, Marburg virus and LCM virus). An assay system that allows detection and characterization of these pathogens in a single assay is currently unavailable.

Rapid progress of the genome sequencing projects has brought new hopes as well as challenges to biodefense efforts. For example, a great deal of genomic information is available for numerous pathogens[1,2,3]. This leads the way to developing a generation of high throughput technologies to combat emerging infectious diseases. These include the nucleic acid-based microarrays[4,5] or DNA chips[6], and the protein-based microarrays[7,8]. Application of these technologies in the field of infectious diseases is still in its early stages[9,10]. Novel ideas are badly needed for the establishment of high throughput technologies to monitor potential bioterrorism attacks as well as naturally occurring emerging infectious diseases.

Our laboratory has been focusing on the development of a biochip platform that is suitable for the production of both carbohydrate and protein-based microarrays. Our carbohydrate microarray technology is described herein. Such a technology is designed to display a large repertoire of pathogen-specific antigens of distinct structures in order to monitor a broad range of microbial infections. Since it is applicable for human and many other animal species, this system is particularly useful for monitoring the emergence of infectious diseases. In many infectious diseases, an intermediate reservoir plays important roles in the life cycle of the pathogen. In other cases, both human and animal species are accessible to a given pathogen.

A number of category A pathogens (*Bacillus anthracis, Clostridium botulinum, Yersinia pestis*, and viral hemorrhagic fevers) and other emerging infectious diseases (Lyme disease and West Nile Virus infection) have such characteristics. Thus, the antigen/antibody-based biochips will play a significant role in the surveillance of emerging infectious diseases (FIG. 17).

Both carbohydrate antigens and protein antigens are important for the production of a diagnostic biochip. As shown in FIG. 17, the presence of a polysaccharide in *Bacillus anthracis* has been recognized for some time[11,12,13]. It is specific for *B. anthracis*, a useful molecular target for the identification of the pathogen. This structure is, however, masked before spore germination, casting doubt on its potential for vaccination use. A protein antigen of *B. anthracis*, the protective antigen (PA) is a well-recognized vaccine target. PA is an integrated component of the lethal toxin of *Bacillus anthracis*. It binds to a specific cellular receptor and forms cell bound complexes with edema factor (EF) and lethal factor (LF)[14-16]. Understanding of this process led to the development of polyvalent inhibitor-based therapeutic strategies to protect a host from lethal attack by the toxin[17].

Given our current knowledge of protein chemistry, on-chip protein structural alterations, including denaturation or partial denaturation and various degrees of conformational modification, are unavoidable in the course of a long time period in storage (months to years). However, the such alterations are acceptable when a protein chip is made for an immunological application because a naturally occurring infection or vaccination elicits specific antibodies directed to both the native and the denatured/partially denatured antigenic determinants.

In summary, detecting a microbial antigen and/or its specific antibodies in bodily fluids are important in diagnosis of infectious diseases and in surveillance of emerging infectious diseases. This goal is achieved by an antigen/antibody-based microarray of high sensitivity, large capacity, and extensive antigenic diversity.

II. Procedures for Production of Long-Lasting Protein Microarrays This section is directed to a central technical difficulty in the technology of proteomic microarrays—the structural and conformational instability of protein on-chip. Our procedures include a) a high throughput technology to screen for the antigen preparations that are applicable for our proposed microarray platform; b) the technology for the production and long-lasting preservation of protein microarrays; and c) Green Chip Technology to facilitate protein chip development.

(A) High Throughput Screening to Identify Stable Antigens for the Production Protein Chips In our preliminary investigation, we found that the on-chip stability of protein antigens varies among molecules and/or preparations. Molecular mechanisms underlying these differences are quite complex. To meet the urgent need of biodefense, we take a straightforward but efficient approach to facilitate the development of diagnostic biochips. Specifically, we have established a microarray-based high throughput screening technology to identify suitable microbial antigens for biochip production.

Our method of protein chip fabrication is a non-covalent protein immobilization on a nitrocellulose-coated micro-glass slide. It uses a nitrocellulose-surface to immobilize an antigen, similar to the Western Blot assay, but has no treatment to denature the protein before its application. A protein microspot is, therefore, printed on the chip without any chemical or physical treatment to interfere with its native structure.

We have designed a single step assay in which protein antigens are printed on the nitrocellulose-coated slides and then stained by antibodies to "see" whether specific antigenic determinants are displayed on chip and whether they are accessible to antibodies in solution. The monoclonal and polyclonal antibodies elicited by a microbial antigen or by a pathogen, as well as serum specimens of an infected individual, are all useful reagents for these analyses. A positively stained microspot indicates the presence of a target molecule or antigenic determinant.

Figure 10:
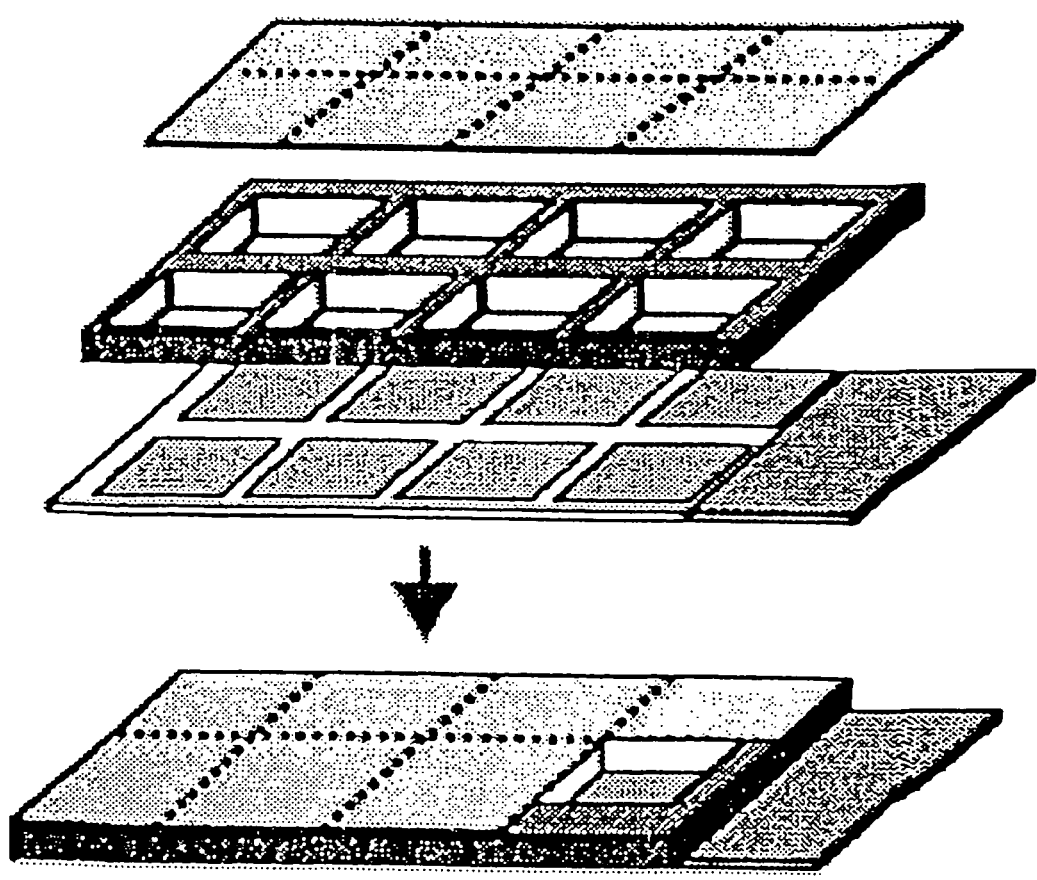

We have established two methods, a) an eight-chamber sub-array system (FIG. 10) and b) a full-scale biochip scanning (FIG. 11), to facilitate the screening process.

1. An Eight-Chamber Sub-Array System

Each microglass slide contains eight well-separated sub-arrays of identical contents. Its microarray capacity is 600 microspots per subarray. A single slide is, therefore, designed to enable eight microarray analyses. Antibodies can be applied on separate subarrays in a serial dilution as in an ELISA assay.

a) 8-Chamber Sub-Arrays (See FIG. 10):

Each microglass slide contains eight-well separated sub-arrays of identical contents. There are 600 microspots per subarray, with spot sizes of approximately 200 microns and at 300-micron intervals, center-to-center. A single slide is, therefore, designed to enable eight detections.

b) Contains:

i) A 600-spot subarray is composed of pathogen-specific protein antigens in question as well as a few selected carbohydrate antigens to serve as control spots. These selected carbohydrate antigens have been characterized on the chip. Their specific antibodies are seen frequently in body fluids of normal individuals;

ii) Repeats and dilutions: Each antigen will be printed at 0.5-1.0 mg/ml and also at a one to ten dilution of the initial concentration for the second concentration. Each preparation at a given concentration will be repeated three times; and iii) Antibody isotype standard curves: Human or murine antibodies of IgG, IgA and IgM isotype of known concentrations will serve as standard curves for antibody detection and normalization.

For each antigen preparation, approximately twenty-five micrograms of purified protein are sufficient for producing this set of testing chips. We designed the following protocol in order to enable a rapid and economic screening: a) Negative elimination; b) Specificity and cross-reactivity; and c) Conventional immunoassay. Preparations of mixed antibodies are made in such a way that a) the total protein concentrations of the mixed antibodies for each subarray staining is identical across subarrays; b) for each antibody preparation, there are series dilutions (~four points); c) antibodies of same species are grouped to avoid frequently occurring cross-neutralization of antibody reactivity among different species and to allow detection of multiple Ig isotypes on the same spots.

a) Negative elimination: A preparation of mixed monoclonal or polyclonal antibodies is applied to stain a subarray. Antibodies derived from the same species can be mixed together to stain a sub-array and a tagged secondary antibody can reveal their specific binding on antigen spots. To take the advantage of the above 8-chamber design, these antibodies are applied in serial dilutions to permit an estimation of their detection sensitivity and specificities;

b) Specificity and cross-antigenic reactivity: A subarray of the antigen chip is stained using distinctly tagged monoclonal or affinity purified antibodies to identify specific antigen spots. This staining allows one to detect specificity as well as potential cross-antigenic reactivity among printed antigens. Such analysis has been detailed previously; and c) Conventional immunoassays to verify microarray results: ELISA, Dot blot, and/or Western Blot is performed. If an antigen is positively detected by an antibody on ELISA but negative or poorly detectable by protein microarray, this may suggest a problem with its on-chip immobilization. The protein may be conjugated to a carrier molecule (such as BSA) to improve its immobilization. If it is ELISA negative but Western positive to a corresponding antibody, the protein may be solubilized in a denaturing solution before printing on the chip.

2. A Full-Scale Biochip Scanning

We have produced a microarray biochip composed of about 4,000 microspots of antigens. In addition to carbohydrate antigens, we printed a large panel of protein antigens. In this design, each antigen or antibody preparation of a given dilution was printed with four repeats in a vertical line of micro-spots on the biochip. This allowed us to visually observe and statistically analyze the reproducibility of microarray printing and staining. The significance and sensitivity of antibody detection for each antigen at a given antigen concentration can also be statistically calculated. Some preparations, for example the gp120 glycoprotein of HIV-1 as highlighted in a square in FIG. 11, were printed from left to right in a series dilution of one to five, beginning at 0.5-1.0 mg/ml and with four dilutions thereafter. These biochips were stained with the uninfected or HIV-1-infected human serum specimens with the methods described above. Pictures of the ScanArray visualization of the multi-color fluorescent staining of biochips are shown in FIG. 11.

(B) Technologies for the Production and Preservation of Long-Lasting Protein Microarrays Given our understanding of protein chemistry, on-chip protein structural alteration, including denaturing or partial denaturation and various degrees of conformational modification, is unavoidable over a long period of time (months to years). Such alteration is generally un-acceptable when a protein chip is made to study the biological function of a protein, such as protein-protein interactions, small molecule transportation, enzymatic reactivities, and cell signaling activity, etc. To maintain these functional properties of proteins, substantial preservation of the native protein structure or conformation is generally necessary. For an immunological application, this situation is, however, significantly different since an antibody may recognize either the native or the denatured/partially denatured antigenic determinants. Antibodies of distinct epitope-binding specificities are frequently elicited in the course of a microbial infection. Technically, the ELISA-based immunoassays are preferential to the detection of antibodies that recognize the native antigenic determinants; the Western blot assays generally directed to the protein structures that are denatured/partial denatured and immobilized on a nitrocellulose membrane or other surfaces with hydrophobic characteristics. The "Western type" of antigenic structures also has large potential in protein chip application since many antigens on Western blot/nitrocellulose strips are stable and suitable for long-term preservation.

Differing from the DNA-based microarray assay, which requires DNA and/or RNA denaturation to allow the A/T or C/G hybridization-taking place, the protein microarray assay requires preservation of protein structures (a general belief in the field). Protein on-chip stability has been considered a critical issue for the development of long-lasting protein microarrays. To address this question of protein stability, we analyzed in a model system, the HIV-1 protein chip (see FIG. 18).

Figure 18:
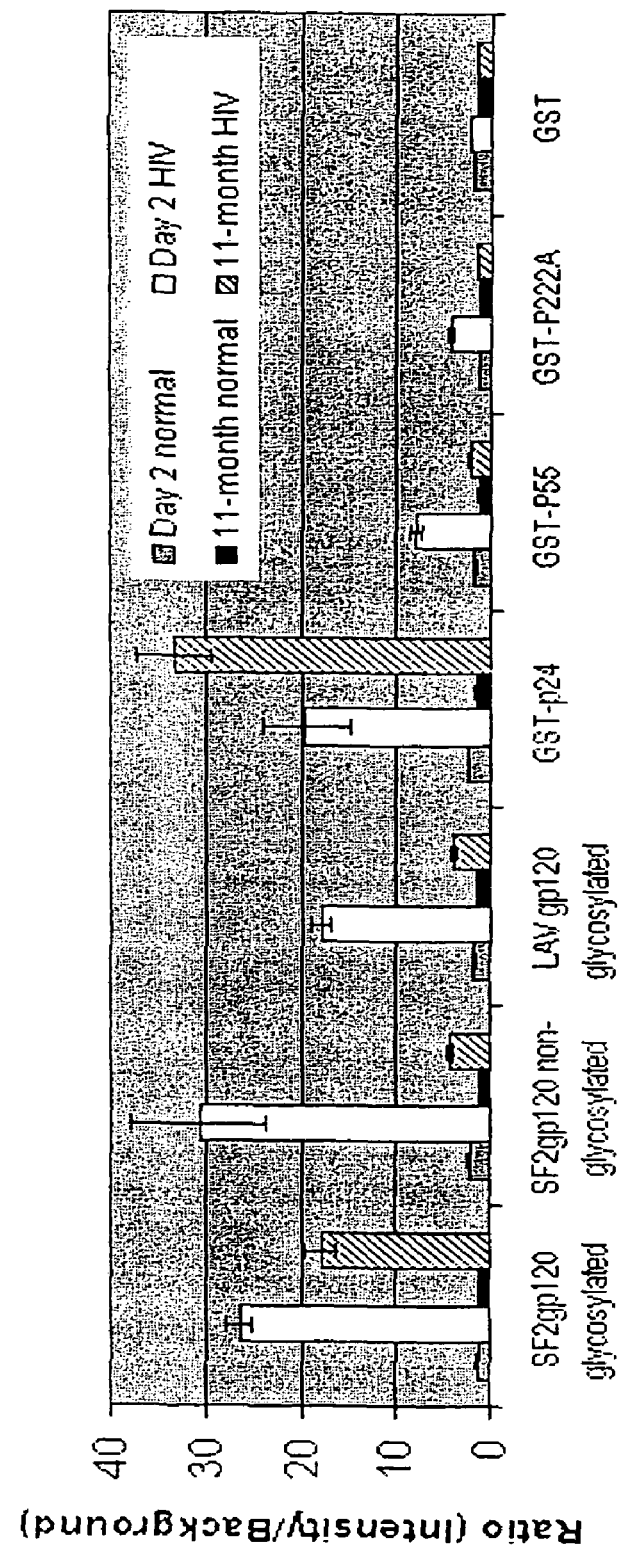

FIG. 18 shows the results from protein microarrays that were printed, air-dried, and stored at room temperature. In one set, slides were stained at day 2 and another set in 11 months after printing. Serum specimens applied for the day 2 staining are identical to those for the 11 month-old slides. This allows a comparative analysis of protein antigenic reactivities on the chips that were stored for different time range, either for two days or for eleven months. Each bar represents the mean of four detections (Ratio of intensity over background). Data were calculated and statistically analyzed as described[9].

This experiment showed that some protein preparations, such as SF2 gp120-glycosylated and GST-gag p24 of HIV-1 preserved their antigenic reactivities quite well after a prolonged storage in air-dried condition at room temperature. Other preparations, including SF2gp120 non-glycosylated, LAV gp120 glycosylated, GST-gag p55 and GST-gag p55/mutant P222A, lost a large proportion of their antigenic reactivities on chip after long-term storage. These observations indicate an existing possibility that production of a long-lasting protein chip using our microarray platform is most likely feasible.

1. Long-Lasting Preservation of Global Patterns of Antibody Reactivities on-Chips To test further this possibility, we characterized a large collection of antigen preparations. Specifically, we stained three sets of biochips that were made identically in the same printing experiment using same antibody preparations at three time points, day 2, eight months, and eleven months after they were made and simply stored at room temperature in air. A clustering analysis-based software was developed by our lab to characterize the antigenic reactivities on-chip in a global manner. Results illustrated in FIG. 19 reveal that although some proteins showed reduced antigenic reactivities on-chip after a long-term storage in air at room temperature, the global patterns of antigenic reactivities remain the same or similar among three different experiments across the three time points: day 2, 8 months and 11 months.

Figure 19:
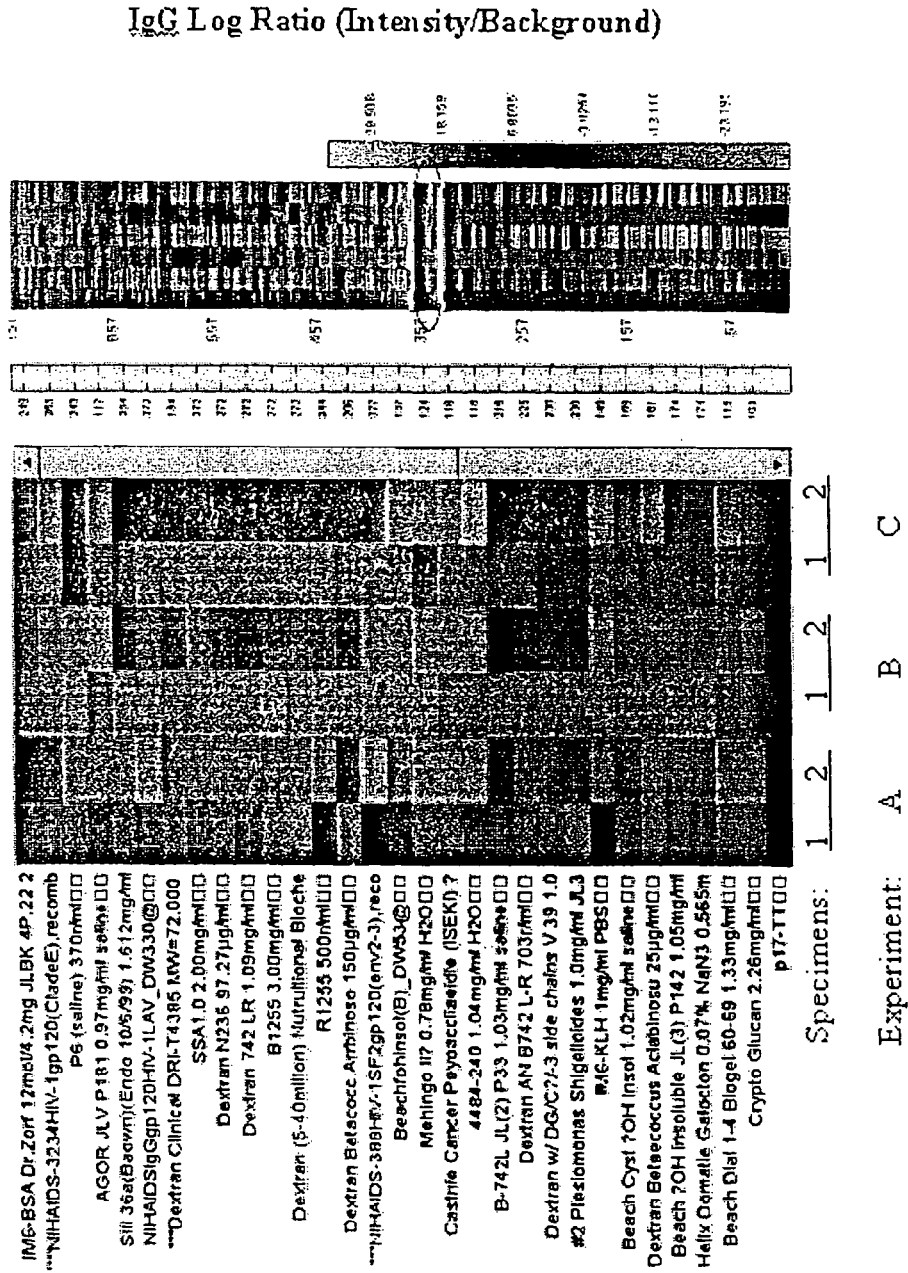
Figure 20:
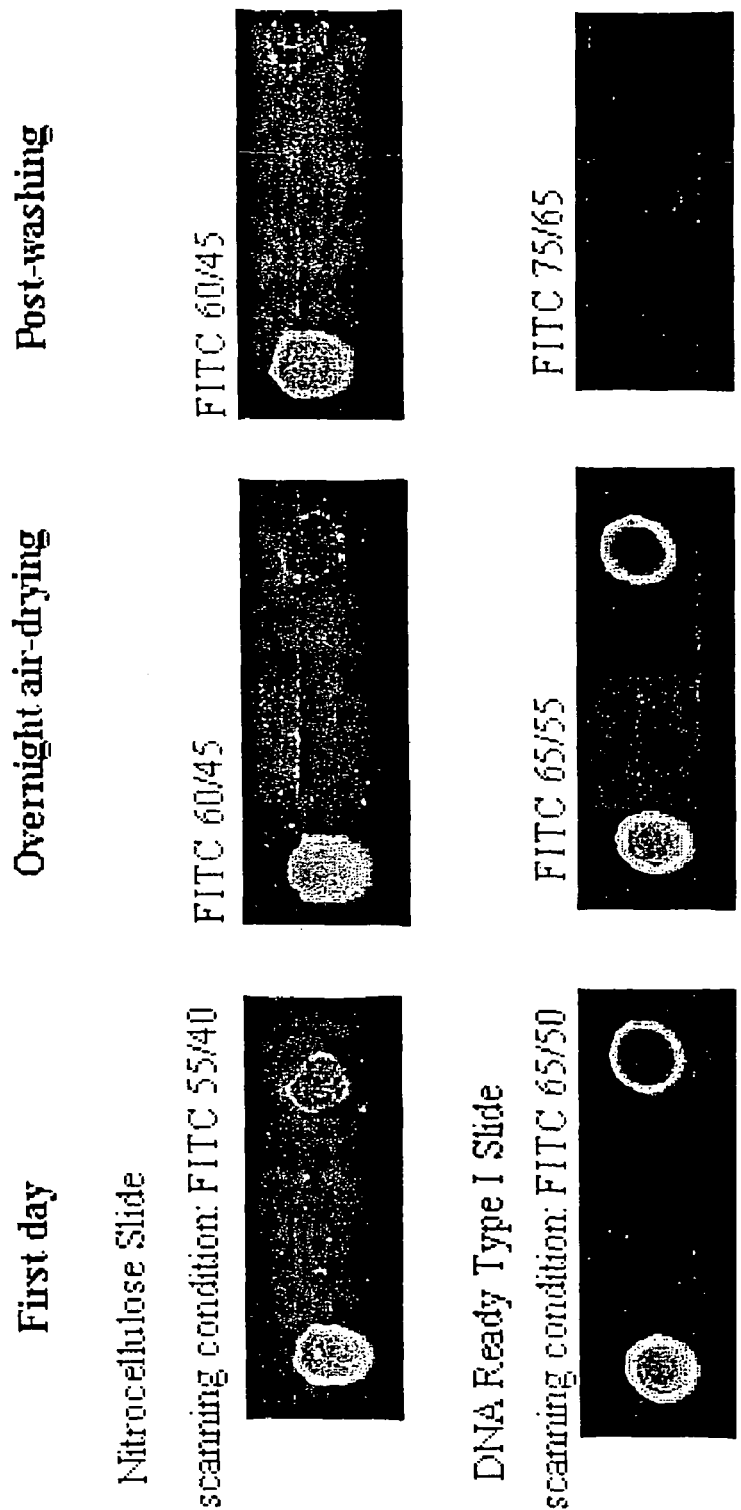
Figure 21:
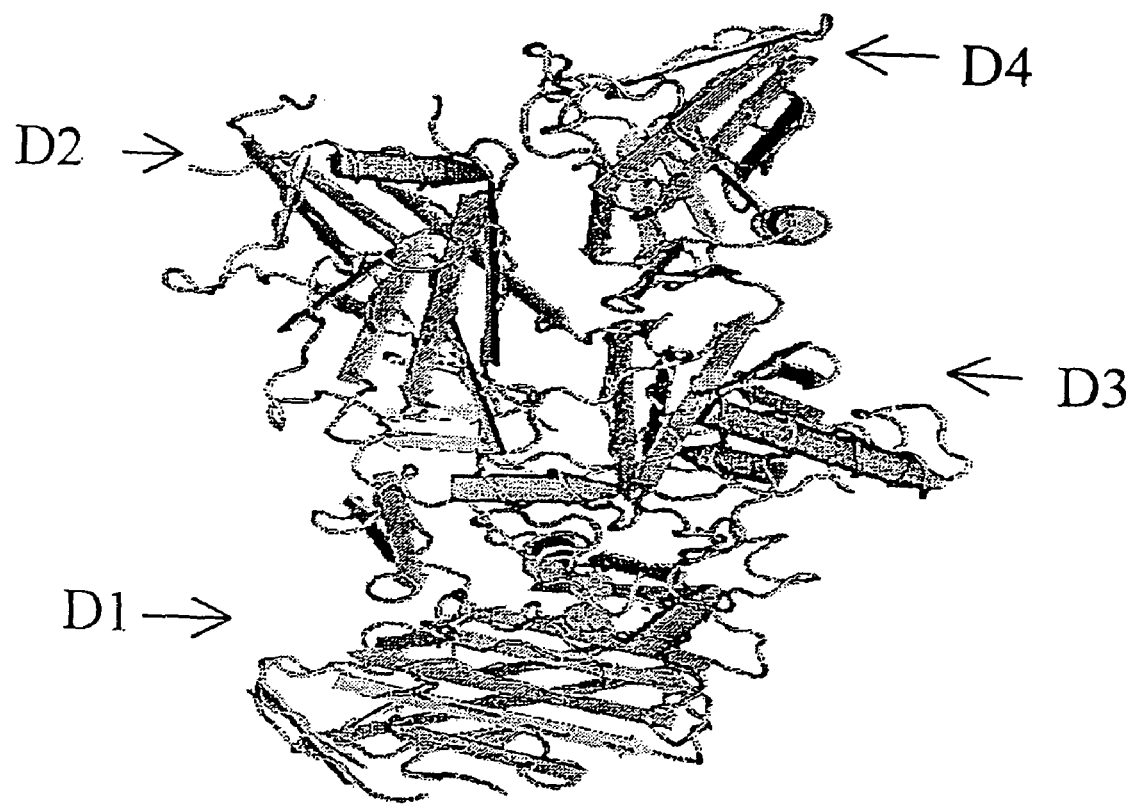
Figure 22:
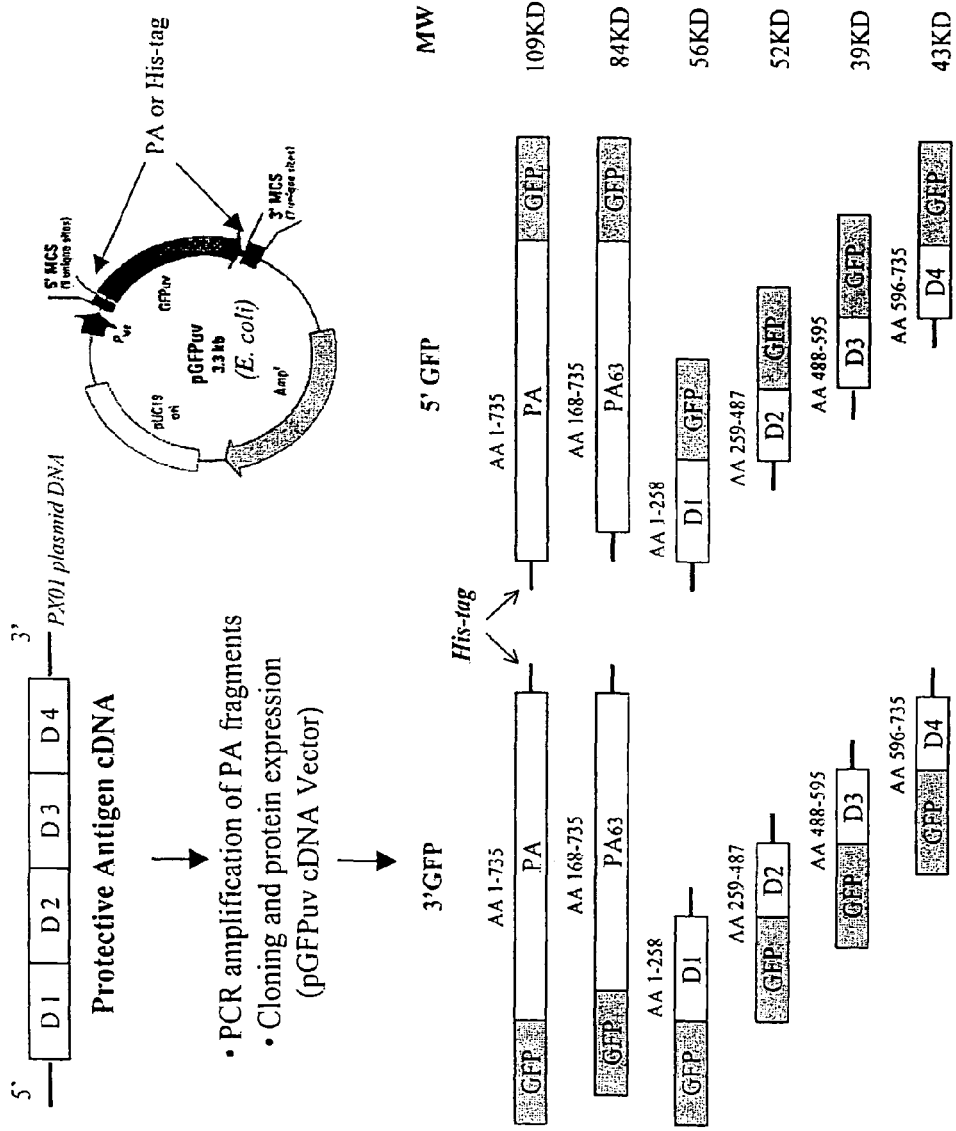

In three replicate experiments, biochips were stained at day 2 (Experiment A), 8 months (Experiment B), or 11 months (Experiment C), using the same specimens, either serum of an uninfected individual or an HIV-1 infected patient. Results were presented as the Log ratio of the intensity over background for each antigen microarray at a given concentration. A hierarchical clustering method is applied on the data under the platform of Matlab. The correlation between color bar and the log ratio of intensity over background is indicated in FIG. 19 (right corner).

2. Methods of Post-Printing Handling to Improve Protein Chip Stability

We have established a few methods for the post-printing treatment of protein chips to improve the stability of our protein chip. Our methods are relatively simple and generally applicable to many protein antigens, including those that have distinct structural characteristics. This is, in fact, a challenge to the proteomic microarray technology. Most, if not all protein antigens, express two general types of antigenic determinants, being either labile or stable on chip. To improve the stability of diagnostic protein chips, two different types of approaches may be considered: methods to stabilize the native structures of protein on chip and methods to remove the labile epitopes and/or to enrich the stable epitopes. We established, therefore, the following approaches to establish a long-lasting antigenic protein microarray:

a) Lyophilizing Protein on-Chip

Many protein preparations can be lyophilized and stably stored at low temperature for a long period of time. We treat our printed protein chips by a step of lyophilizing. We then seal them in a plastic bag and store them at lower temperatures, including 4° C., −20° C., and −80° C. These chips are analyzed as described above after a period of storage (two days, six months and two years). Results are compared with those of experiment 1 whereby the printed chips are placed at room temperature in the air-dried condition. A technical concern is whether the process of lyophilizing sucks off a proportion of printed proteins. If a significant signal reduction is seen, a period air-drying the freshly made chip can be employed to avoid the signal reduction.

b) Dessication of Protein Microarrays:

Place a protein chip in a desiccator for a period of five to ten days in the presence of a desiccating reagent without a vacuum. Then stain the chip with antibodies to probe corresponding antigenic determinants. We predict that some but not all antigenic structures/protein epitopes are sensitive to dehydration. ELISA and Western blot assay are conducted to further characterize the two classes of antigenic structures, the dehydration sensitive and the dehydration resistant antigenic determinants.

c) Hydration of Protein Microarrays:

Prepare three sets of protein chips by covering them with a thin layer of "sticky" aqueous solution, i.e., 40% glycerol in 1×PBS. One set (six chips) is stored at 4° C., one set at −20° C. and the last set at −80° C. After a period of storage (two days, six months, and two years), two chips/sixteen sub-arrays are stained and the data analyzed as described above.

In Western blot diagnosis of HIV-1 and many other infectious diseases, serum antibodies of infected individuals are found in many cases to be specific to denatured or partially denatured protein antigens. We, however, for the first time, take advantage of this host immunity to develop a novel protein chip assay. Differing from Western blot, the protein chips can substantially extend the spectrum of pathogens that can be detected in a single assay. In addition, a chip assay is rapid, high throughput, and economic. It requires only a few microliters of serum specimen. Theoretically, similar structural alteration may also occur in vivo in the cellular events of antigen processing/trafficking during a natural infection, generating antigenic structures that differ from those expressed by the native proteins. Such structures are still "foreign" to a host and capable of induction of specific antibody responses. The potential of this category of antigenic structures for diagnostic use, especially in association with the high throughput protein microarray technology, is yet to be explored.

In summary, protein microarrays can be treated in three different ways, including lyophilizing, desiccation, and hydration, and stored for a various periods of time, ranging from two days to two years.

(C) Green Chip Technology—the Second Generation of Protein Chips

As described above, we have established technologies to explore the available antigens and antibodies to rapidly establish protein antigen-based microarrays to meet the urgent needs of biodefense. The potential of these approaches is, however, limited by the availability of pathogen-specific antigens and antibodies. Here, we apply the state-of-art technologies of protein engineering to facilitate the development of protein microarrays. Specifically, we a) introduce the technology of green fluorescent protein (GFP) in our next generation of protein microarrays, the Green Chip Technology; b) establish a molecular engineering-based strategy to produce recombinant proteins that fluoresce on the chip and are capable of displaying stable antigenic determinants on the surface of a microarray. This method can be applied to many molecular targets whose nucleotide sequences and/or structural information are available. This method is, therefore, designed to extend the repertoire of pathogen signatures for the production of diagnostic microarrays. We use the protective antigen (PA) of *B. anthracis* as a model to demonstrate this technology.

Efficacy of protein immobilization on a nitrocellulose-coated microslide depends on the physicochemical property of protein molecules. Since only noncovalent molecular interactions are involved, a common influencing factor is the molecular weight (MW) of a target molecule. In some circumstances, protein antigens or pathogen-specific antigenic determinants are too small to be immobilized on the chip without altering their antigenic reactivities. We, therefore, fuse a target molecule to a carrier protein molecule to improve its surface adhering property. In this case, we select a fluorescent carrier molecule, the green fluorescent protein (GFP). GFP was originally isolated from the biolyminescent jellyfish *Aequorea Victoria*[44]. The protein, as well as its variants, have been successfully expressed in various other organisms and have been used as a detection system. The two variants that are readily available as purified proteins are EGFP (enhanced green fluorescent protein) and GFPuv (UV-optimized GFP variant). Their excitation maxima are 488 and 395 nm, respectively, while their emission maxima are 507 and 509 nm, respectively.

We tested purified GFPuv on our protein microarray chip. It generates bright fluorescent signal upon excitation at fluorescence channel (488 nm) but not at Cy3 (552 nm) and Cy5 (633 nm) channels of a microarray scanner (GSI SA5000) (FIG. 20 and table 5). This makes it practical to use the FITC channel to monitor protein stability, printing quality, and data normalization and, while using Cy3, Cy5 and other GFP negative channels to detect antigen-antibody interaction on the same spots. In addition, the GFP signal is retained on the chip after it is air-dried and extensively washed (FIG. 20). Introduction of GFP to the protein chip 'up-grades" our protein chip technology. It provides not only an effective and convenient means to monitor the quality of protein microarrays but also an internal control for each microspot. The latter is greatly important for data processing and data mining and therefore will generally improve the quality of protein chips.

1. The PA Antigen of *B. anthracis* as a Model for the Green Chip Technology

PA is the central component of the three-part lethal toxin of *Bacillus anthracis*. It binds to a specific cellular receptor and forms toxic, cell bound complexes with edema factor (EF) and lethal factor (LF)[14-16]. It was named PA since it acted protective when an animal was injected with the protein and then challenged by the lethal pathogen *B. anthracis*. PA itself is a good antigen for eliciting antibody responses in a number of mammalian species, making it an important vaccine against anthrax[45]. The crystal structure of monomeric PA at 2.1 Å resolution and the water-soluble heptamer at 4.5 Å resolution have been resolved (FIG. 21)[46]. PA is, therefore, an ideal molecule model for studying the relationship between protein structure and its antigenic reactivity.

Our investigation is directed at the recognition of the antigenic determinants of PA that are stable on a chip, useful for vaccine evaluation, and highly specific for pathogen recognition. We focus on the relationship between structure and the on-chip antigenic reactivity of the molecule. Specifically, we ask a) whether the structures that are buried in its native configuration are useful for protein chips, and b) whether the structures that are displayed on the surface in the native form are stable and long lasting on chip. The structures hidden in a native protein may become exposed in vivo by cellular or enzymatic processing or in vitro owing to its on-chip structural alteration. Our working hypothesis is that such hidden structures are previously unrecognized pathogen signatures and are suitable for the production of long-lasting diagnostic protein chips. In PA, an important "hidden structure" is the surface of $PA_{63}$, which is masked by the N-terminal 20K fragment of PA ($PA_{20}$). Release of this fragment from PA leads to heptamer formation by $PA_{63}$.

Our overall experimental design uses antibodies of distinct epitope binding specificities to recognize the antigenic determinants of PA, to monitor their possible alteration on chip during storage, and thereby identify the stable antigenic structures for long-lasting protein chips. Experimentally, we a) produce a panel of recombinant proteins of PA and its derivatives; b) produce the domain-specific PA protein microarrays using these recombinant PAs; c) immunize mice using PA and its conjugates to elicit antibody responses and monitor the time course of the response by PA protein chips; and d) generate monoclonal antibodies to ensure the availability of antibodies of various binding specificities, including those that bind PA specifically by Western Blot and those specific for the antigen on ELISA.

2. GFP-Fusion Proteins of PA, its Derivatives, and their Fluorescent Protein Microarrays a) Construction of expression vectors, protein induction and purification: Construct a panel of twelve GFP-PA fusion proteins as outlined in FIG. 22. Briefly, six sets of PCR primers have been designed according the published nucleotide sequences of PA (on the PX01 plasmid) and the domain structure of the protein. Use a cDNA clone containing the full-length PA as a template for PCR amplification to produce six PCR fragments, including a full-length PA, an N-terminal truncated PA (PA$_{63}$), and domain 1 to 4. These PCR fragments are subcloned into an *E. coli* expression vector, pGFPuv cDNA Vector (BD/Clontech), to express corresponding GFP fusion proteins. In vector design, the expressed fusion protein will be accumulated intracellularly as GFP alone. In addition, a His-tag can be cloned either at the N-terminal or the C-terminal of a recombinant protein, allowing protein purification using Ni-NTA column/resin under either denatured or native condition as described by the manufacture (QIAGEN Inc., USA). This will enable the binding of protein on Ni-NTA ELISA plate and Western blot using anti-His antibodies. Additional methods of purification include: i) the native condition of purification; ii) denaturing conditions; and iii) the GFPuv protein is resistant to the 8M Urea, which serves as one of the alternative methods for GFP-fusion protein purification.

b) Printing and validating the fluorescing PA microarrays: Methods for microarray printing, preservation, scanning, and data processing are the same as described above. Given our current knowledge, these GFP-fusion proteins are as bright as GFP alone. If some clone loses its fluorescent property, anti-GFP antibody can be used to detect them on the chip. Proteins may be solubilized using a solution containing 8 M urea. We observed previously that proteins solubilized in this way can be immobilized on a nitrocellulose membrane or on an ELISA plate. Printing is on the 8-chamber subarray system as described above. Protein chips are stored under different conditions as described above and analyzed two days, six months, and one year after printing. Antibody staining is detailed below using a panel of monoclonal and polyclonal antibodies.

c) Animal immunization and production of monoclonal antibodies: A panel of polyclonal and monoclonal anti-PA antibodies is currently available. These reagents are tested by ELISA and by Western blot to identify different categories of specificities: a) Recognize native epitope: ELISA strongly positive, but Western negative or weakly positive to PA; b) Recognize denatured/partially denatured epitope: Western strongly positive, but ELISA negative or weakly positive; and c) Recognize the stable epitopes: Both methods strongly positive. These are relative ways of classification but have been proven useful for predicting an antigenic structure.

3. "Green Chip Technology" to Reveal the Hidden Antigenic Determinants

As described above, we believe that the on-chip protein structural alteration, including denaturation or partial denaturation and various, degrees of conformational modification, is unavoidable in the course of a long period of time (months to years). Such alteration is, however, not necessarily a limiting factor to the diagnosis of infectious disease and other immunological disorders on a protein chip. We reason that antibodies elicited by an antigenic stimulation, either by a microbial infection or by a vaccination, have the potential to recognize multiple antigenic structures, including either the native/conformational sensitive antigenic determinants or the denatured or partially denatured/conformationally insensitive antigenic determinants. For instance, the ELISA-based immunoassays preferentially detect antibodies that recognize the native antigenic determinants; the Western blot assays are directed to the protein structures that are denatured/partially denatured and immobilized on a nitrocellulose membrane or other surfaces with hydrophobic characteristics. "Western-like" antigenic structures have high potential in protein chip application since they are generally stable and suitable for long-term preservation. Given the complexity of protein structure and the question regarding their antigenic reactivity, we use the protective antigen (PA) of *B. anthracis* as a model and example for other important microbial antigens.

Experimentally, we a) take advantage of our green chip technology to monitor the structural stability and quality of printed protein chips by capturing its GFP signal on the chip over periods of time; b) use a large panel of monoclonal and polyclonal antibodies specific for distinct antigenic determinants of PA, including specificities to the native structures as well as reactivities directed to the denatured/partially denatured structures. This type of on-chip epitope scanning is high throughput. We perform it at defined points in time as described above.

4. Use of Two GFP Variants, EGFP and GFPuv, on Microarrays

We demonstrated that two molecular variants of GFP, EGFP (enhanced GFP) and GFPuv (UV-optimized GFP variant), are applicable for our platform of chip fabrication. These variants were specially included for this investigation since their fluorescing activities are protein conformation dependent. Detection of the signals that they generated over times provides a simple and efficient method to monitor their structural stability on-chip. Results summarized in FIG. 30 show that these GFP proteins were stably immobilized on the nitrocellulose slides and were fluorescing on-chip after air-drying, extensive washing and prolonged storage at room temperature. These properties are similar to those of FITC-labeled polysaccharides, as well as the Cy3- and Cy5-conjugates of streptavidin that were printed and tested in the same experiments.

III. A Procedure for Production of Epitope-Specific Carbohydrate Microarrays

This section is directed to the high throughput production of the oligosaccharide-based, epitope-specific carbohydrate microarrays. This invention makes it possible to produce a glycochip whereby a single type of glycoconjugate, the oligosaccharide-polyacrylomide conjugate, is utilized to display a large repertoire of oligosaccharides of distinct structures.

(A) αGal Anti-αGal System as a Model

We have chosen the αGal anti-αGal system as a model to establish the technology of the oligosaccharide-based, epitope-specific carbohydrate microarrays. Since αGal is a key antigenic determinant that is responsible for the hyperacute rejection in animal to human xenotransplantation, the microarrays produced by this investigation are valuable for monitoring such anti-xenoantigenic responses.

We printed both αGal-protein conjugates (data not shown) and αGal-polyacrylamide conjugates on nitrocellulose coated glass slides and then stained the microarray with αGal-specific antibodies. Since we have already established that glycoproteins can be stably immobilized on the nitrocellulose slide, the use of αGal-protein conjugates in this study serves as a control for neoglycopolymers.

1. Microarray Experiment-1: Lectin Staining

To validate whether the αGal-sugar epitopes are displayed by the PAGE-conjugates, we spotted a panel of α-Gal-PAGE conjugates of defined structures on a nitrocellulose-coated glass slide.

We spotted PAGE-based neoglycoconjugates at an initial concentration of 0.6 mg/ml and then diluted the conjugates in serial dilutions of 1:4. We stained the microarray chips using a lectin that is specific for the sugar chain. The Banderiraea Simplicifolla BS-1 lectin (Sigma) is used in FIG. 23A. The lectin was coupled with a biotin molecule. The microspots-captured lectin was thus revealed by a streptoavidin-Cy5 conjugate. Glycoconjugates utilized in this study include: (i) DW450 phenyl α-Galactopyranosyl-(1-3) b-D-galactopyranosyl-(1-4)-1-thio-b-D-glucopyranoside; (ii) DW451α-Galactosyl-2; (iii) DW452 α-Galactosyl-3; (iv) DW453 α-Galactosyl-4; (v) DW454 polylactose (1/2.5); (vi) DW455 α-Gal polymer A; (vii) DW456 α-Gal polymer B; (viii) DW457 α-Gal polymer C; (ix) DW458 α-Gal polymer D; (x) DW459 α-Gal polymer E; and (xi) DW460 α-Gal polymer F.

Figure 23:
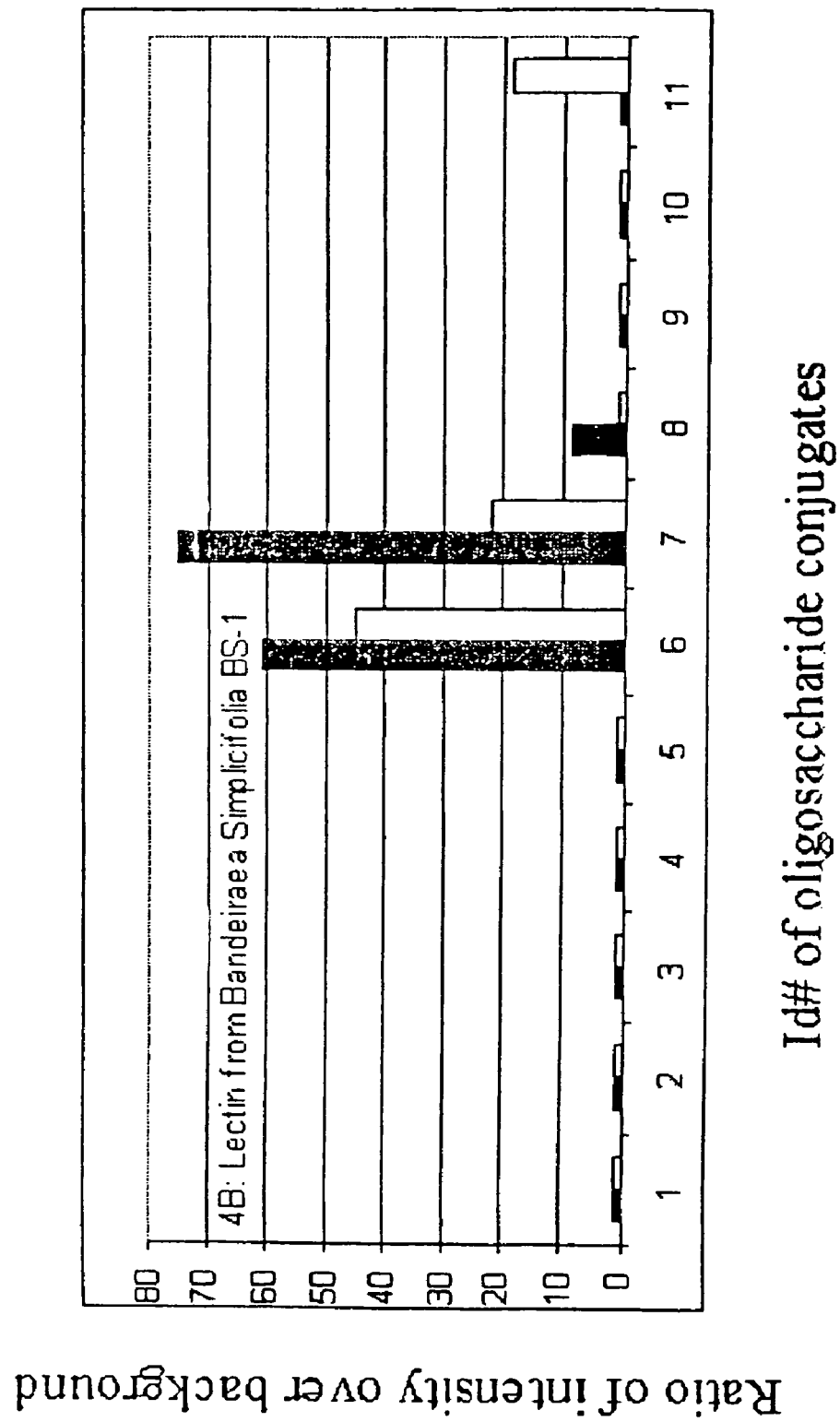
Figure 23:
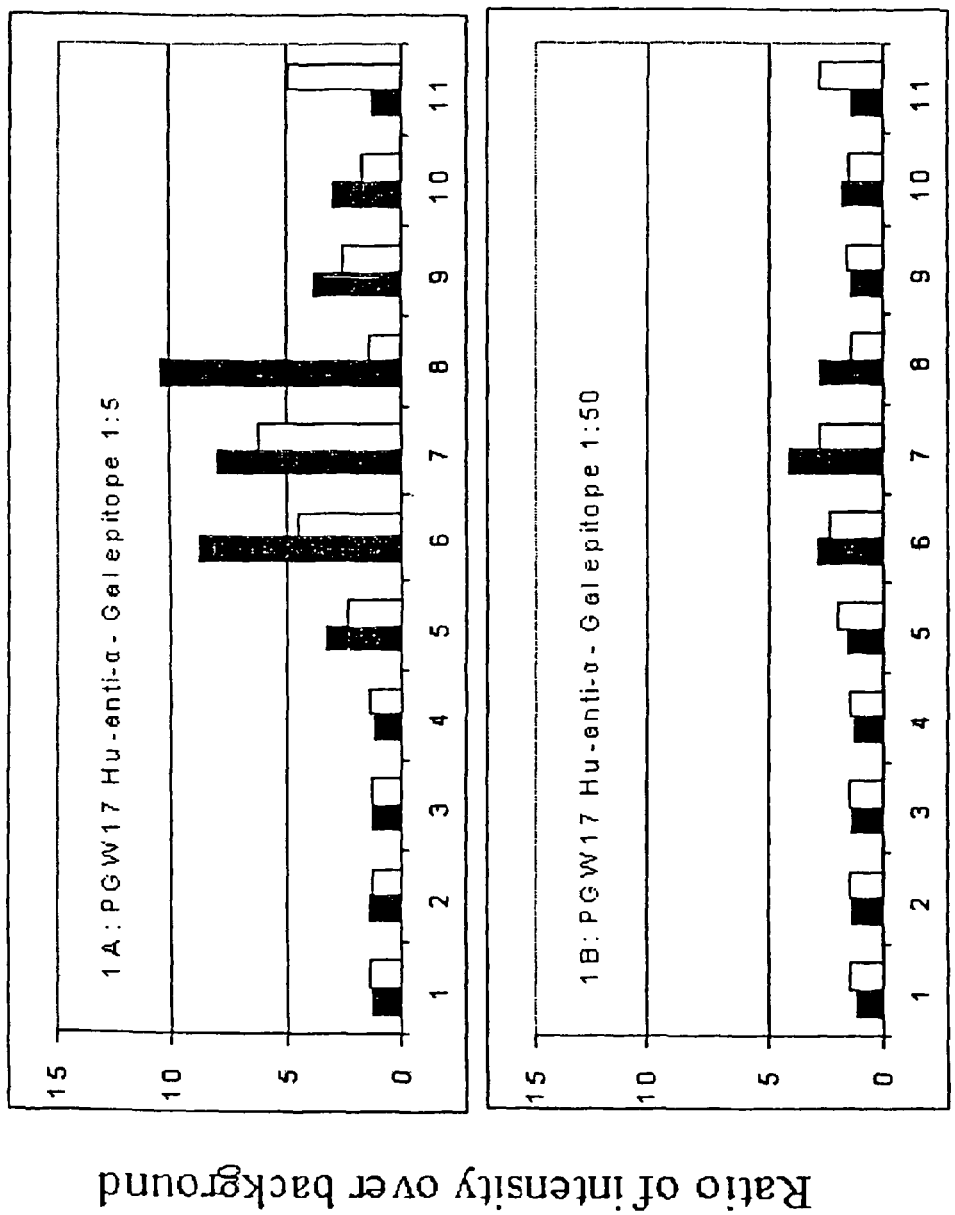

Results shown in FIG. 23A demonstrate that the αGal-sugar epitopes are displayed by the PAGE-conjugates and are specifically detected by the lectin Banderiraea Simplicifolla BS-1.

2. Experiment-2: Human Antibody Characterization of the αGal-Glycochips

To investigate further whether the PAGE-conjugates of oligosaccharides are applicable for our platform of microarray production, we stained the microarrays with a preparation of affinity purified human anti-α-Gal antibodies at a 1:5 dilution (FIG. 23B upper) and at 1:50 (FIG. 23B bottom). The captured human IgG antibodies were then stained with an anti-Hu-IgG-Biotin conjugate, and subsequently stained using Av-Cy5 at the 1:250 dilution. Data for three repeats of the experiment were statistically analyzed.

Glycoconjugates utilized in this study include: (i) DW450 phenyl α-Galactopyranosyl-(1-3) b-D-galactopyranosyl-(1-4)-1-thio-b-D-glucopyranoside; (ii) DW451α-Galactosyl-2; (iii) DW452 α-Galactosyl-3; (iv) DW453 α-Galactosyl-4; (v) DW454 polylactose (1/2.5); (vi) DW455 α-Gal polymer A; (vii) DW456 α-Gal polymer B; (viii) DW457 α-Gal polymer C; (ix) DW458 α-Gal polymer D; (x) DW459 α-Gal polymer E; and (xi) DW460 α-Gal polymer F.

Results shown in FIG. 23B illustrate that the αGal-sugar epitopes are displayed by the PAGE-conjugates and are specifically detected by a preparation of affinity purified human anti-αGal antibodies. This experiment provides direct information regarding the use of this sugar chip in detecting human anti-αGal antibodies. Therefore, this sugar chip itself is a means for monitoring the hyperacute rejection in animal-to-human xenotransplantation that is mainly mediated by human anti-αGal antibodies. The potential of this epitope-specific sugar chip is, however, far beyond this specific application.

3. Experiment-3: Interaction Between Lectin BS-1 and the α-Gal Sugar Epitopes is Epitope-Density Dependent We spotted α-Gal-PAGE conjugates at an initial concentration of 0.6 mg/ml and then diluted the conjugates in serial dilutions of 1:3. We stained the microarray chips using a lectin that is specific for the sugar chain. The Banderiraea Simplicifolla BS-1 lectin (Sigma) is used in FIG. 29. The lectin was coupled with a biotin molecule. The microspots-captured lectin was thus revealed by a streptavidin-Cy5 conjugate.

Figure 29:
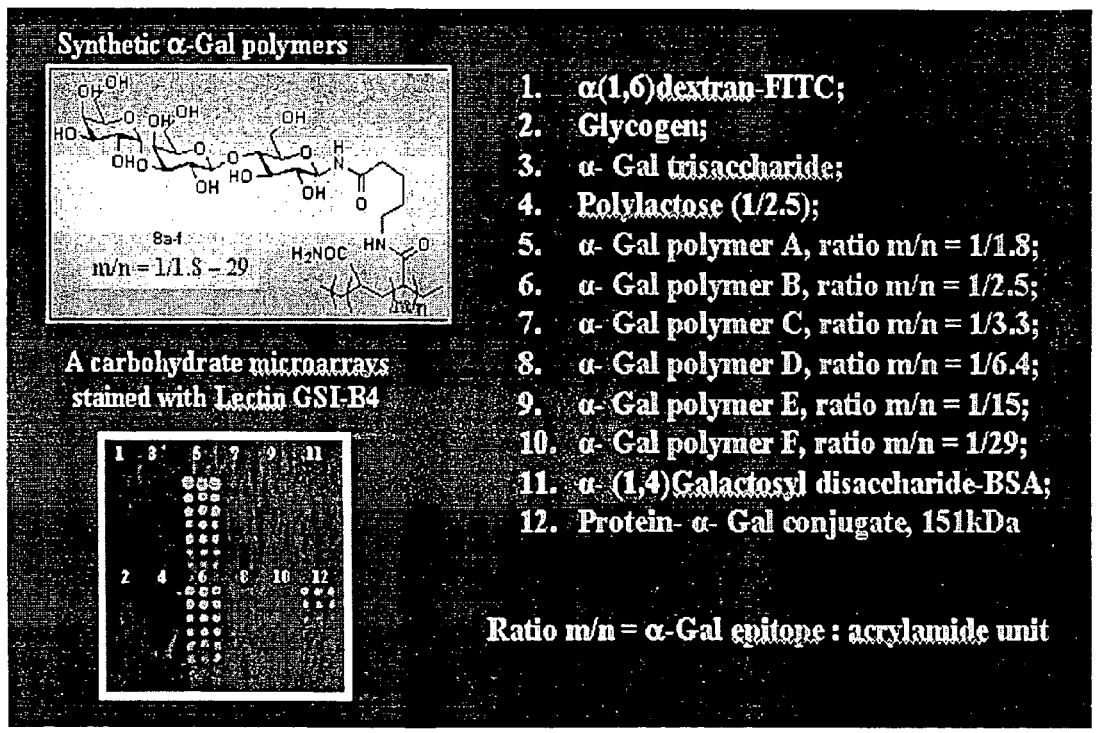
Figure 30:
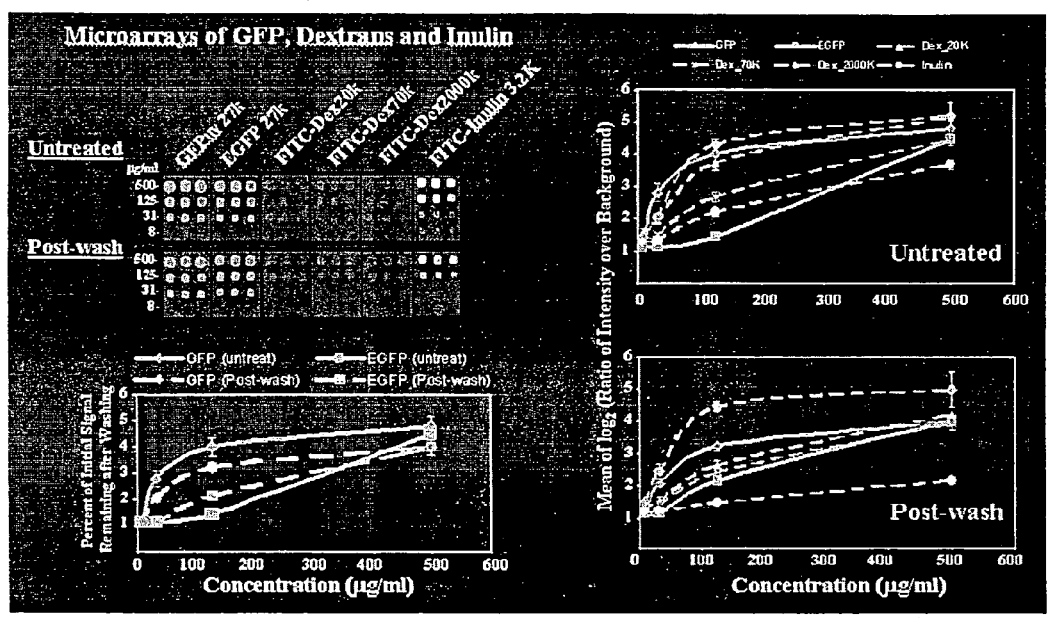

Results shown in FIG. 29 demonstrate that the α-Gal-sugar epitopes are displayed by the polyacrylamide-conjugates and are specifically detected by the lectin Banderiraea Simplicifolla BS-1. In addition, we demonstrated, for the first time, on biochips that the molecular interaction between Lectin BS-1 and the α-Gal-sugar epitopes is epitope-density dependent. Such sugar chain specific molecular recognition can only take place when the molar ratio of oligosaccharide:carrier is greater than 1:2.5. This finding demonstrated a great advantage of this platform of oligosaccharide microarrays since it allows us to produce an epitope-specific carbohydrate microarray with various sugar chain densities and thereby mimic the in vivo cell-cell recognitions that are mediated by sugar chains and their cellular receptors.

REFERENCES

1. Volchkov, V. E. Ebola virus, complete genome. *Institute of Virology, Philipps-University* (2000).
2. Shchelkunov, S. N., Totmenin, A. V. and Sandakhchiev, L. S. Analysis of the nucleotide sequence of 23.8 kbp from the left terminus of the genome of variola major virus strain India-1967. *Virus Res.* 40, 169-183 (1996).
3. Okinaka, R. T. et al. Sequence and organization of pXO1, the large *Bacillus anthracis* plasmid harboring the anthrax toxin genes. *J Bacteriol* 181, 6509-6515. (1999).
4. Brown, P. O. & Botstein, D. Exploring the new world of the genome with DNA microarrays. *Nature. Genetics.* 21, 33-37 (1999).
5. DeRisi, J. L., Iyer, V. R. & Brown, P. O. Exploring the metabolic and genetic control of gene expression on a genomic scale. *Science.* 278, 680-686 (1997).
6. Ramsay, G. DNA chips: state-of-the art. *Nature. Biotechnology.* 16, 40-44 (1998).
7. MacBeath, G. & Schreiber, S. L. Printing proteins as microarrays for high-throughput function determination. *Science* 299, 1760-1763 (2000).
8. Lueking, A. et al. Protein microarrays for gene expression and antibody screening. *Analytical. Biochemistry.* 270, 103-111 (1999).
9. Wang, D., Liu, S., Trummer, B. J., Deng, C. & Wang, A. Carbohydrate microarray leading to the recognition of cross-reactive molecular markers of microbes and host cells. *Nature Biotechnology* 20 (2002).
10. Grifantini, R. et al. Previously unrecognized vaccine candidates against group B meningococcus identified by DNA microarrays. *Nat Biotechnol* 20, 914-921. (2002).
11. Gladstone, G. P. & Walton, E. Effect of iron on the bactericidal proteins from rabbit polymorphonuclear leukocytes. *Nature* 227, 849-851. (1970).
12. Strange, R. E. & Belton, F. C. Studies on a protective antigen produced in vitro from *bacillus anthracis*: Purification and chemistry of the antigen. *Bri. J. Exp. Pathol.* 35, 153-165 (1953).
13. Ezzell, J. W., Jr., Abshire, T. G., Little, S.F., Lidgerding, B. C. & Brown, C. Identification of *Bacillus anthracis* by using monoclonal antibody to cell wall galactose-N-acetylglucosamine polysaccharide. *J Clin Microbiol* 28, 223-231. (1990).
14. Blaustein, R. O., Koehler, T. M., Collier, R. J. & Finkelstein, A. Anthrax toxin: channel-forming activity of protective antigen in planar phospholipid bilayers. *Proc Natl Acad Sci USA* 86, 2209-2213. (1989).
15. Thorne, C. B. *Bacillus anthracis*. In *Bacillus subtilis and Other Gram-positive Bacteria*, ed. AL Sonenshein, J A Hoch, R Losick., 113-124 (1993).
16. Escuyer, V. & Collier, R. J. Anthrax protective antigen interacts with a specific receptor on the surface of CHO-K1 cells. *Infect Immun* 59, 3381-3386. (1991).
17. Mourez, M. et al. Designing a polyvalent inhibitor of anthrax toxin. *Nat Biotechnol* 19, 958-961. (2001).
18. Deng, C., Wang, A., Wang, D. & Zhang, P. in Talks on DIMACS Workshop on Analysis of Gene Expression Data. DIMACS Piscataway, N.J.; 2001).
19. Deng, C., Zhang, P., Wang, A., Trummer, B. & Wang, D. in Proceedings. of IEEE International Joint Conference on Neural Networks Hawaii, U.S.A.; 2002).

20. Ramdas, L. et al. Sources of nonlinearity in cDNA microarray expression measurements. *Genome Biol* 2 (2001).
21. Kim, S. et al. General nonlinear framework for the analysis of gene interaction via multivariate expression arrays. *J Biomed Opt* 5, 411-424. (2000).
22. Tseng, G. C., Oh, M. K., Rohlin, L., Liao, J. C. & Wong, W. H. Issues in cDNA microarray analysis: quality filtering, channel normalization, models of variations and assessment of gene effects. *Nucleic Acids Res* 29, 2549-2557. (2001).
23. Jain, A. K., Duin, R. P. W. & Mao, J. Statistical Pattern Recognition: A Review. *IEEE TRANSACTIONS ON PATTERN ANALYSIS AND MACHINE INTELLIGENCE* 22, 4-37 (2000).
24. Nadler, M. & Smith, E. P. Pattern recognition engineering. (John wiley & Sons Inc., New York; 1993).
25. Bow, S.-T. Pattern recognition and image preprocessing. (Marcel Dekker, Inc, New York; 1992).
26. Alon, U. et al. Broad patterns of gene expression revealed by clustering analysis of tumor and normal colon tissues probed by oligonucleotide arrays. *Proc Natl Acad Sci USA* 96, 6745-6750. (1999)
27. Ben-Dor, A. Clustering gene expression patterns. *Journal of Computational Biology* 6, 281-297 (1999).
28. Heyer, L. J., Kruglyak, S. & Yooseph, S. Exploring expression data: identification and analysis of coexpressed genes. *Genome Res* 9, 1106-1115. (1999).
29. Carr D B, Somogyi R & GS, M. Templates for Looking at Gene Expression Clustering. *Statistical Computing and Graphics Newsletter* 8, 20-29 (1997).
30. Michaels, G. S. et al. Cluster analysis and data visualization of large-scale gene expression data. *Pac Symp Biocomput*, 42-53. (1998).
31. Eisen, M. B., Spellman, P. T., Brown, P. O. & Botstein, D. Cluster analysis and display of genome-wide expression patterns. *Proc Natl Acad Sci USA* 95, 14863-14868. (1998).
32. Butte, A. J. & Kohane, I. S. Mutual information relevance networks: functional genomic clustering using pairwise entropy measurements. *Pac Symp Biocomput*, 418-429. (2000).
33. DeRisi, J. et al. Use of a cDNA microarray to analyse gene expression patterns in human cancer. *Nat Genet* 14, 457-460. (1996).
34. Schena, M. Quantitative monitoring of gene expression patterns with a complementary DNA microarray. [see comments.]., (1995).
35. Schena, M. et al. Parallel human genome analysis: microarray-based expression monitoring of 1000 genes. *Proc Natl Acad Sci USA* 93, 10614-10619. (1996).
36. Vapnik, V. N. Statistical learning theory. (John Wiley & Sons, New York; 1998).
37. Vapnik, V. N. An overview of statistical learning theory. *IEEE TRANSACTIONS ON NEURAL NETWORKS* 10, 988-999 (1999).
38. Burges, C. J. C. A tutorial on support vector machines for pattern recognition. *Data Mining and Knowledge Discovery* 2, 121-167 (1998).
39. Su, A. et al. Molecular classification of human carcinomas by use of gene expression signatures. *Cancer Res.* 61, 7388-7393 (2001).
40. Brown, M. P. S. et al. Knowledge-based analysis of microarray gene expression data by using support vector machines. *PNAS* 97, 262-267 (2000).
41. Furey, T. S. et al. Support vector machine classification and validation of cancer tissue samples using microarray expression data. *Bioinformatics* 16, 906-914. (2000).
42. Ramaswamy, S. et al. Multiclass cancer diagnosis using tumor gene expression signatures. *Proc Natl Acad Sci USA* 98, 15149-15154. (2001).
43. Fried, R., Gather, U. & Imhoff, M. Online pattern recognition in intensive care medicine. *Proc AMIA Symp*, 184-188. (2001).
44. Chalfie, M. Green fluorescent protein. *Photochem Photobiol* 62, 651-656. (1995).
45. Reuveny, S. et al. Search for correlates of protective immunity conferred by anthrax vaccine. *Infect Immun* 69, 2888-2893. (2001).
46. Petosa, C., Collier, R. J., Klimpel, K. R., Leppla, S. H. & Liddington, R. C. Crystal structure of the anthrax toxin protective antigen. *Nature* 385, 833-838. (1997).
47. Peterson, L. Factor analysis of cluster-specific gene expression levels from cDNA microarrays. *Comput Methods Programs Biomed* 69, 179. (2002).

Sixth Series of Experiments

I. Introduction

Microorganisms express carbohydrate-containing macromolecules of different molecular configurations, including polysaccharides, glycolipids and glycoproteins. Carbohydrate structures play critical roles in the entry and colonization of microbes, their host recognition, and induction of immune responses[1-5]. They are, therefore, important molecular targets for vaccine development. A notable example is vaccination with the protein-conjugates of *Haemophilus influenza* type b polysaccharide that resulted in the decline in the incidence of *H. influenza* meningitis and other infections in infants and children[6, 7]. Presence of polysaccharides and glycoproteins in *B. anthracis* has been recognized for some time[8-10]. Whether these carbohydrate structures are suitable targets for anthrax vaccination is, however, an open question. This issue will be discussed in association with their biological roles in the life cycle of the bacteria, chemical and immunological characteristics of these molecules, and recent experimental evidence that indicates the potential of a successful carbohydrate-based anthrax vaccination strategy.

(A) Carbohydrate Structures are Expressed at Various Stages of the Life Cycle of *B. anthracis*

The life cycle of *Bacillus anthracis* (FIG. 8), at various stages of development, exposes a number of carbohydrate molecular targets that are accessible to antibodies or lectins in solution.

(1) Dormant Spore

At first, the spore surface interacts with the host. A loosely fitting exosporium composed of protein, lipid, and carbohydrate is observed outside the spore coat. Two exosporium-specific major glycoproteins have been described for *B. cereus*[11,12]. Staining of spores of *B. cereus* and *B. anthracis* by specific lectins suggested the presence of carbohydrate structures on the surface of their spores[10]. Information regarding their carbohydrate structures is, however, currently unavailable.

(2) Phagocytosis and Spore Germination

After entry into the host, spores are taken up by macrophages and are transported to the regional lymph nodes that typically drain the site of inoculation[13], [14]. Germination of *B. anthracis* spores may occur intracellularly, such as in the phagolysosome of alveolar macrophages or extracellularly in the presence of serum and elevated $CO_2$. Whether and how the intracellular germinating spores circumvent the antimicrobial environment of the phagolysosome is unknown. During germination, the antigenic determinant(s) of somatic polysaccharide, the cell wall Gal-NAG polysaccharide of *B. anthracis* is exposed[9].

(3) Vegetative Growth of *bacillus*

As the phagocytic capacity of the lymph node is overwhelmed, the spores progress to successive growth of vegetative *bacillus*. Depending on the growth conditions, the *bacillus* can be either encapsulated or nonencapsulated. The capsule is a polymer of γ-D-glutamic acid with molecular weights between 20 and 55 kDa in vitro and estimated to be 215 kDa in vivo[15]. This structure is poorly immunogenic to the host[16]. The capsule may inhibit host defense through inhibition of phagocytosis of the vegetative cells by macrophages. Most (if not all) of the bacilli isolated from infected host are encapsulated, thereby masking their'S-layer proteins and the cell wall polysaccharide. The capsule is thus considered to be one of the two major contributing factors to the virulence of *B. anthracis*[17-20].

(4) Toxins, Protein Factors and Polysaccharides

Vegetative *bacillus* releases multiple factors, such as toxins, cellular protein factors, and soluble polysaccharides. The presence of proteins and polysaccharides in the culture media of growing *B. anthracis* has long been recognized. In the early 1950s, potential vaccine candidates of *B. anthracis* were evaluated in animal models[8]. Different molecular fractions were injected into animals, and then these immunized animals were challenged with lethal dosages of *B. anthracis* spores. The protein fractions provided a strong protection for the immunized animals. It is now well understood that the protective antigen, abbreviated PA, is an integrated component of the lethal toxin of *B. anthracis*. It binds to a specific cellular receptor and forms toxic cell-bound complexes with edema factor (EF) and lethal factor (LF) 20-22. Neutralization antibodies to PA or a polyvalent factor that inhibits the formation of the complex may protect animals from lethal attack by the toxin[23]. A considerable number of polysaccharides are also present in the culture media growing the bacteria.

(B) Current Anthrax Vaccines

Anthrax vaccination was the first effective bacterial vaccination in history[24]. Two types of anthrax vaccines are currently in use for humans: A) the spores of the toxigenic, nonencapsulated *B. anthracis* STI-1 strain[25-27] and B) the cell-free PA-based vaccines consisting of aluminum hydroxide-adsorbed supernatant material from cultures of the toxigenic, nonencapsulated *B. anthracis* strain V770-NPI-R[28] or alum-precipitated culture filtrate from the Sterne strain.

The use of live, attenuated STI-1 occasionally results in general and local adverse responses, observed both after primary application and revaccination, and the frequency of responses increases with the number of vaccinations[29]. Such residual virulence makes it unacceptable for human use in Western countries. The PA-based cell-free vaccines from culture supernatants of the Sterne strain[30, 31] were later developed and are currently in use in Western countries. Recombinant PA can now be produced from different heterologous organisms, including *B. subtilis*[27], and the safety and consistency of the PA preparations have been improved. There are, however, concerns about its efficacy for vaccination. Multiple immunizations are required and there are cases of reactogenicity. For example, PA vaccines provide less protection than live spore vaccines against lethal challenges with several strains of *B. anthracis*[32]. Therefore, other antigens in addition to PA and/or cellular immunity may be required for full protection.

Recent efforts have been focused on genetically engineering highly attenuated spore-forming nontoxinogenic and nonencapsulated strains of *B. anthracis*, which express recombinant protective antigen (rPA) at high levels[27, 32]. Using a recombinant strain expressing high levels of rPA (>100 mg/ml), Cohen et al.[32] demonstrated that a single immunization of guinea pigs with the spores was able to induce a long lasting immune response (at least 12 months) and provided protection against a lethal challenge of virulent (Vollum) anthrax spores. The recombinant *B. anthracis* spore vaccine appears to be more efficacious than the vegetative cell vaccine, suggesting that some *B. anthracis* spore-associated antigen(s) may contribute significantly to protective immunity.

(C) Consideration of the Candidate Carbohydrate Molecules

Hybridoma and monoclonal antibody technology has provided a powerful means to explore potential molecular targets for diagnosis and vaccine development. Using the guanidine cell wall extracts of *B. anthracis* to immunize mice, Ezzell et al. were able to establish two IgM monoclonal antibodies that were directed at an epitope associated with the cell wall Gal-NAG polysaccharide[9]. Electron microscopy showed that both mAbs interacted with the cell wall of vegetative cells, as well as with the cortex of spores. Neither mAb reacted with encapsulated vegetative cells, such as those from infected guinea pigs, nor did they react with intact spores. These mAbs stained intensely to all *B. anthracis* strains tested, and with two exceptions, none of 20 other *Bacillus* strains was stained[9]. Thus, its expression is restricted to *B. anthracis* and a few *B. cereus* strains that are closely related to *B. anthracis*. This structure is, however, predominantly masked by the bacterial capsule.

Expression of spore-associated glycoproteins by several *Bacillus* species has been recently documented[12]. Garcia-Patrone and Tandecarz reported that two glycoproteins (205 kDa and 72 kDa) were found in *B. thuringiensis* sporangia[12]. These glycoproteins were predominantly localized in the exosporium and/or the spore coat, but a small proportion was also seen in membranes. Deglycosylation of these glycoproteins yielded a 54 kDa polypeptide in both cases, indicating that the 205 kDa preparation is the multimer of the 72 kDa glycoprotein. The oligosaccharides of this glycoprotein had N-acetyl-galactosamine at the reducing end, rhamnose and a component not yet identified. The rhamnose residue is seen in the microbial polysaccharide at relatively high frequency and is frequently recognized by a host as a part of a dominant antigenic structure[12, 33-38].

Using lectins as probes, Cole et al. (1983)[10] found that lectins of different sugar-binding specificities interact differentially with *Bacillus* species. *B. anthracis* was agglutinated by several lectins that are specific for α-galactose- or 2-acetamido-2-deoxy-α-D-galactose residues, including lectins of *Griffonia simplicifolia, Glycine max, abrus precatorious,* and *Ricinus communis*. By contrast, *B. mycoides* and many other *bacillus* strains were strongly reactive with the lectin from *Helix pomatia* and weakly reactive with the *Glycine max* lectin. When purified spores of several *Bacillus* species were mixed with lectins, the patterns of lectin-spore agglutinations observed were essentially similar to those of lectin-vegetative cells. These results suggest that there are sugar chain structures present on the surfaces of both spore, non-encapsulated vegetative cells, as well as spore, encapsulated vegetative cells of *B. anthracis*. Identification and characterization of these carbohydrate structures are of critical importance for spore recognition and vaccine development directed to the spores of *B. anthracis*.

II. Experimental Details and Results

Our recent efforts have been focused on developing a carbohydrate-based microarray to extend the scope of biomedical research on carbohydrate-mediated molecular recognition and anti-infection responses. We have developed a simple and efficient procedure for producing a carbohydrate microarray. In our current platform, about 20,000 microspots of antigens can be printed on a single microarray slide, reaching the capacity to include most known human microbial pathogens, auto-antigens and tumor-associated antigens. The detection system is highly sensitive and efficient. A broad spectrum of antibody specificities can be monitored with as little as a few microliters of serum specimen. This carbohydrate microarray platform is thus readily applicable for biomedical research on carbohydrate-based molecular recognition and for clinical diagnosis of infectious diseases and other diseases[39].

Applying this technology, we have conducted experiments to examine whether antibodies elicited by anthrax spore antigens contain anti-carbohydrate reactivities. Two preparations of rabbit anti-anthrax spore antibodies, one from a U.S.-based company (Catalog No. B0003-05G, United States Biological, Swampscott, Mass.) and another from a U.K.-based company (Catalog No. ab8244, Abcam Limited, Cambridge, U.K.), were employed for this investigation. We reasoned that if such antibody reactivities were present in the polyclonal anti-anthrax spore antibodies and if relevant carbohydrate structures are included on a carbohydrate microarray, staining of a microarray using anti-anthrax spore antibodies should allow us to identify the antibody reactivities on the carbohydrate microarray. Results of this investigation are summarized in FIGS. 24 and 25.

Figure 24:
Figure 24:
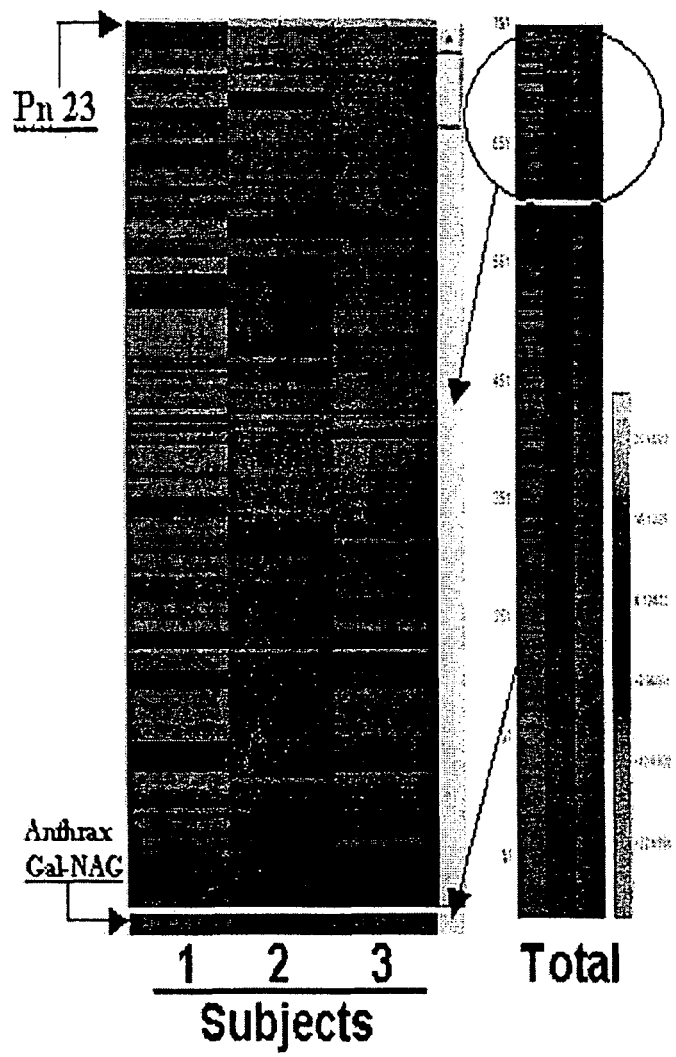
Figure 25:
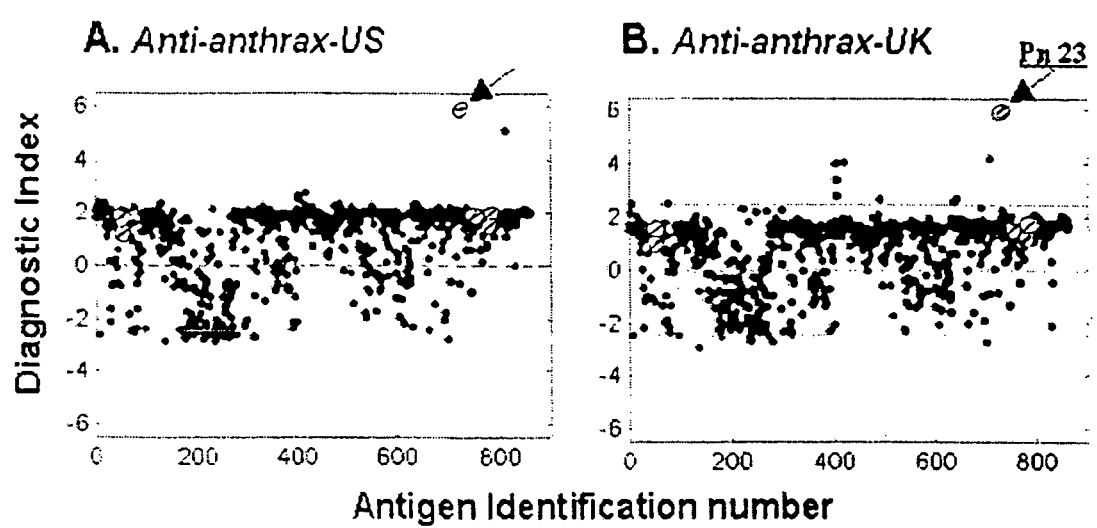

In order to facilitate the recognition of the antibody reactivities that are specifically associated with an immunization and/or an infection, we have developed a computer algorithm to extract significant biological microarray signals from a large amount of "background noise" that was generated by irrelevant antibody specificities. The latter represents the so called "pre-existing antibody sink" (FIG. 24, B-subject 1). This method is termed dimension reduction, a concept adopted from the field of communication. Results of our analysis using this method are shown in FIG. 25.

The "fingerprint" illustration of serum antibodies in FIG. 24 clearly shows that the antibody profiles of the three rabbit anti-sera are different. The anti-Pn23-polysaccharide reactivities are, however, significantly elevated in both immunized rabbit serum specimens (rabbit subjects 2 and 3).

Figure 26:
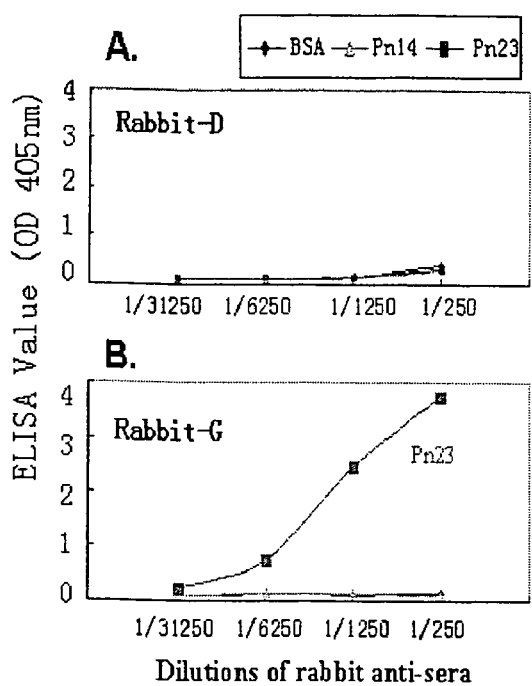

To confirm the biochip finding that anti-anthrax spore antibodies cross-react with Pn23-polysaccharide, we performed a polysaccharide antigen-specific ELISA assay on the two anti-anthrax antibodies and six rabbit serum specimens, including four non-immunized and two dextran-conjugates immunized rabbit anti-sera. The anti-Pn23-polysaccharide activities were only seen in the rabbits that were challenged with anthrax spore extracts (FIG. 26).

Figure 27:
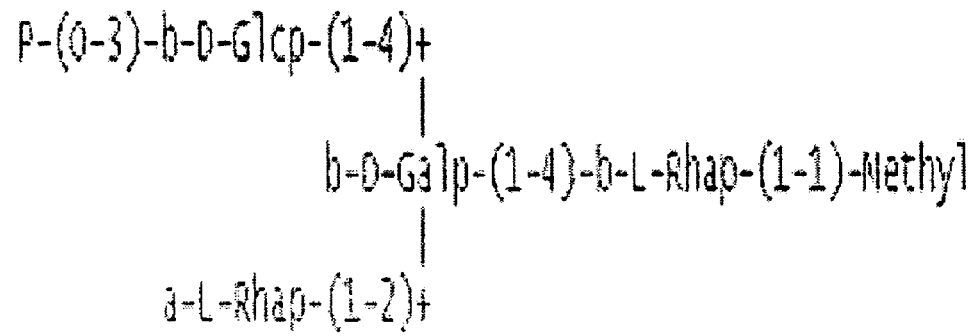

The chemical composition and structure of Pn23-polysaccharide has been extensively studied[35, 36, 40, 41]. It is composed of neutral sugar residues of D-gal., D-glu., and L-rham. These residues form the repeating unit of the capsular polysaccharide. A tetra-saccharide model of the repeating unit is shown below (FIG. 27).

Earlier works conducted by the late professor Michael Heidelberger and his colleagues[33] demonstrated that the side-chain L-rhamnose residue is immunodominant and is responsible for the strong antigenic cross-reactivities among polysaccharide antigens of Pn23, Streptococcal group B and G. Interestingly, Garcia-Patron and Tandecarz[12] reported recently that this residue is also a component of the glycoprotein of B. thuringiensis sporangia. Structural information of the oligosaccharide chain of the glycoprotein(s) of B. anthracis sporangia is currently unavailable in the literature.

To facilitate our investigation, we established a non-anthrax model to investigate the immunological cross-reactivities of anti-anthrax spore antibodies to Pn23-polysaccharide. We have specifically selected B. cereus strain 4342 from the American Type Culture Collection (ATCC) since this strain and B. anthracis are monomorphic at multiple allozyme loci, being part of the same highly related cluster of isolates within the B. cereus lineage[42, 43]. In addition, Schurch et al.[43] found recently that B. cereus strain 4342 was sensitive to the γ phage, which is distinct from most other B. cereus strains so far studied but is identical to strains of B. anthracis. We hypothesize that the two B. cereus strains share common carbohydrate structures, either on their cell walls or on the spores, or on the surfaces of both cell walls and spores.

We have tested whether the pre-incubation of antibodies with purified spores, either from B. cereus strain 4342 (closely related to B. anthracis) or B. cereus strain 246 (genetically and phenotypically distal from B. anthracis), can remove or reduce their anti-Pn23-preparations of rabbit anti-anthrax spore antibodies were incubated with spores of B. cereus 4342 (B anthracis-mimic strain) or control B. cereus strains at 4° C. overnight or at 37° C. for 60 minutes. Rabbit IgG antibodies purified by the Protein A column were applied at concentrations of 0.5 and 5 µg/ml. As determined in our preliminary investigation, their anti-Pn23 activities were detected at these antibody dilutions. The spores were removed from their antibody mixtures by centrifuge and the spore-free antibody solutions were applied for an ELISA assay to measure their anti-Pn23-polysaccharide activities.

The anti-rabbit serum was added to the tubes of spore 246, 4342, and a PBS-control. They were mixed by vigorously shaking at 4° C. overnight. The mixed compounds were centrifuged for 30 minutes at 4000 rpm at 4° C. and the supernatants were collected and were saved at 4° C. ELISA plates were coated with Pn23 5 µl/ml in 0.02M BBS, 100 µl/well at 37° C. for 2 hours. Next, the blocking reaction with 2% NBC-PBS was performed, 200 µl/well at 37° C. for 1 hour. The supernatants were added at 100 µl/well at 37° C. for 90 minutes. Anti-rabbit IgG$^{AP}$ was added at a dilution of 1:5000 in 2% NBC-PBS, 100 µl/well at 37° C. for 60 minutes. OD readings were taken at 405 nm, one hour after the substrates were added. The same experiment was repeated three times and results were expressed as the relative ELISA binding activities of each assay. The anti-Pn23 activities of the rabbit anti-anthrax spore serum that were incubated with PBS were listed as 100% activity for this comparison in FIG. 28.

Figure 28:
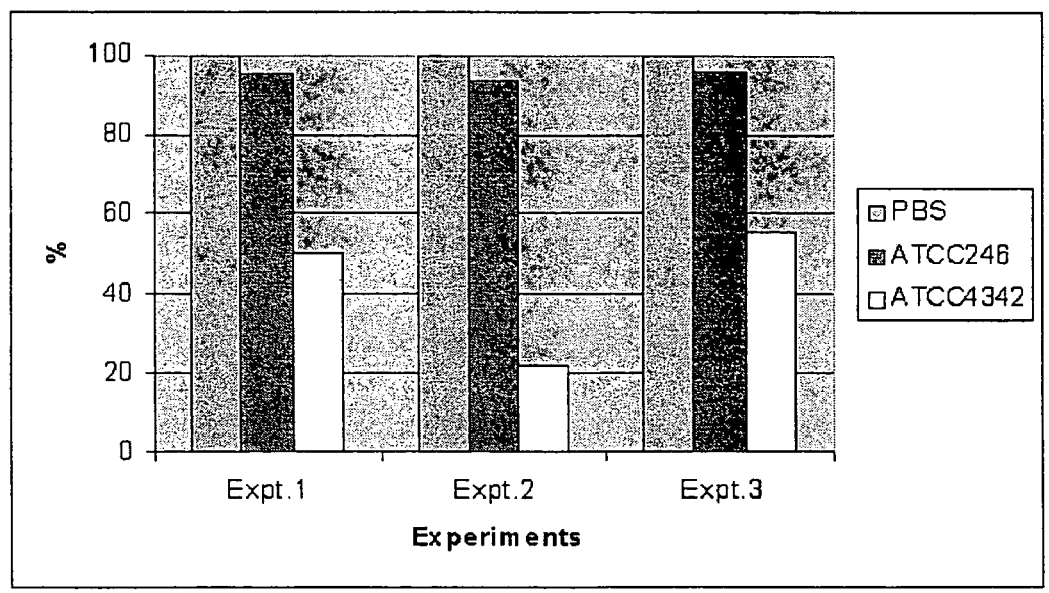

As shown in FIG. 28, such treatment using B. cereus strain 4342 but not B. cereus strain 246 was able to substantially reduce the anti-Pn23-polysaccharide activities of the anti-anthrax spore antibodies.

Given this finding, we concluded that there is present a sugar chain structure on the spores of B. cereus strain 4342 (closely related to B. anthracis) and of B. anthracis that shares antigenic similarity with Pn23-polysaccharide. Such sugar chain structure and its derivatives are potential molecular targets for the molecular recognition of B. anthracis and for vaccine development against anthrax and Pneumococcus type 23 (Pn23) infections. These include preparations of Pn23-polysaccharides, other polysaccharides with similar structures, glycoproteins and polysaccharides of B. cereus 4342 and B. anthracis, and especially the protein-conjugates of these sugar chain structures. In addition, such sugar chains can be coupled to the protective antigen (PA) of B. anthracis and other potent protein carriers. Thereby, a new generation of cell-free B. anthracis vaccines can be generated.

In summary, our recent studies applying carbohydrate microarray technology have led to the discovery of strong antigenic cross-reactivities between the anthrax spore and a capsular polysaccharide of Pn type 23. The experiments conducted supra confirm this immunological cross-reactivity. This investigation has, therefore, identified a carbohydrate structure that has great potential to serve as a new molecular target for spore recognition and for vaccination against anthrax infection.

REFERENCES

1. Karlsson, K. A., Angstrom, J., Bergstrom, J. & Lanne, B. Microbial interaction with animal cell surface carbohydrates. *APMIS. Suppl.* 27, 71-83 (1992).
2. Feizi, T. & Loveless, R. W. Carbohydrate recognition by *Mycoplasma pneumoniae* and pathologic consequences. *Am. J. Respir. Crit. Care. Med.* 154, S133-136. (1996).
3. Wang, D. & Kabat, E. A. in *Structure of Antigens.*, Vol. Three. (ed. M. H. V. V. Regenmortal) 247-276 (CRC Press, Boca Raton New York London Tokyo; 1996).
4. Finne, J., Leinonen, M. & Makela, P. H. Antigenic similarities between brain components and bacteria causing meningitis. Implications for vaccine development and pathogenesis. *Lancet.* 2, 355-357 (1983).
5. Mandrell, R. E. et al. Lipooligosaccharides (LOS) of some *Haemophilus* species mimic human glycosphingolipids, and some LOS are sialylated. *Infection. &. Immunity.* 60, 1322-1328 (1992).
6. Robbins, J. B. & Schneerson, R. Polysaccharide-protein conjugates: a new generation of vaccines. *J. Infct. Dis.* 161, 821-832 (1990).
7. Schneerson, R., Barrera, O., Sutton, A. & Robbins, J. B. Preparation, characterization, and immunogenicity of *Haemophilus influenzae* type b polysaccharide-protein conjugates. *J Exp Med* 152, 361-376. (1980).
8. Strange, R. E. & Belton, F. C. Studies on a protective antigen produced in vitro from *bacillus anthracis*: Purification and chemistry of the antigen. *Bri. J. Exp. Pathol.* 35, 153-165 (1953).
9. Ezzell, J. W., Jr., Abshire, T. G., Little, S.F., Lidgerding, B. C. & Brown, C. Identification of *Bacillus anthracis* by using monoclonal antibody to cell wall galactose-N-acetylglucosamine polysaccharide. *J Clin Microbiol* 28, 223-231. (1990).
10. Cole, H. B., Ezzell, J. W., Jr., Keller, K.F. & Doyle, R. J. Differentiation of *Bacillus anthracis* and other *Bacillus* species by lectins. *J Clin Microbiol* 19, 48-53. (1984).
11. Charlton, S., Moir, A. J., Baillie, L. & Moir, A. Characterization of the exosporium of *Bacillus cereus*. *J Appl Microbiol* 87, 241-245. (1999).
12. Garcia-Patrone, M. & Tandecarz, J. S. A glycoprotein multimer from *Bacillus thuringiensis* sporangia: dissociation into subunits and sugar composition. *Mol Cell Biochem* 145, 29-37. (1995).
13. Lincoln, R. E. et al. Role of the lymphatics in the pathogenesis of anthrax. *J Infect Dis* 115, 481-494. (1965).
14. Ross, J. M. The pathogenesis of anthrax following the administration of spores by the respiratory route. *J. Pathol. Bact.* 73, 485-494 (1957).
15. Record, B. R. Physicochemical examination of polyglutamic acid from *Bacillus anthracis* grown in vivo. *Biochem. J.* 63, 443-447 (1956).
16. Goodman, J. W. & Nitecki, D. E. Studies on the relation of a prior immune response to immunogenicity. *Immunology* 13, 577-583. (1967).
17. Zwartouw, H. T. Polyglutamic acid from *Bacillus anthracis* grown in vivo: structure and aggressin activity. *Biochem. J.* 63, 437-454 (1956).
18. Makino, S., Uchida, I., Terakado, N., Sasakawa, C. & Yoshikawa, M. Molecular characterization and protein analysis of the cap region, which is essential for encapsulation in *Bacillus anthracis*. *J Bacteriol* 171, 722-730. (1989).
19. Preisz, H. Experimentelle Studien Aber Virulenz, Empfanglichkeit and Immunitat beim Milzbrand. *Zeitschr. Immunitat.—Forsch* 5, 341-452 (1909).
20. Thorne, C. B. *Bacillus anthracis*. In *Bacillus subtilis and Other Gram-positive Bacteria*, ed. AL Sonenshein, J A Hoch, R Losick., 113-124 (1993).
21. Blaustein, R. O., Koehler, T. M., Collier, R. J. & Finkelstein, A. Anthrax toxin: channel-forming activity of protective antigen in planar phospholipid bilayers. *Proc Natl Acad Sci USA* 86, 2209-2213. (1989).
22. Escuyer, V. & Collier, R. J. Anthrax protective antigen interacts with a specific receptor on the surface of CHO-K1 cells. *Infect Immun* 59, 3381-3386. (1991).
23. Mourez, M. et al. Designing a polyvalent inhibitor of anthrax toxin. *Nat Biotechnol* 19, 958-961. (2001).
24. Mock, M. & Fouet, A. Anthrax. *Annu. Rev. Microbiol.* 55, 647-671 (2001).
25. Shlyakhov, E. N. & Rubinstein, E. Human live anthrax vaccines in the former USSR. *Vaccine* 12, 727-730. (1994).
26. Turnbull, P. C. Anthrax vaccines: past, present and future. *Vaccine* 9, 533-539. (1991).
27. Turnbull, P. C. B. Current status of immunization against anthrax: old vaccines may be here to stay for a while. *Curr. Opin. Infect. Dis.* 13, 113-120 (2000).
28. Puziss, M. et al. Large-scale production of protective antigen of *Bacillus anthracis* anaerobic cultures. *Appl. Microbiol.* 11, 330-334 (1963).
29. Stepanov, Marinin, L. I., Pomerantsev, A. P. & Staritsin, N. A. Development of novel vaccines against anthrax in man. *J. Biotechnol.* 44, 155-160. (1996).
30. Ivins, B. et al. Experimental anthrax vaccines: efficacy of adjuvants combined with protective antigen against an aerosol *Bacillus anthracis* spore challenge in guinea pigs. *Vaccine* 13, 1779-1784. (1995).
31. Friedlander, A. M., Pittman, P. R. & Parker, G. W. Anthrax vaccine: evidence for safety and efficacy against inhalational anthrax. *Jama* 282, 2104-2106. (1999).
32. Cohen, S. et al. Attenuated nontoxinogenic and nonencapsulated recombinant *Bacillus anthracis* spore vaccines protect against anthrax. *Infect Immun* 68, 4549-4558. (2000).
33. Heidelberger, M., Davie, J. M. & Krause, R. M. Cross-reactions of the group-specific polysaccharides of streptococcal groups B and G in anti-pneumococcal sera with especial reference to type 23 and its determinants. *J Immunol* 99, 794-796. (1967).
34. Allen, P. Z. & Prescott, B. Immunochemical studies on a *Mycoplasma pneumoniae* polysaccharide fraction: cross-reactions with type 23 and 32 antipneumococcal rabbit sera. *Infect Immun* 20, 421-429. (1978).
35. Richards, J. C. & Perry, M. B. Structure of the specific capsular polysaccharide of *Streptococcus pneumoniae* type 23F (American type 23). *Biochem Cell Biol* 66, 758-771. (1988).
36. Roy, A. & Roy, N. Structure of the capsular polysaccharide from *Streptococcus pneumoniae* type 23. *Carbohydr Res* 126, 271-277. (1984).
37. White-Scharf, M. E. & Rosenberg, L. T. Evidence that L-rhamnose is the antigenic determinant of hyporesponsiveness of BALB/c mice to *Klebsiella pneumoniae* type 47. *Infect Immun* 22, 18-21. (1978).

38. Lim, S. & Salton, M. R. Isolation and characterization of a succinylated polysaccharide from the cell wall of *Micrococcus agilis*. *Microbios* 44, 95-105 (1985).
39. Wang, D., Liu, S., Trummer, B. J., Deng, C. & Wang, A. Carbohydrate microarrays for the recognition of cross-reactive molecular markers of microbes and host cells. *Nat Biotechnol* 20, 275-281. (2002).
40. Ray, A. K., Maddali, U. B., Roy, A. & Roy, N. Synthesis of di- and tri-saccharides related to the polysaccharide from *Streptococcus pneumoniae* type 23 and a study of their inhibition in the precipitin reaction. *Carbohydr Res* 197, 93-100. (1990).
41. van Steijn, A. M., Kamerling, J. P. & Vliegenthart, J.F. Synthesis of a spacer-containing repeating unit of the capsular polysaccharide of *Streptococcus pneumoniae* type 23F. *Carbohydr Res* 211, 261-277. (1991).
42. Helgason, E. et al. *Bacillus anthracis, Bacillus cereus*, and *Bacillus thuringiensis*—one species on the basis of genetic evidence. *Appl Environ Microbiol* 66, 2627-2630. (2000).
43. Schuch, R., Nelson, D. & Fischetti, V. A. A bacteriolytic agent that detects and kills *Bacillus anthracis*. *Nature* 418, 884-889. (2002).

TABLE 1

Structural Properties of Dextrans and Inulin Preparations

|  | Plain dextrans | | | FITC conjugates | | | |
| --- | --- | --- | --- | --- | --- | --- | --- |
|  | N279 | LD7 | B1299S | Dex-20K | Dex-70K | Dex-2000K | Inulin |
| Structural characteristics | | | | | | | |
| Molecular Weight (kDa) | ~10,000 | 42 | ~20,000 | 19.6 | 71.2 | 2,000 | 3.2 |
| Sugar Residue Conformational characteristics | Glucose Linear Chain Dominant | Glucose Linear Chain Only | Glucose Heavily Branched | Glucose Linear Chain Dominant | Glucose Linear Chain Dominant | Glucose Linear Chain Dominant | Fructose Linear Chain Dominant (?) |
| Molar Ratio (FITC:sugar) | 0 | 0 | 0 | 0.01 | 0.005 | 0.008 | 0.007 |
| Proportions of Linkages (%)[1] | | | | | | | |
| α(1,6) Terminal nonreducing end group | 5 | 0 | 31 | 5 | 5 | 5 | 0 |
| α(1,6) Backbone | 90 | 100 | 32 | 90 | 90 | 90 | 0 |
| α(1,3)α(1,6) Backbone | 0 | 0 | 1 | 0 | 0 | 0 | 0 |
| α(1,2)α(1,6) Backbone | 0 | 0 | 5 | 0 | 0 | 0 | 0 |
| α(1,3) Branches | 5 | 0 | 1 | 5 | 5 | 5 | 0 |
| α(1,2) Branches | 0 | 0 | 30 | 0 | 0 | 0 | 0 |
| β(2,1) Linkage | 0 | 0 | 0 | 0 | 0 | 0 | 100(?) |

[1]Values are estimated from methylation and periodate-oxidation analysis (see ref. 18 for a summary).

TABLE 2

Microarray detection and characterization of human and murine anti-carbohydrate antibodies[a]

| Antigen microspots | | | | I. Human IgM | | | II. Human IgG | | | III. Anti-Dex 4.3F1 | | | IV. Anti-Dex 16.4.12E | | |
| --- | --- | --- | --- | --- | --- | --- | --- | --- | --- | --- | --- | --- | --- | --- | --- |
| Antigen name | Class[b] | ID | Location | Mean | s.d. | Int./Bk.[c] | Mean | s.d. | Int./Bk. | Mean | s.d. | Int./Bk. | Mean | s.d. | Int./Bk. |
| *Klebsiella* type 7 | 1 | 1 | A1 | 19,293 | 1,786 | 1.12 | *32,140* | *3,367* | *3.86* | 9,074 | 215 | 1.01 | 11,432 | 324 | 1.02 |
| *Klebsiella* type K11 | 1 | 2 | A2 | 19,560 | 3,349 | 1.13 | *15,262* | *7,630* | *1.52* | 9,584 | 837 | 1.06 | 11,432 | 262 | 1.03 |
| *Klebsiella* type K13 | 1 | 3 | A3 | *39,103* | *4,354* | *2.17* | 25,997 | 719 | 3.20 | 23,003 | 3,573 | 2.56 | 12,256 | 648 | 1.10 |
| *Klebsiella* type K21 | 1 | 4 | A4 | *22,847* | *2,131* | *1.27* | 29,255 | 890 | 3.63 | 8,817 | 203 | 0.98 | 12,487 | 367 | 1.12 |
| Dudmans *Rhizobium* TA1 | 1 | 5 | A5 | *31,625* | *2,768* | *1.77* | 16,198 | 693 | 2.06 | 8,438 | 448 | 0.93 | 10,901 | 226 | 0.98 |
| Chondroitin sulfate "B" | 2 | 6 | A6 | 17,009 | 633 | 0.96 | *10,830* | *411* | *1.40* | 59,264 | 822 | 6.38 | *18,063* | *935* | *1.62* |
| Pneumococcus type C | 1 | 7 | C1 | 17,014 | 1,661 | 0.98 | *25,187* | *3,499* | *3.02* | 8,813 | 373 | 0.98 | 11,256 | 271 | 1.00 |

TABLE 2-continued

Microarray detection and characterization of human and murine anti-carbohydrate antibodies[a]

| Antigen microspots | | | | I. Human IgM | | | II. Human IgG | | | III. Anti-Dex 4.3F1 | | | IV. Anti-Dex 16.4.12E | | |
|---|---|---|---|---|---|---|---|---|---|---|---|---|---|---|---|
| Antigen name | Class[b] | ID | Location | Mean | s.d. | Int./Bk.[c] | Mean | s.d. | Int./Bk. | Mean | s.d. | Int./Bk. | Mean | s.d. | Int./Bk. |
| *Pneumococcus* type VIII | 1 | 8 | C2 | 17,194 | 1,407 | 0.98 | *12,075* | *3,754* | *1.47* | 8,862 | 362 | 0.99 | 11,450 | 512 | 1.02 |
| *Pneumococcus* type XIV | 1 | 9 | C3 | 17,012 | 1,262 | 0.96 | *12,292* | *4,286* | *1.52* | 8,879 | 330 | 0.99 | 11,359 | 375 | 1.02 |
| Cow 21 (blood group B) | 3 | 10 | C4 | 19,336 | 2,180 | 1.08 | *9,280* | *839* | *1.15* | 9,020 | 325 | 1.00 | 11,309 | 450 | 1.02 |
| Bacto-agar 20° C. Ext | 1 | 11 | C5 | *19,792* | *2,512* | *1.09* | 9,682 | 1,276 | 1.20 | 9,106 | 251 | 1.02 | 11,269 | 527 | 1.02 |
| Arabino galactan (Larch) | 1 | 12 | C6 | 16,216 | 453 | 0.90 | *8,599* | *474* | *1.08* | 8,564 | 433 | 0.97 | 10,909 | 357 | 0.99 |
| IM3-BSA[d] | 4 | 13 | E1 | *19,743* | *1,898* | *1.11* | *14,322* | *1750* | *1.70* | 10,490 | 258 | 1.17 | *65,535* | *0* | *5.34* |
| IM3-KLH[d] | 4 | 14 | E2 | 18,077 | 1,185 | 1.01 | *10,641* | *930* | *1.27* | 8,629 | 390 | 0.98 | *62,128* | *5069* | *5.42* |
| Le[a] (N-110% 2x) | 3 | 15 | E3 | 17,046 | 728 | 0.95 | *8,960* | *605* | *1.08* | 8,742 | 287 | 1.00 | 11,026 | 501 | 0.98 |
| Beach P1 (blood group B) | 3 | 16 | E4 | 17,419 | 525 | 0.97 | *10,022* | *423* | *1.21* | 8,638 | 307 | 0.96 | 10,928 | 561 | 0.97 |
| Tij II (blood group B and Le[a]) | 3 | 17 | E5 | 17,946 | 464 | 0.99 | *9,400* | *503* | *1.14* | 8,556 | 202 | 0.95 | 11,006 | 457 | 0.98 |
| OG[d] | 3 | 18 | E6 | *20,682* | *2,620* | *1.13* | 8,819 | 459 | 1.08 | 8,912 | 427 | 1.00 | 11,148 | 705 | 0.99 |
| ASOR[d] | 3 | 19 | G1 | 16,555 | 449 | 0.93 | *8,933* | *320* | *1.06* | 8,627 | 547 | 0.96 | 10,923 | 566 | 1.00 |
| LNT-BSA[d] | 4 | 20 | G2 | 19,053 | 1,266 | 1.05 | *9,010* | *287* | *1.08* | 8,509 | 497 | 0.96 | 11,000 | 316 | 0.99 |
| Phosphomannan | 1 | 21 | G3 | 17,571 | 785 | 0.97 | *16,124* | *923* | *1.93* | 8,585 | 483 | 0.96 | 11,224 | 394 | 1.01 |
| *Meningococcus* group B | 1 | 22 | G4 | 16,747 | 620 | 0.93 | *8,839* | *403* | *1.06* | 8,633 | 285 | 0.96 | 11,115 | 623 | 0.99 |
| *Haemophilus influenzae* type A | 1 | 23 | G5 | 17,804 | 656 | 0.98 | *11,007* | *208* | *1.33* | 8637 | 378 | 0.95 | 11,205 | 499 | 1.01 |
| *Escherichia coli* K92 | 1 | 24 | G6 | 17,353 | 770 | 0.95 | *8,785* | *328* | *1.07* | 8,714 | 396 | 0.97 | 11,248 | 190 | 1.01 |
| *Klebsiella* type A3 | 1 | 25 | I1 | *27,018* | *9910* | *1.40* | *13,001* | *6,947* | *1.94* | 10,278 | 1,120 | 1.12 | 11,496 | 136 | 1.01 |
| *Klebsiella* type K12 | 1 | 26 | I2 | *32,322* | *16450* | *1.69* | *11,539* | *5,029* | *1.72* | 9,303 | 293 | 1.01 | 11,504 | 226 | 1.01 |
| *Klebsiella* type K14 | 1 | 27 | I3 | *23,360* | *1283* | *1.22* | *54,557* | *2,045* | *7.80* | 9,687 | 343 | 1.04 | 11,752 | 405 | 1.03 |
| *Klebsiella* type K33 | 1 | 28 | I4 | *54,607* | *2574* | *2.60* | *22,890* | *1,259* | *3.37* | *16,135* | *3,620* | *1.70* | 11,286 | 424 | 1.00 |
| Chondroitin sulfate "A" | 2 | 29 | I5 | 18,093 | 1252 | 0.99 | 7,646 | 730 | 1.16 | 9,443 | 451 | 1.01 | 11,322 | 215 | 1.00 |
| Chondroitin sulfate "C" | 2 | 30 | I6 | 17,699 | 983 | 0.97 | 7,547 | 607 | 1.14 | 11,936 | 3,057 | 1.35 | 11,810 | 396 | 1.05 |
| *Pneumococcus* type SIV | 1 | 31 | K1 | 19,002 | 662 | 1.00 | *11,485* | *819* | *1.68* | 9,305 | 351 | 1.03 | 11,388 | 94 | 1.00 |
| *Pneumococcus* type IX | 1 | 32 | K2 | 18,932 | 1303 | 1.00 | *10,600* | *3,827* | *1.56* | 9,345 | 697 | 1.02 | 11,407 | 227 | 1.01 |
| *Pneumococcus* type 27 | 1 | 33 | K3 | 23,308 | 6222 | 1.24 | 13,455 | 7,158 | 1.97 | 9,104 | 914 | 1.00 | 11,394 | 252 | 1.00 |
| Cow 26 (blood group B) | 3 | 34 | K4 | 19,184 | 1743 | 1.03 | 8,020 | 885 | 1.19 | 9,296 | 916 | 1.01 | 11,309 | 205 | 1.00 |
| *Helix pomatia* galactan | 1 | 35 | K5 | 17,885 | 722 | 0.97 | 7,298 | 550 | 1.11 | 9,186 | 917 | 0.99 | 11,369 | 268 | 1.01 |
| *Helix nemoralis* galactan | 1 | 36 | K6 | 18,135 | 715 | 0.98 | 7,412 | 416 | 1.10 | 9,179 | 773 | 0.98 | 11,234 | 185 | 1.00 |
| IM6-BSA[d] | 4 | 37 | M1 | 18,897 | 184 | 1.01 | *9,991* | *784* | *1.41* | 10,610 | 423 | 1.13 | *62,509* | *2,863* | *5.43* |
| IM6-KLH[d] | 4 | 38 | M2 | 17,761 | 289 | 0.96 | 7,857 | 544 | 1.13 | 9,303 | 250 | 1.00 | 13,534 | 460 | 1.19 |
| Le[a] (N-1 IO$_4$ NaOH) | 3 | 39 | M3 | 18,430 | 926 | 1.00 | 7,857 | 626 | 1.11 | 9,223 | 216 | 0.98 | 11,293 | 240 | 1.00 |
| Cyst 9 (blood group A) | 3 | 40 | M4 | 18,182 | 552 | 0.99 | *9,081* | *733* | *1.30* | 9,129 | 333 | 0.98 | 11,571 | 689 | 1.04 |
| Dextran N-150-N (60K) | 1 | 41 | M5 | 17,527 | 717 | 0.96 | 7,908 | 671 | 1.17 | *57,385* | *1,630* | *6.02* | 12,653 | 197 | 1.13 |
| Hog (blood group H) | 3 | 42 | M6 | 17,791 | 1,015 | 0.98 | 7,706 | 506 | 1.13 | 9,604 | 288 | 1.01 | 11,526 | 145 | 1.04 |
| AGOR[d] | 3 | 43 | O1 | 18,218 | 305 | 0.98 | 7,698 | 485 | 1.09 | 9,228 | 384 | 0.99 | 11,327 | 360 | 1.00 |
| Inulin | 1 | 44 | O2 | 17,655 | 361 | 0.95 | 7,636 | 326 | 1.08 | 9,274 | 391 | 0.99 | 11,264 | 511 | 1.00 |

TABLE 2-continued

Microarray detection and characterization of human and murine anti-carbohydrate antibodies[a]

| Antigen microspots | | | | I. Human IgM | | | II. Human IgG | | | III. Anti-Dex 4.3F1 | | | IV. Anti-Dex 16.4.12E | | |
|---|---|---|---|---|---|---|---|---|---|---|---|---|---|---|---|
| Antigen name | Class[b] | ID | Location | Mean | s.d. | Int./Bk.[c] | Mean | s.d. | Int./Bk. | Mean | s.d. | Int./Bk. | Mean | s.d. | Int./Bk. |
| Levan (B-512E) | 1 | 45 | O3 | 18,003 | 318 | 0.97 | *11,807* | *2,116* | *1.68* | 9,493 | 190 | 1.00 | 11,423 | 521 | 1.01 |
| *Meningococcus* group Y | 1 | 46 | O4 | 17,278 | 841 | 0.95 | 7,749 | 433 | 1.09 | 9,158 | 80 | 0.97 | 11,454 | 687 | 1.01 |
| *E. coli* K1 | 1 | 47 | O5 | 17,518 | 1,219 | 0.97 | 7,442 | 508 | 1.11 | 9,193 | 222 | 0.97 | 11,236 | 364 | 1.00 |
| *E. coli* K100 | 1 | 48 | O6 | 17,852 | 807 | 0.99 | *15,823* | *2,152* | *2.33* | 9,157 | 163 | 0.96 | 11,178 | 270 | 1.00 |
| Background (n = 200) | | | | 18,267 | 844 | | 7,522 | 727 | | 9,161 | 356 | | 11,252 | 365 | |
| Total number of positives: | | | | | | 12 | | | 35 | | | 4 | | | 4 |

[a]Data of four microarrays were statistically analyzed and the positive results are emphasized with bold italics. For human serum antibody staining, a positive score is given if the mean fluorescent intensity value of a microspot is significantly higher than the mean background of the identically stained microarray with the same fluorescent color. For the staining using mAbs, a positive score is given if the mean fluorescent intensity value of a microspot is at least 1.5-fold higher than the mean background.
[b]Carbohydrate antigens were classified and indicated in the table as follows: 1, polysaccharide; 2, glycosaminoglycan; 3, glycoprotein; 4, semisynthetic glycoconjugate.
[c]Int./Bk., Ratio of mean fluorescence intensity to mean background.
[d]AGOR, agalacto-orosomucoid; ASOR, Asialo-orosomucoid; IM, isomaltose oligosaccharide; KLH, keyhole limpet hemocyanin; LNT, lacto-N-tetraose; OG, Ogunsheye 10% 2X (blood group I activity).

TABLE 3

COGnitor Analysis of Annotated Genes on the PX01 Plasmid of *B. anthraces*.
Chart from Okinaka et al Journal of Bacteriology Oct. 1999 p 6509-6515.
Cog Information Calculated Independently and Added to the Chart.

| ORF | Start | Stop | Strand | Size (aa) | Description | Cog Class | Cog Category |
|---|---|---|---|---|---|---|---|
| 137 | 173709 | 173894 | 1 | 61 | Hypothetical protein similar to host factor protein 1 (68 aa), ymaH; *B. subtilis* (Z99113); 41/58 as positive (70%) | R | Uncharacterized ACR, host factor I protein |
| 139 | 174581 | 174871 | 2 | 96 | Hypothetical protein (138 aa), uvgU; *B. subtilis* (Z99121); 59/96 aa positive (61%) | O | Disulfide bond formation protein DsbB |
| 138 | 174200 | 174493 | 2 | 97 | Small DNA binding, pagR-like; *B. anthracis* (AF031382); 63/98 aa positive (70%) | K | Predicted transcriptional regulators |
| 109 | 131939 | 132238 | 2 | 99 | Similar to small DNA binding proteins, pagR; plasmid pXO1, *B. anthracis* (AF031382) (formerly called tcrA) | K | Predicted transcriptional regulators |
| 121 | 153605 | 153937 | 2 | 110 | Adenine phosphoribosyl transferase, apt; plasmid pXO1; *B. anthracis* (AF003936), similar to adenine phosphoribosyl transferase in *B. subtilis* | F | Adenine/guanine phosphoribosyltransferases and related PRPF |
| 129 | 163846 | 164238 | 1 | 130 | Truncated transposase for IS1627; *B. anthracis* (U30712); 93/137 aa positive (67%) | L | Putative transposase |
| 118 | 149232 | 149684 | 2 | 150 | Unknown function; plasmid pXO1, *B. anthracis* (L13841) | No Cog | No Cog |
| 87 | 101962 | 102444 | 2 | 160 | Unknown function, putative thioredoxin (137 aa), yoli; *B. subtilis* (Z99115); 55/99 aa positive (55%) | OC | Thiol-disulfide isomerase and thioredoxins |
| 120 | 152064 | 152636 | 1 | 190 | Putative transposase (401 aa); *S. pyogenes* (AF064540); 108/182 as positive (59%) | L | Transposase |
| 115 | 142410 | 142991 | 2 | 193 | Resolvase (191 aa), Tn1546-like; *Enterococcus faecium* (Q06237); 125/185 aa positive (67%) | L | Sine-specific recombinations, DNA investrame Pia homologs |
| 111 | 136229 | 136843 | 2 | 204 | Hypothetical protein in the protective antigen domain, ypa; plasmid pXO1; *B. anthracis* (M22589) | No Cog | No Cog |
| 127 | 162232 | 162876 | 2 | 214 | Putative transposase for IS1627; plasmid pXO1; *B. anthracis* (U30712) Sterne R. element ORF B | L | Putative transposase |
| 141 | 175663 | 176307 | 2 | 214 | Thermonuclease precursor (TNASE)/micrococcal nuclease (231 aa); *S. aureus* (p00644); 104/188 aa positive (55%) | L | Micrococcal nuclease (thermonuclease) homologs |
| 85 | 99636 | 100319 | 1 | 227 | Hypothetical protein (244 aa), ydiL ln bltr-spoIIC intergenic region; *B. subtilis* (D48802); 109/222 aa positive (49%) | R | Predicted metal-dependent membrane protease |
| 130 | 165317 | 166030 | 1 | 237 | Hypothetical protein (251 aa), yrpE; *B. subtilis* (U93875); 213/251 aa positive (84%) | No Cog | No Cog |
| 96 | 116307 | 117131 | 1 | 274 | Putative transposase for IS1627; plasmid pXO1; *B. anthracis* Sterne L. element (U30714); GeneMark.hm.ns truncates gene | L | Putative transposase |
| 91 | 109000 | 109841 | 1 | 280 | Hypothetical protein (193 aa), ywoA ln agrB-spoIIQ intergene region; *B. subtilis* (P94571); 86/170 aa positive (50%) | I | Membrane-associated phospholipid phosphatase |
| 94 | 112516 | 113403 | 1 | 296 | UDP-glucose-pyrophosphorylase (292 aa), gtaB; *B. subtilis* (Q05852); 221/286 aa positive (77%) | M | UDP-glucose pyrophosphorylase |
| 18 | 25124 | 26071 | 1 | 315 | Integrase/recombinase protein (311 aa); *M. thermoautotrophicum* (AE000865); 97/208 aa positive (46%) | L | Integrase |
| 103 | 123018 | 123971 | 1 | 317 | Probable integrase/recombinase (296 aa), ripX; *B. subtilis* (P46352); 93/193 aa positive (48%) | L | Integrase |
| 39 | 48912 | 49889 | 2 | 325 | Transposase (478 aa), IS231E; *B. thuringiensis* (Q02403); 282/299 aa positive (94%) | L | Predicted transposase |
| 112 | 138540 | 139523 | 2 | 327 | Spore germination response gerXC; plasmid pXO1; *B. anthracis* (AF108144), similar to gerKC in *B. subtilis* | No Cog | No Cog |

TABLE 3-continued

COGnitor Analysis of Annotated Genes on the PX01 Plasmid of *B. anthraces*.
Chart from Okinaka et al Journal of Bacteriology Oct. 1999 p 6509-6515.
Cog Information Calculated Independently and Added to the Chart.

| ORF | Start | Stop | Strand | Size (aa) | Description | Cog Class | Cog Category |
|---|---|---|---|---|---|---|---|
| 114 | 141002 | 142081 | 2 | 359 | Spore germination response, gerXB; plasmid pXO1; *B. anthracis* (AF108144), similar to gerKb in *Bacillus subtilis* | No Cog | No Cog |
| 132 | 167948 | 169033 | 1 | 361 | Putative integrase (356 aa); *Streptococcus mutans* (AF065141); 206/347 aa positive (59%); gene not predicted by GeneMark.hm.ns | S | Uncharacterized BCR |
| 136 | 172285 | 17380 | 1 | 364 | Response regulator aspartate phosphatase C (383 aa), rapC; *B. subtilis* (D50453); 126/238 aa positive (52%) and 52/117 aa positive (44%) | | |
| 93 | 111374 | 112474 | 1 | 366 | Hyaluronate synthase (419 aa), hasA. *Streptococcus pyogenes* (L21187); 211/287 aa positive (73%) and 36/48 aa positive (73%) | M | Glycosyltransferases, probably involved in cell wall biogenesis |
| 86 | 100777 | 101922 | 2 | 381 | Hypothetical protein (402 aa), yrkO; *B. subtilis* (D84432); 199/376 aa positive (52%) | R | Uncharacterized membrane protein |
| 54 | 67634 | 68815 | 1 | 393 | 5-layer precursor/surface layer protein (814 aa); *B. anthracis* (P49051); 162/353 aa positive (45%) (limited to SLH domains) | No Cog | No Cog |
| 45 | 57659 | 58966 | 2 | 435 | Cell division protein (372 aa), ftxZ; *P. horikoshii* (AP000001); 103/213 aa positive (48%) | D | Cell division GTPase |
| 95 | 113430 | 114761 | 1 | 443 | Putative NDP-sugar-dehydrogenase (440 aa), ywqF; *B. subtilis* (Z99122); 33/434 aa positive (76%) | | |
| 23 | 31621 | 33006 | 2 | 461 | Potential coding region (609 aa); *Clostridium difficile* (X98606); 249/390 aa positive (63%); also similar to maturase-related protein from *Pseudomonas alcaligenes*; gene not predicted by GeneMark.hm.ns | L | Retron-type reverse transcriptase |
| 81 | 95978 | 97363 | 1 | 461 | Ras- and transposon-related protein (225 aa), yocA; *B. subtilis* (AF027868); 90/158 aa positive (56%) | M | Membrane proteins related to metalloendopeptidases |
| 119 | 150042 | 151469 | 1 | 475 | trans-acting positive regulator, atxA; plasmid pXO1, *B. anthracis* (L13841) | No Cog | No Cog |
| 59 | 74068 | 75501 | 1 | 477 | Secretory protein kinase (474 aa), kin; *C. limicola* (U77780); 166/310 aa positive (53%); also similar to *B. pertusis* 339-aa VisBH11 gene product | N | Type IV secretory pathway, VirB11 components, and related AT |
| 35 | 42103 | 43539 | 1 | 478 | Transposase (478 aa), IS231E; *B. thuringiensis* (Q02403); 455/478 aa positive (74%) | L | Predicted transposase |
| 36 | 43808 | 45262 | 2 | 484 | Transposase (478 aa), 15231E; B. thuringiensis (002403); 347/468 aa r | L | Predicted transposase |
| 113 | 139480 | 140958 | 2 | 492 | Spore germination response, gerXA; plasmid pXO1; *B. anthracis* (AF108144); similar to yfkQ, gerBA, and gerAA in *B. subtilis* | No Cog | No Cog |
| 7 | 6544 | 8190 | 2 | 548 | Reverse transcriptase (574 aa), IS629; *E. coli* (AB11549); 308/543 aa positive (56%) | L | Retron-type reverse transcriptase |
| 90 | 108772 | 108730 | 1 | 652 | Hypothetical protein (980 aa), PFB0765w; *Plasmodium falciparum* (AE001417); 290/599 aa positive (48%) | L | ATPase involved in DNA repair |
| 110 | 133161 | 135455 | 2 | 764 | Anthrax toxin protective antigen, pagA, formerly pag; plasmid pXO1; *B. anthracis* (M22589) | No Cog | No Cog |
| 122 | 154224 | 156626 | 2 | 800 | Calmodulln-sensitive adenylate cyclase/edema factor, cya; plasmid pXO1; *B. anthracis* (M23179 and M24074) | D | Chromosome segregation ATPases |
| 107 | 127442 | 129871 | 1 | 809 | Anthrax toxin lethal factor, lef; plasmid pXO1; *B. anthracis* (M29081 and M30210) | No Cog | No Cog |
| 142 | 176736 | 179399 | 2 | 887 | Topoisomerase 1, topl; plasmid pXO1; *B. anthracis* (M97227) | L | Topoisomerase IA |
| 116 | 143195 | 146110 | 1 | 972 | Transposase for TN21 (988 aa), tnpA; *E. coli* (P13694); 619/916 aa positive (67%) | No Cog | No Cog |
| 79 | 91443 | 95111 | 1 | 1,222 | Hypothetical hydrophobic protein (567 aa); *Bacillus firmus* (U64515); 127/269 aa positive (47%) | N | Methyl-accepting chemotaxis protein |
| 13 | 15040 | 19002 | 2 | 1,320 | Erythrocyte invasion/rhoptry protein (2,401 aa); *P. yoelii* (U36927); 520/1194 aa positive (43%) | No Cog | No Cog |

TABLE 4

(Expt12140HIV-ratio)
Nitrocellulose and hydrogel as
substrates for carbohydrate and protein microarrays

| Human IgG | Ratio of fluorescent intensity over background of microspots | | | | | |
|---|---|---|---|---|---|---|
| | FAST Slides | | | Hydrogel | | |
| specific for | Mean | SD | Sum | Mean | SD | Sum |
| 1_Polysaccharides (2-150) n = 149 | 5.35 | 8.28 | 6383.02 | 5.17 | 10.16 | 6163.61 |

TABLE 4-continued (Expt12140HIV-ratio)
Nitrocellulose and hydrogel as
substrates for carbohydrate and protein microarrays

| | Ratio of fluorescent intensity over background of microspots | | | | | |
|---|---|---|---|---|---|---|
| Human IgG | FAST Slides | | | Hydrogel | | |
| specific for | Mean | SD | Sum | Mean | SD | Sum |
| 2_Glycosaminoglycan (GAG) (152-164) n = 13 | 1.74 | 1.08 | 181.25 | 1.81 | 0.63 | 188.30 |
| 3_Glycoprotein (166-266) n = 101 | 2.27 | 3.36 | 1836.22 | 2.79 | 4.88 | 2254.38 |
| 4_Semi-synthetic glycoconjugates (248-292) n = 45 | 1.57 | 1.02 | 313.67 | 2.01 | 1.63 | 402.20 |
| 5_Glycolipides (249-305) n = 58 | 1.45 | 0.34 | 139.52 | 1.68 | 0.19 | 161.18 |
| 6_HIV-1 proteins (307-481) n = 175 | 4.32 | 8.40 | 6051.71 | 2.61 | 6.19 | 3659.95 |
| 7_Other Proteins (483-567) n = 85 | 3.57 | 6.95 | 2428.71 | 3.44 | 6.47 | 2340.21 |
| 8_Ig (569-632) n = 64 | 4.27 | 8.11 | 2186.80 | 6.94 | 38.21 | 3554.90 |
| BK_Empty space selected (634-729) n = 96 | 1.24 | 0.11 | 951.36 | 1.61 | 0.44 | 1237.51 |
| BK_Saline spots (test for cross-contamination) (731-778) n = 48 | 1.44 | 0.54 | 553.80 | 1.86 | 1.88 | 716.07 |
| Total (n = 834) | 3.42 | 5.58 | 2633.25 | 3.37 | 9.89 | 2588.30 |

TABLE 5

GFPuv generates bright fluorescent signal upon excitation at 488 nm

| Channel | Excitation (nm) | Emission (nm) | Positive | Negative |
|---|---|---|---|---|
| dexsy | 335 | 526 | | Δ |
| FAM | 488 | 508 | ☆ | |
| Alexa488 | 488 | 522 | ☆ | |
| FluorX | 488 | 522 | ☆ | |
| JOE | 488 | 532 | ☆ | |
| FITC | 488 | 522 | ☆ | |
| Alexa532 | 543 | 570 | | Δ |
| TAMRA | 543 | 570 | | Δ |
| Cy3 | 543 | 570 | | Δ |
| Alexa546 | 543 | 570 | | Δ |
| TMR | 543 | 570 | | Δ |
| Alexa568 | 543 | 578 | | Δ |
| ROX | 594 | 614 | | Δ |
| TexasRed | 594 | 614 | | Δ |
| Alexa594 | 594 | 614 | | Δ |
| Cy5 | 633 | 670 | | Δ |
| APC | 650 | 660 | | Δ |

What is claimed is:

1. A cell-free anti-anthrax composition of matter comprising a Pneumococcus type 23 capsular polysaccharide conjugated with *Bacillus anthracis* protective antigen (PA), wherein the Pneumococcus type 23 capsular polysaccharide cross-reacts with antibodies against *Bacillus anthracis* spores and comprises L-rhamnose.

2. The composition of matter of claim 1, wherein the Pneumococcus type 23 capsular polysaccharide is the tetrasaccharide unit:

$$P\text{-}(0\text{-}3)\text{---}b\text{-}D\text{-}Glcp\text{-}(1\text{-}4)\text{+}$$
$$b\text{-}D\text{-}Galp\text{-}(1\text{-}4)\text{---}b\text{---}L\text{---}Rhap\text{---}(1\text{-}1)\text{Methyl}.$$
$$a\text{---}L\text{-}Rhap\text{-}(1\text{-}2)\text{+}$$

3. A method for immunizing a subject against *Bacillus anthracis* infection comprising administering to the subject the composition of matter of claim 1.

4. The method of claim 3, wherein the subject is a mammal.

5. The method of claim 4, wherein the mammal is a human.

* * * * *